US012350324B2

(12) United States Patent
Henriques Normark et al.

(10) Patent No.: US 12,350,324 B2
(45) Date of Patent: Jul. 8, 2025

(54) STREPTOCOCCAL VACCINES

(71) Applicant: ZALVAC AB, Stockholm (SE)

(72) Inventors: Birgitta Henriques Normark, Stockholm (SE); Staffan Normark, Stockholm (SE); Federico Iovino, Sollentuna (SE); Ana Rita Narciso, Sundbyberg (SE); Peter Mellroth, Stockholm (SE)

(73) Assignee: ZalVac AB, Stockholm (SE)

( * ) Notice: Subject to any disclaimer, the term of this patent is extended or adjusted under 35 U.S.C. 154(b) by 330 days.

(21) Appl. No.: 18/016,298

(22) PCT Filed: Jul. 12, 2021

(86) PCT No.: PCT/EP2021/069352

§ 371 (c)(1),
(2) Date: Jan. 13, 2023

(87) PCT Pub. No.: WO2022/013160

PCT Pub. Date: Jan. 20, 2022

(65) Prior Publication Data

US 2023/0270835 A1 Aug. 31, 2023

(30) Foreign Application Priority Data

Jul. 16, 2020 (SE) .................................. 2050901-4

(51) Int. Cl.
*A61K 39/09* (2006.01)
*A61K 31/04* (2006.01)
*A61P 31/04* (2006.01)
*C12N 15/74* (2006.01)
*A61K 39/00* (2006.01)

(52) U.S. Cl.
CPC ............ *A61K 39/092* (2013.01); *A61P 31/04* (2018.01); *C12N 15/746* (2013.01); *A61K 2039/55555* (2013.01); *A61K 2039/575* (2013.01)

(58) Field of Classification Search
None
See application file for complete search history.

(56) References Cited

FOREIGN PATENT DOCUMENTS

| | | |
|---|---|---|
| EP | 3312192 | 4/2018 |
| WO | WO 2001/12219 | 2/2001 |
| WO | WO 2011/008548 | 1/2011 |
| WO | WO 2018/124959 | 7/2018 |

OTHER PUBLICATIONS

Balaban et al., "Secretion of a pneumococcal type II secretion system pilus correlates with DNA uptake during transformation," Proceedings of the National Academy of Sciences of the United States of America, Feb. 2014, 111(7):E758-E765.

Barocchi, et al., "A pneumococcal pilus influences virulence and host inflammatory responses," Proceedings of the National Academy of Sciences of the United States of America, Feb. 2006, 103(8):2857-62.

Bergmann et al., "Versatility of pneumococcal surface proteins," Microbiology, 2006, 152:295-303.

Canvin et al., "The Role of Pneumolysin And Autolysin In The Pathology Of Pneumonia And Septicemia In Mice Infected With A Type 2 Pneumococcus," Journal of Infectious Diseases, Jul. 1995, 172(1): 119-123.

Chimalapati et al., "Infection with Conditionally Virulent *Streptococcus pneumoniae* Δpab Strains Induces Antibody to Conserved Protein Antigens But Does Not Protect Against Systemic Infection With Heterologous Strains," Infection and Immunity, Dec. 2011, 79(12):4965-4976.

Choi et al., "Potential usefulness of *Streptococcus pneumoniae* extracellular membrane vesicles as antibacterial vaccines," Journal of Immunology Research, Jan. 2017, vol. 2017, 8 pages.

Codemo et al., "Immunomodulatory Effects of Pneumococcal Extracellular Vesicles on Cellular And Humoral Host Defenses," Mbio, Mar./Apr. 2018, 9(2):1-15.

Cornick et al., "The global distribution and diversity of protein vaccine candidate antigens in the highly virulent *Streptococcus pnuemoniae* serotype 1," Vaccine, Feb. 2017, 35(6):972-980.

Cron et al., "Surface-associated lipoprotein PpmA of *Streptococcus pneumoniae* is involved in colonization in a strain-specific manner," Microbiology, Jul. 2009, 155:2401-2410.

Fernebro et al., "Capsular expression in *Streptococcus pneumoniae* negatively affects spontaneous and antibiotic-induced lysis and contributes to antibiotic tolerance," Jan. 2004, The Journal of Infectious Diseases, 189(2):328-338.

Frelet-Barrand et al., "Lactococcus lactis, an alternative system for functional expression of peripheral and intrinsic *Arabidopsis* membrane proteins," PloS One, 5(1), 15 pages.

Giefing et al., "Discovery of a novel class of highly conserved vaccine antigens using genomic scale antigenic fingerprinting of pneumococcus with human antibodies," Jan. 2008, The Journal of Experimental Medicine, 205(1):117-131.

Hava et al., "Large-scale identification of serotype 4 *Streptococcus pneumoniae* virulence factors," Molecular Microbiology, Sep. 2002, 45(5):1389-1405.

Iannelli et al., "Allelic variation in the highly polymorphic locus pspC of *Streptococcus pneumoniae*," Gene, Feb. 2002, 284(1-2):63-71.

International Preliminary Report on Patentability in International Appln. No. PCT/EP2021/069352, mailed on Jan. 17, 2023, 8 pages.

International Search Report and Written Opinion in International Appln. No. PCT/EP2021/069352, mailed on Nov. 11, 2021, 12 pages.

Iovino et al., "Pneumococcal meningitis is promoted by single cocci expressing pilus adhesin RrgA," The Journal of Clinical Investigation, Aug. 2016, 126(8):2821-2826.

Jakob et al., "Dimeric structure of the bacterial extracellular foldase PrsA," The Journal of Biological Chemistry, Feb. 2015, 290(6):3278-92.

(Continued)

*Primary Examiner* — Oluwatosin A Ogunbiyi
(74) *Attorney, Agent, or Firm* — Fish & Richardson P.C.

(57) ABSTRACT

An immunogenic composition comprising bacterial membrane vesicles (MVs) comprising a streptococcal MalX antigen and/or a streptococcal PrsA antigen, characterized in that the MVs do not comprise an immunogenic amount of a streptococcal PspA antigen. The membrane vesicles may be artificial membrane particles. Medical uses of the composition in particular for immunization against pneumococcal disease, and methods of manufacturing the composition.

20 Claims, 32 Drawing Sheets

Specification includes a Sequence Listing.

(56) References Cited

OTHER PUBLICATIONS

Jiang et al., "Peptidyl isomerase PrsA is surface-associated on *Streptococcus suis* and offers cross-protection against serotype 9 strain," FEMS Microbiology Letters, Jan. 2019, 366(2):1-7.
Khan et al., "Towards identifying protective B-cell epitopes: The PspA story," Frontiers in Microbiology, May 2017, vol. 8, 8 pages.
Li et al., "FastCloning: a highly simplified, purification-free, sequence- and ligation-independent PCR cloning method," BMC Biotechnology, Oct. 2011, vol. 11, 10 pages.
Littmann et al., "*Streptococcus pneumoniae* evades human dendritic cell surveillance by pneumolysin expression," Jul. 2009, EMBO Molecular Medicine, 1(4):211-222.
Mehanny et al., "Streptococcal Extracellular Membrane Vesicles Are Rapidly Internalized by Immune Cells and Alter Their Cytokine Release," Frontiers in Immunology, Feb. 2020, 11(80): 13 pages.
Mellroth et al., "LytA, major autolysin of *Streptococcus pneumoniae*, requires access to nascent peptidoglycan," The Journal of Biological Chemistry, Mar. 2012, 287(14):11018-29.
Mitchell et al., "The biology of pneumolysin," Sub-cellular Biochemistry, 2014, 80:145-60.
Moffitt et al., "T(H)17-based vaccine design for prevention of *Streptococcus pneumoniae* colonization," Cell Host & Microbe, Feb. 2011, 9(2):158-65.
Muralinath et al., "Immunization with *Salmonella enterica* serovar Typhimurium-derived outer membrane vesicles delivering the pneumococcal protein PspA confers protection against challenge with *Streptococcus pneumoniae*," Infection and Immunity, Feb. 2011, 79(2):887-94.
Olaya-Abril et al., "Characterization of protective extracellular membrane-derived vesicles produced by *Streptococcus pneumoniae*," Journal of Proteomics, Jun. 25, 2014, 106:46-60.
Pathak et al., "Factor H binding proteins protect division septa on encapsulated *Streptococcus pneumoniae* against complement C3b deposition and amplification," Aug. 2018, Nature Communications, vol. 9, 16 pages.
Que et al., "Expression of *Staphylococcus aureus* clumping factor A in *Lactococcus lactis* subsp. cremoris using a new shuttle vector," Infection and Immunity, Jun. 2000, 68(6):3516-3522.
Tettelin et al., "Complete genome sequence of a virulent isolate of *Streptococcus pneumoniae*," Jul. 2001 Science 293, 498-506.
Tu et al., "Pneumococcal Surface Protein a Inhibits Complement Activation by *Streptococcus pneumoniae*," Infection and Immunity, Sep. 1999, 67(9):4720-4724.

A

B

| Prediction of subcellular localization | Total no. of proteins | |
|---|---|---|
| | Serotype 3 | Serotype 4 |
| Cytosolic | 320 | 115 |
| Transmembrane | 53 | 53 |
| Lipoproteins | 23 | 26 |
| Cell wall | 2 | 12 |
| Secreted proteins | 4 | 10 |

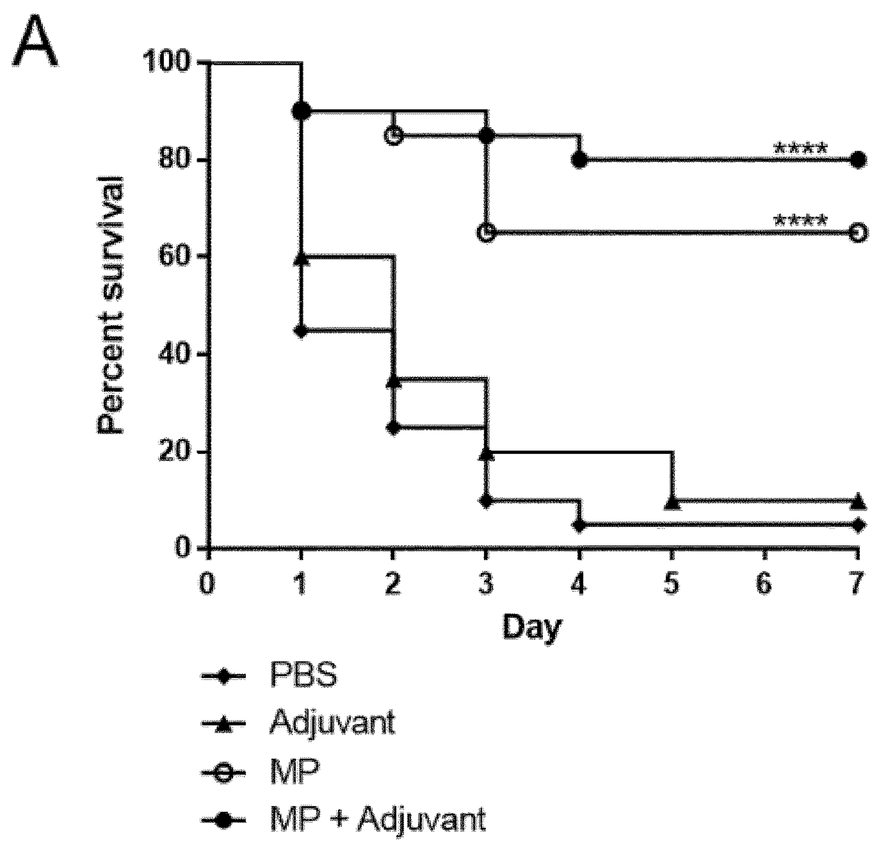
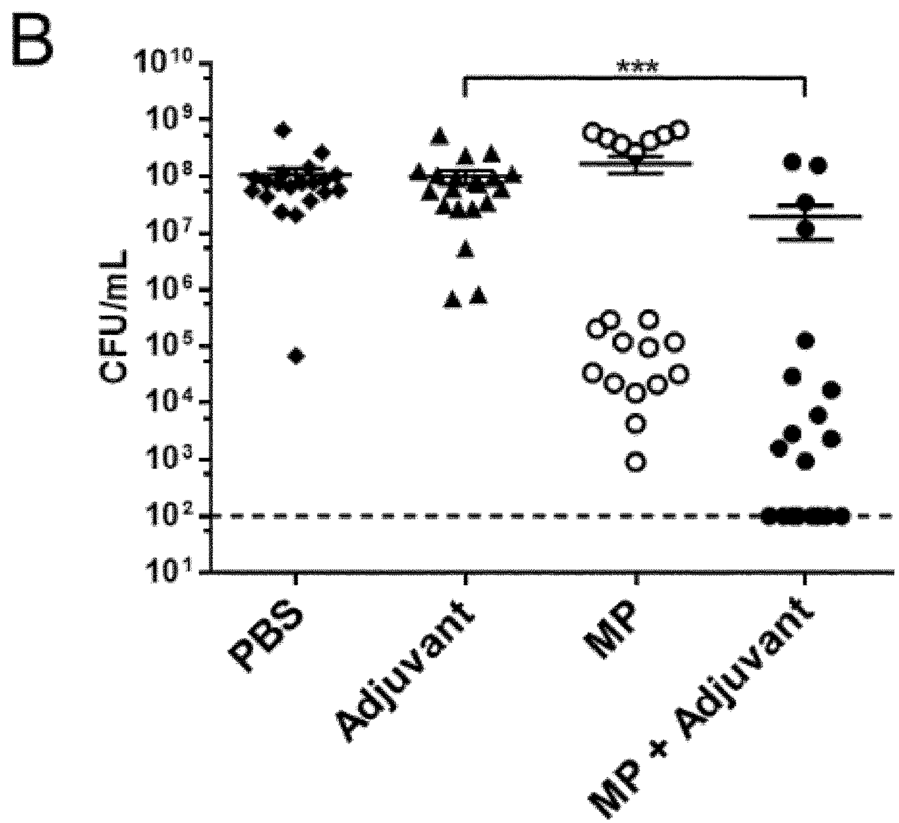
Figure 3AB.

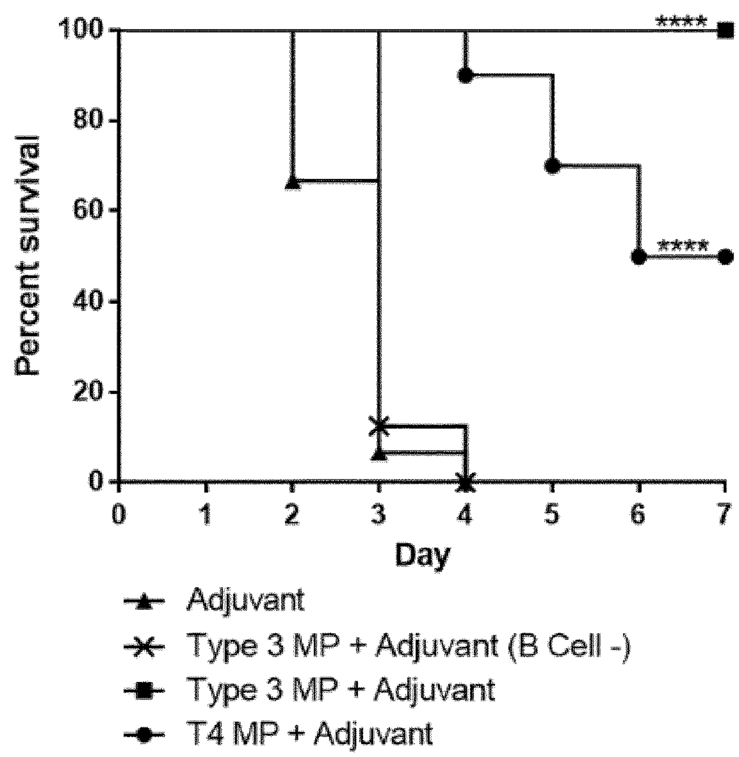
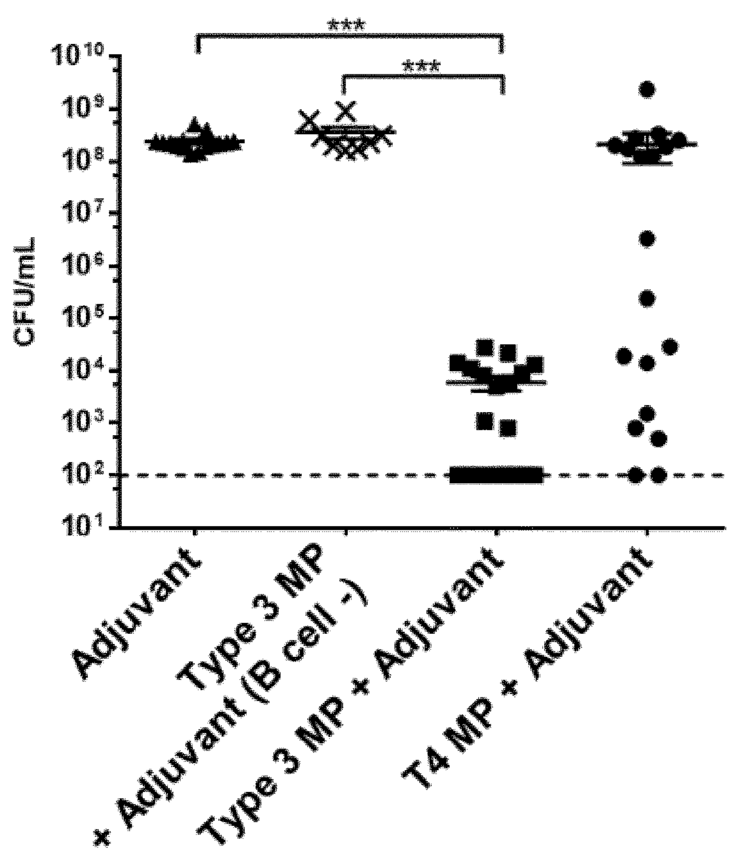
Figure 3CD.

E
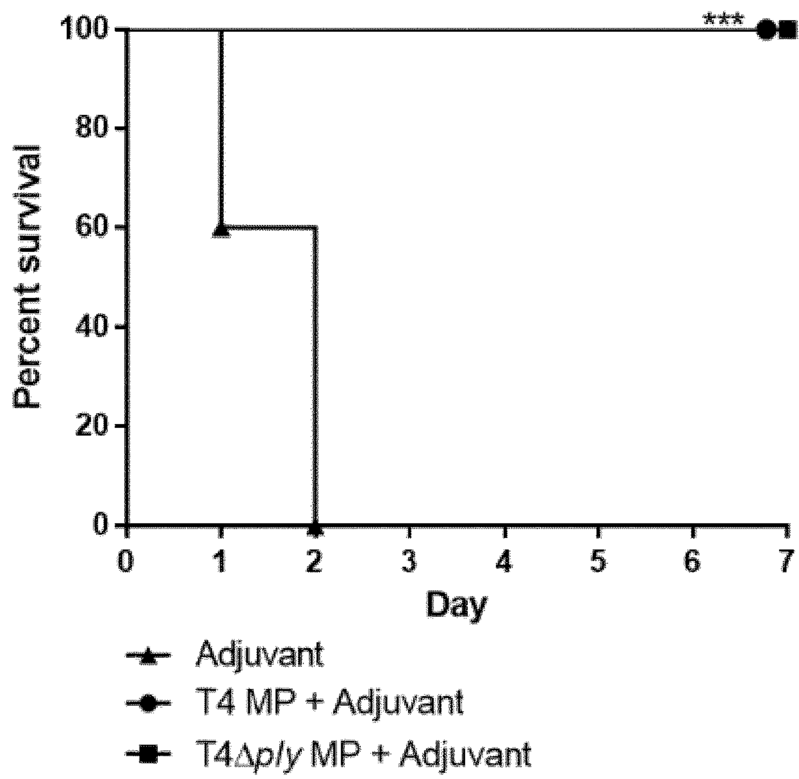
F
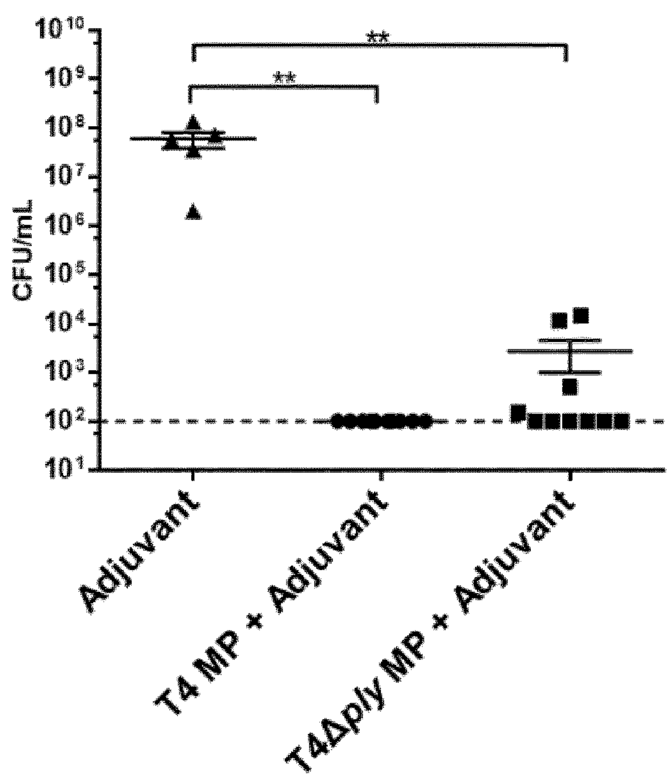
Figure 3EF.

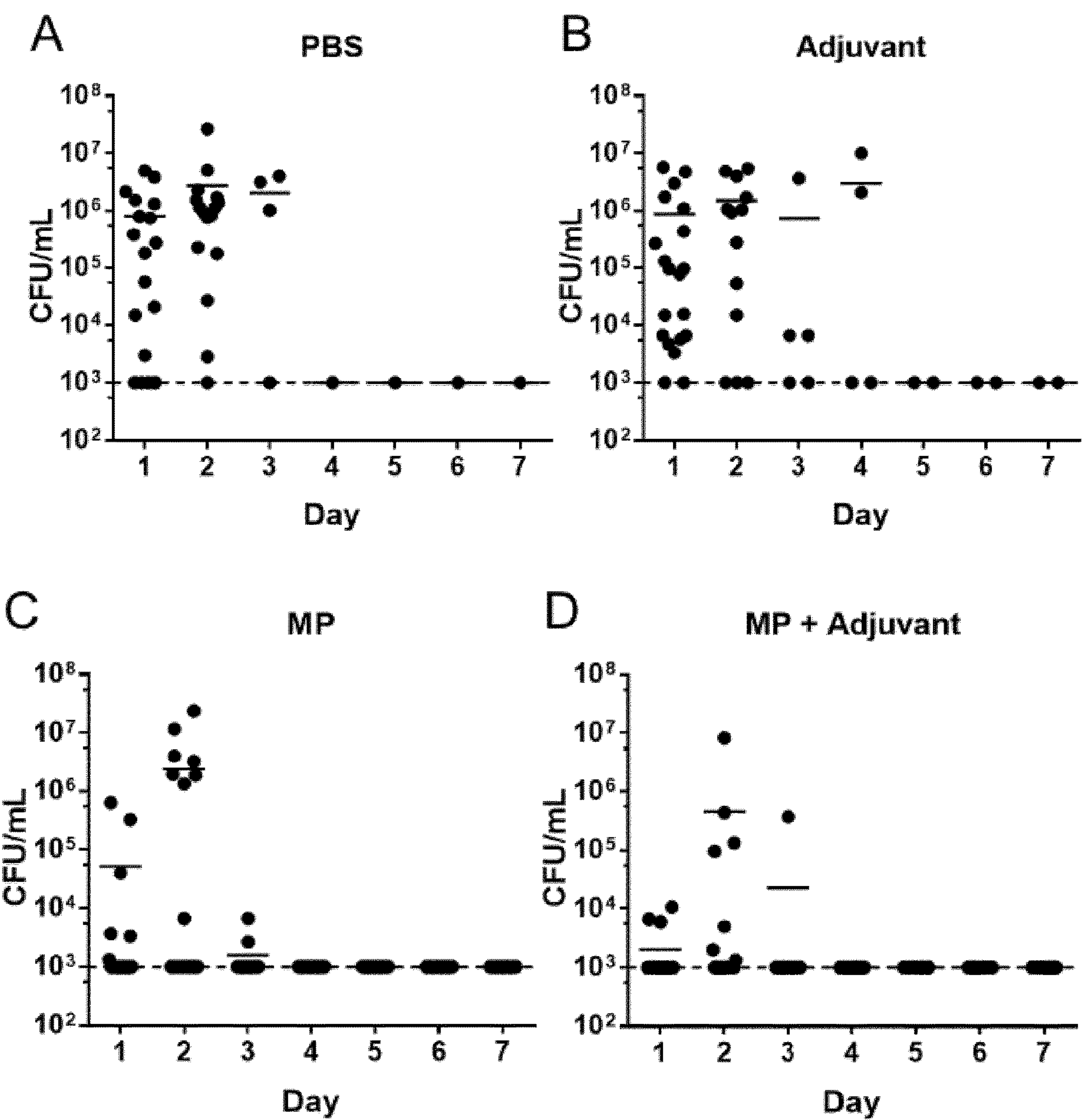
Figure 4A-D.

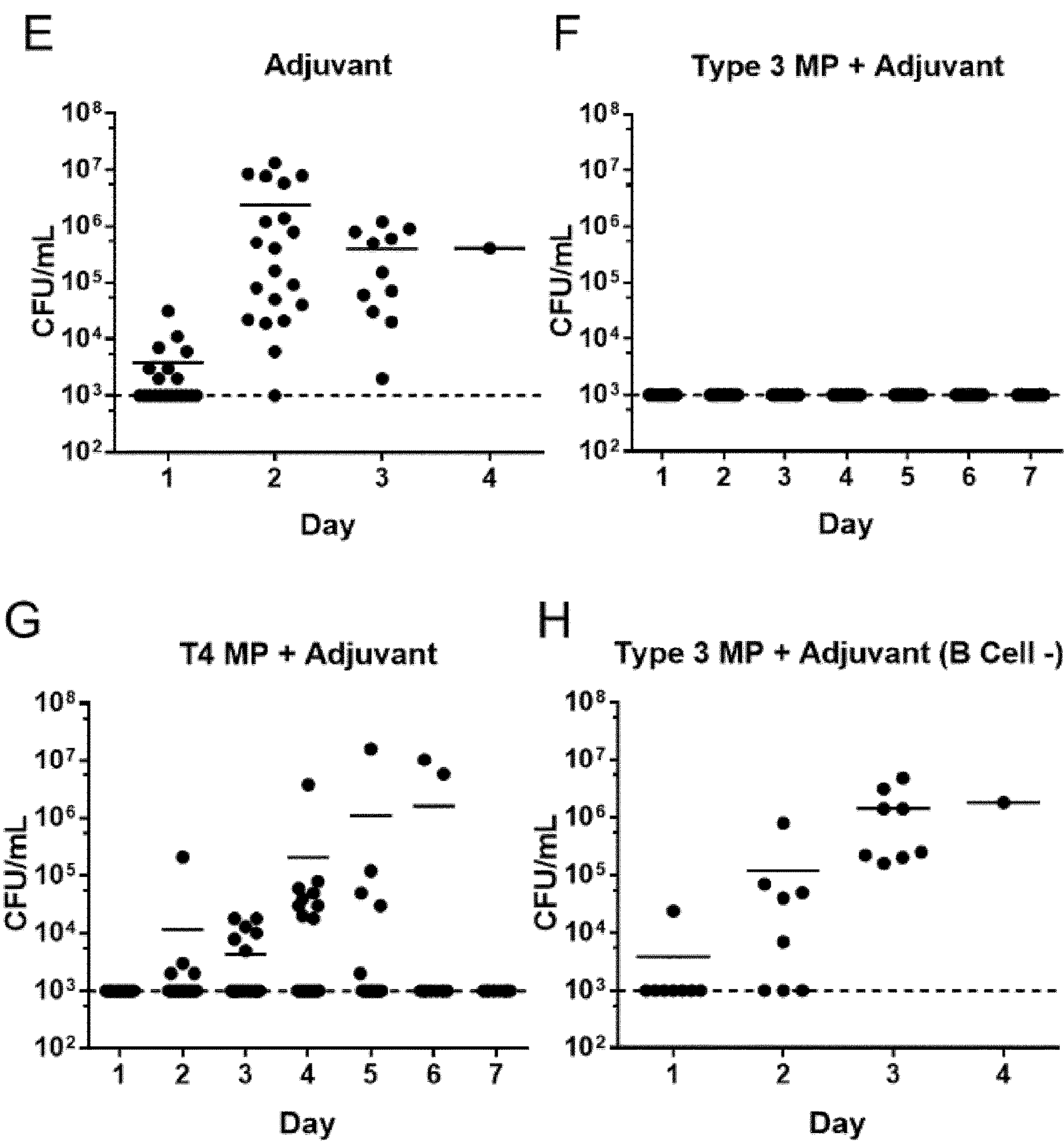
Figure 4E-H

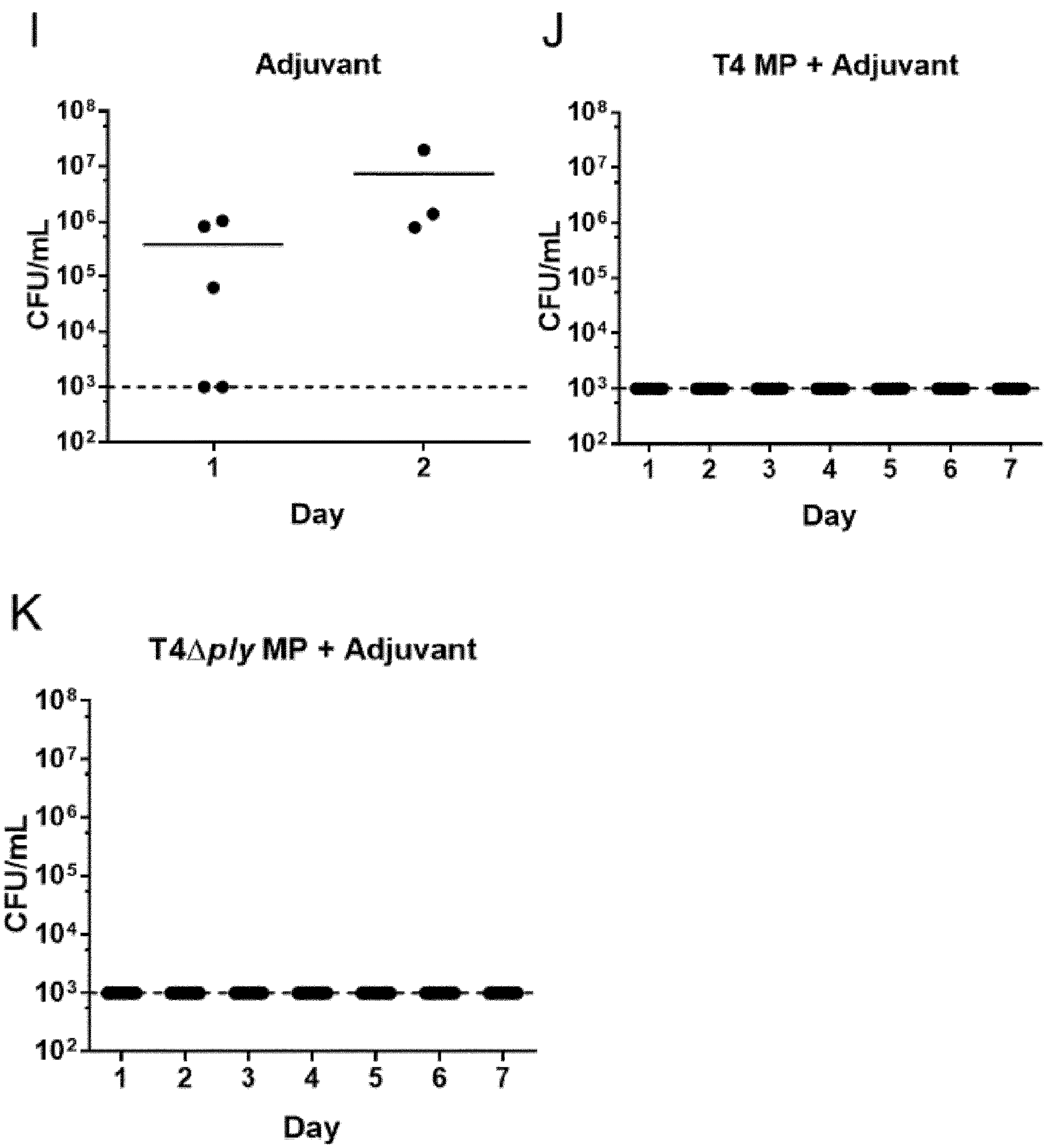
Figure 4I-K.

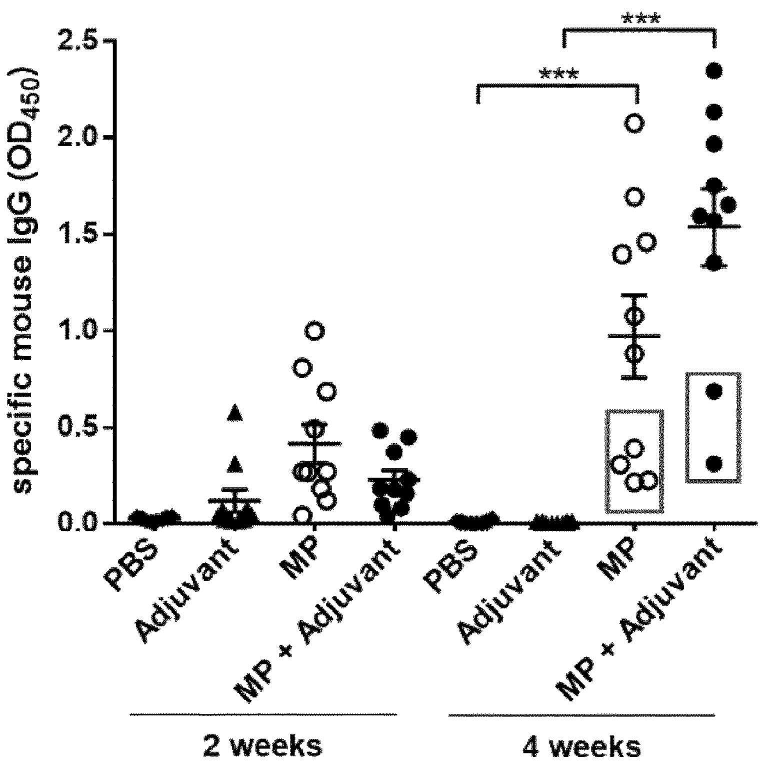
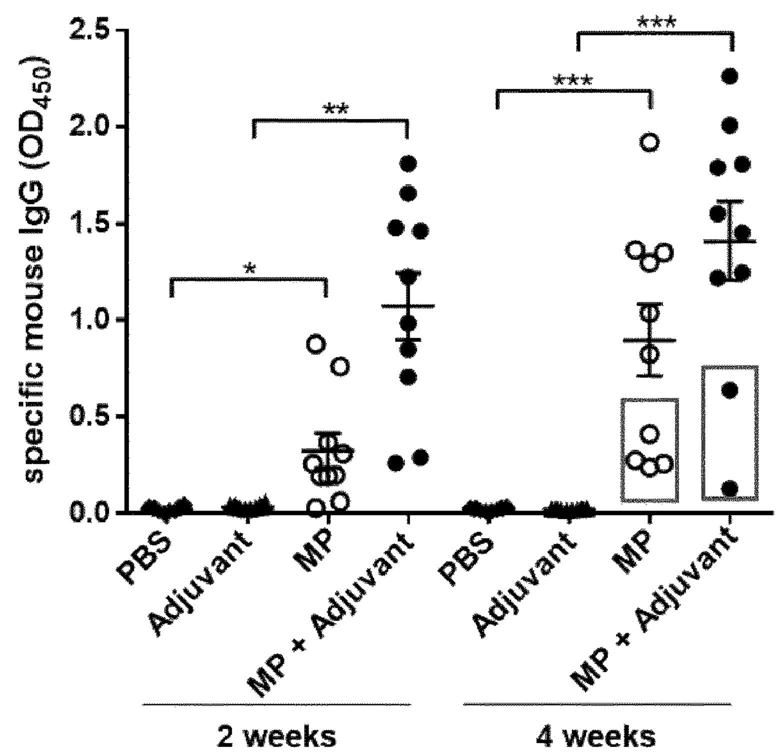
Figure 5 AB

D
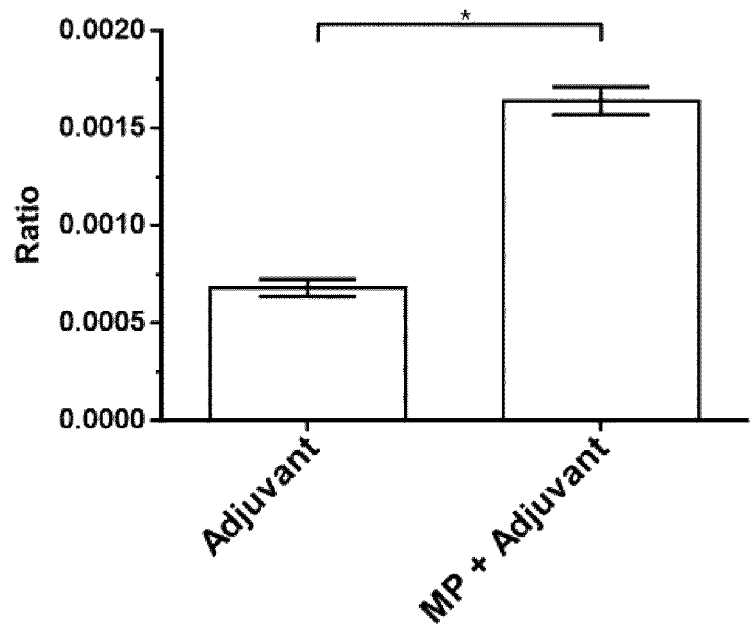
E
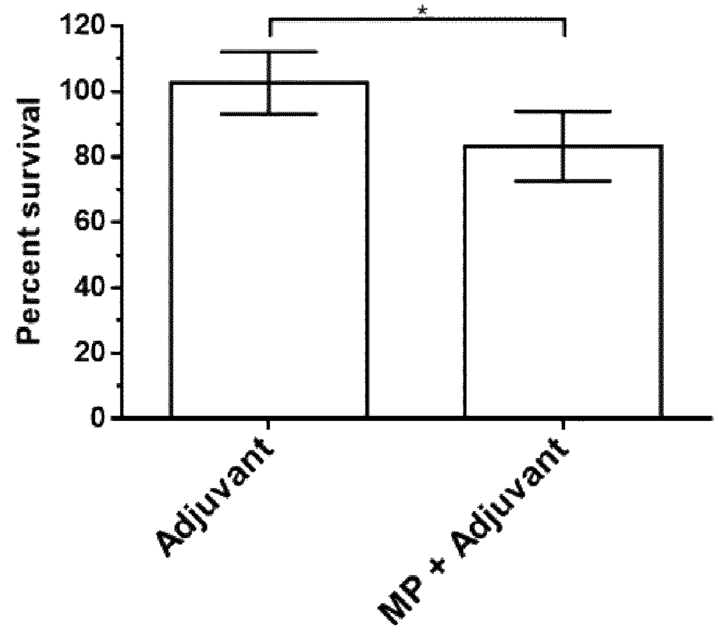
Figure 5DE

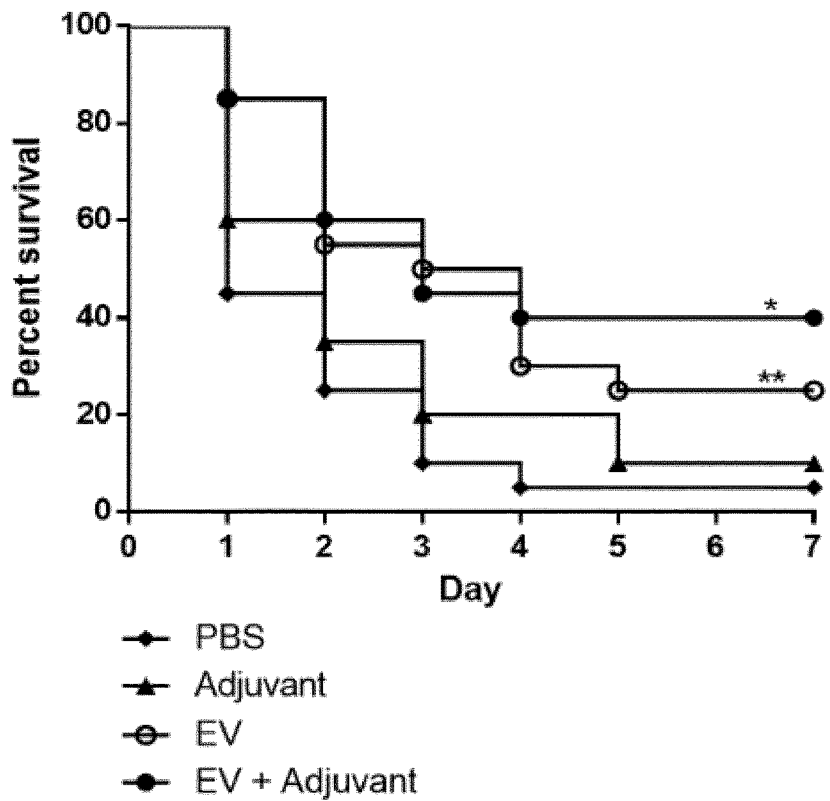
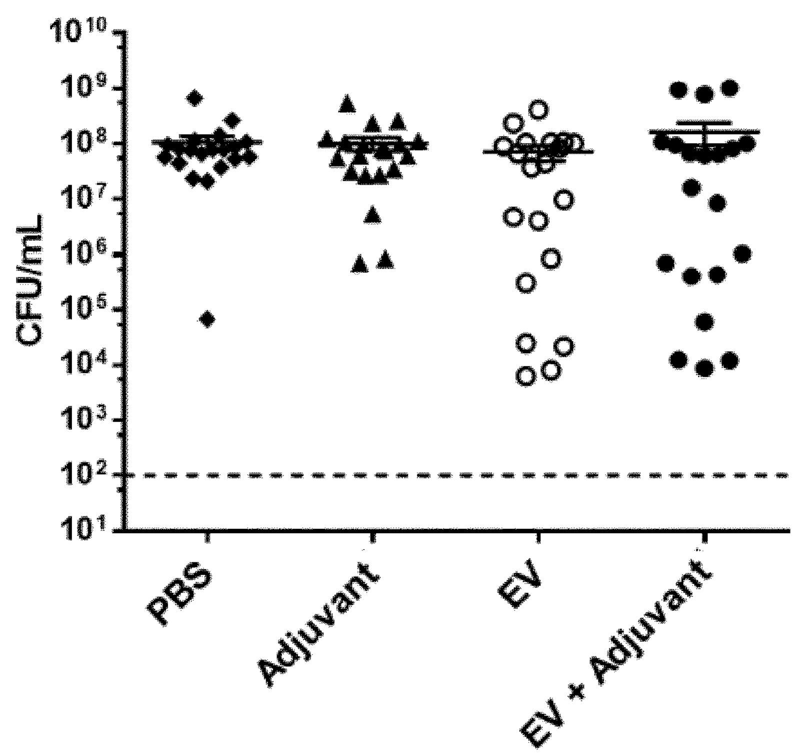
Figure 6CD

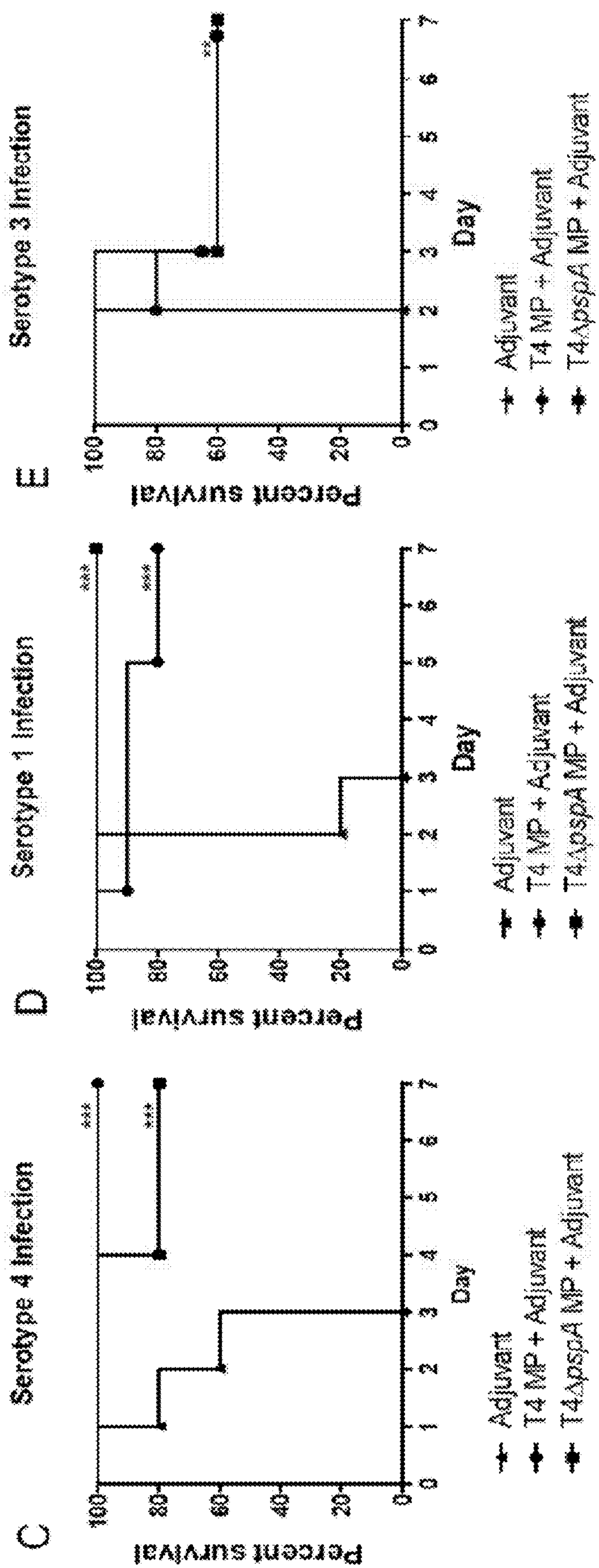
Figure 8C-E

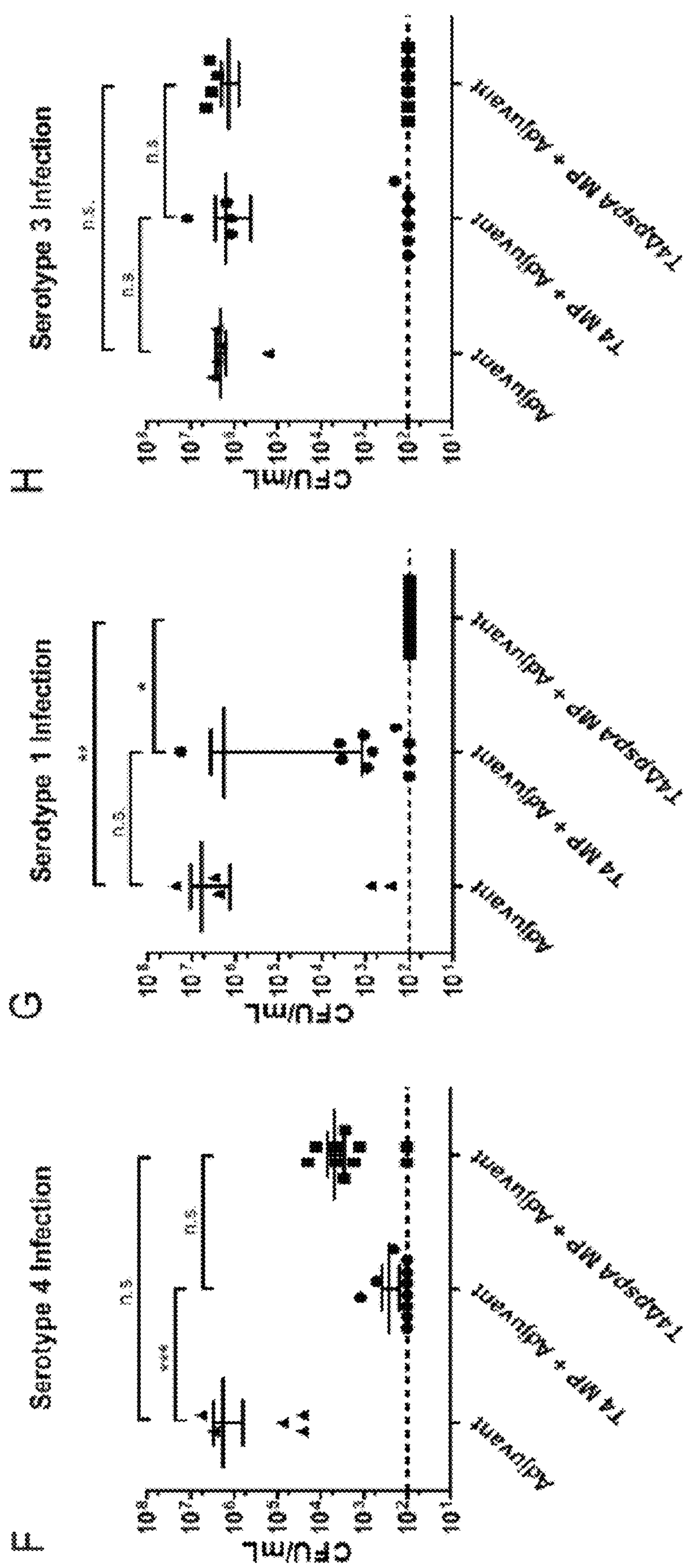
Figure 8F-H

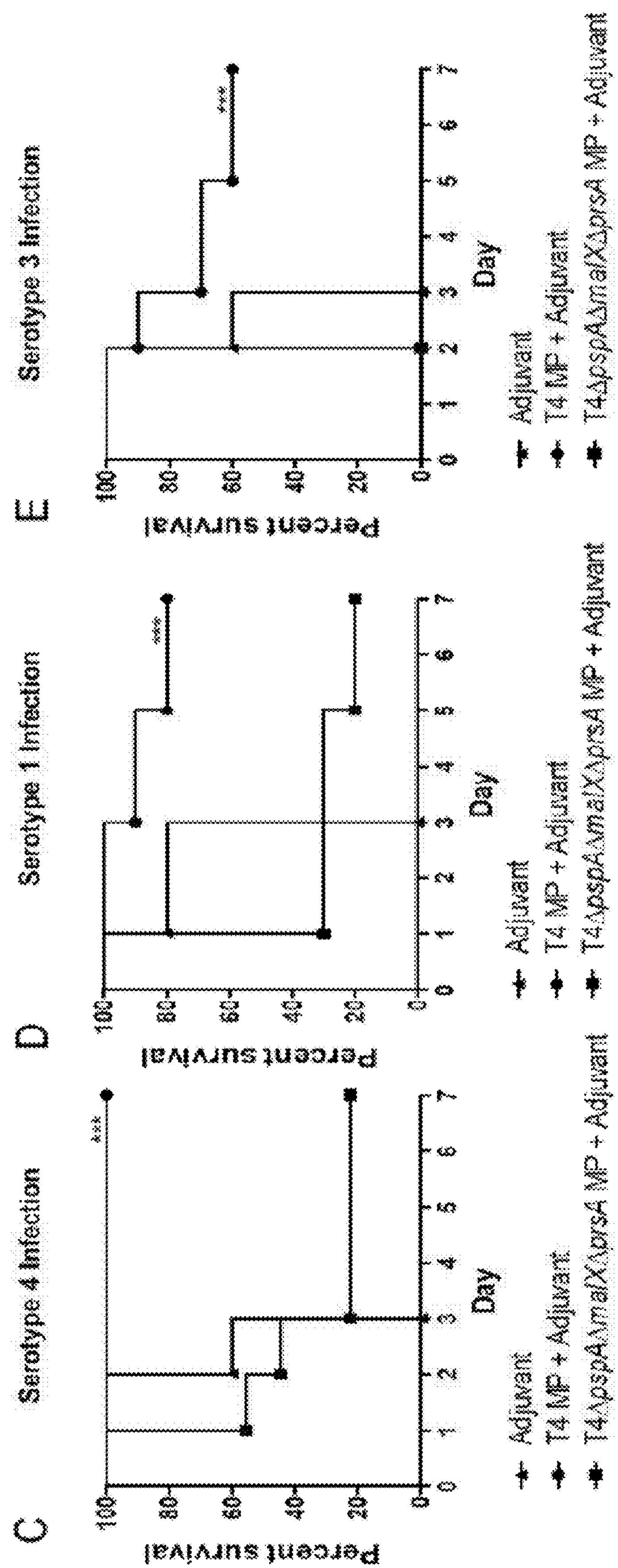
Figure 10C-E

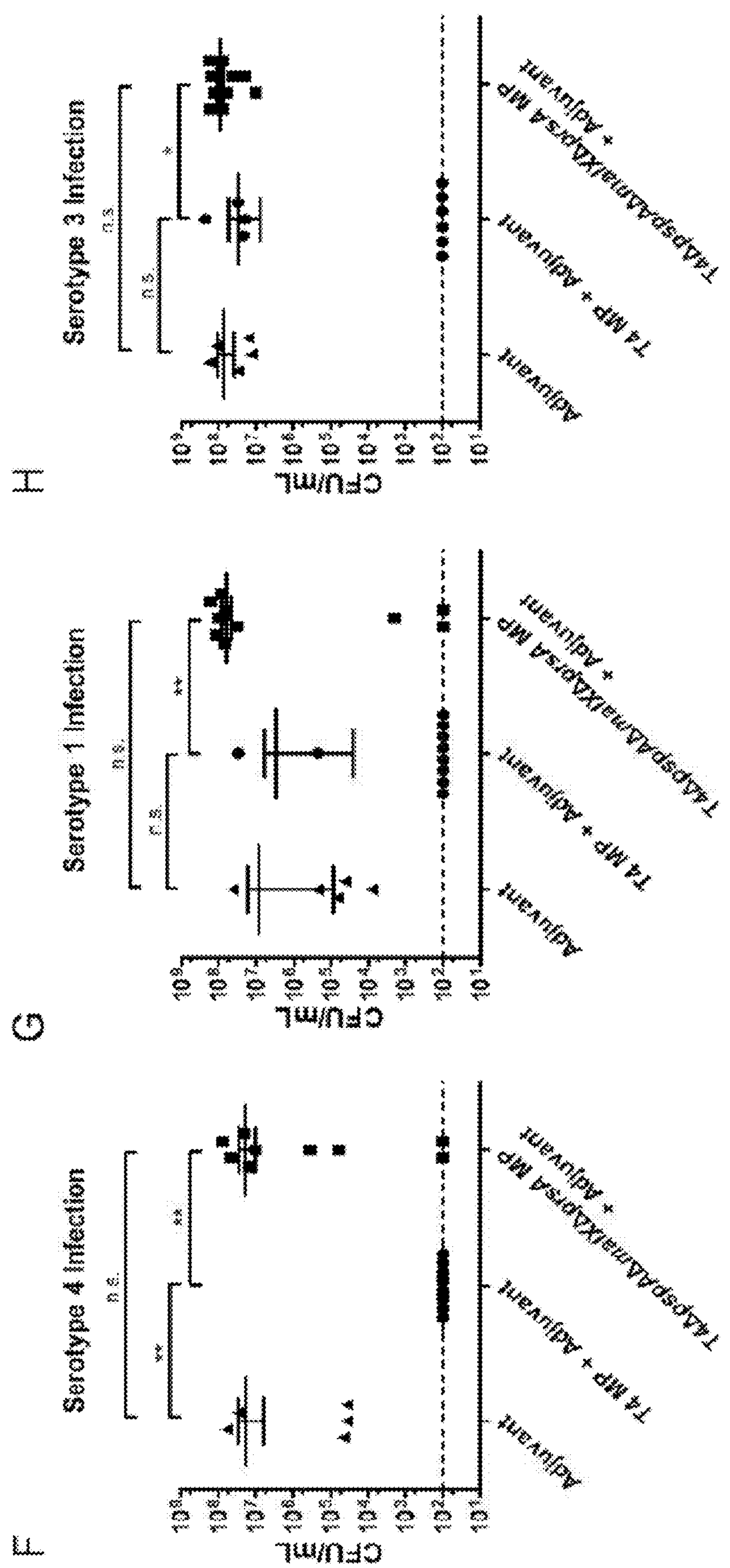
Figure 10F-H

SEQUENCE LISTING

```
<160> NUMBER OF SEQ ID NOS: 64

<210> SEQ ID NO 1
<211> LENGTH: 21
<212> TYPE: DNA
<213> ORGANISM: Artificial
<220> FEATURE:
<223> OTHER INFORMATION: Synthetic primer

<400> SEQUENCE: 1

ggagtttgtc gttgaaatta c                                              21


<210> SEQ ID NO 2
<211> LENGTH: 22
<212> TYPE: DNA
<213> ORGANISM: Artificial
<220> FEATURE:
<223> OTHER INFORMATION: Synthetic primer

<400> SEQUENCE: 2

gtatttagag attttcaaag tg                                             22


<210> SEQ ID NO 3
<211> LENGTH: 45
<212> TYPE: DNA
<213> ORGANISM: Artificial
<220> FEATURE:
<223> OTHER INFORMATION: Synthetic primer

<400> SEQUENCE: 3

tgcaagtcac acgaacacga actaaattta cctcttttct gatag                    45


<210> SEQ ID NO 4
<211> LENGTH: 44
<212> TYPE: DNA
<213> ORGANISM: Artificial
<220> FEATURE:
<223> OTHER INFORMATION: Synthetic primer

<400> SEQUENCE: 4

ctattattta acgggaggaa ataagccgat taaattaaat catg                     44


<210> SEQ ID NO 5
```

<211> LENGTH: 19
<212> TYPE: DNA
<213> ORGANISM: Artificial
<220> FEATURE:
<223> OTHER INFORMATION: Synthetic primer

<400> SEQUENCE: 5
acgtccggat ttggcgtgc 19

<210> SEQ ID NO 6
<211> LENGTH: 18
<212> TYPE: DNA
<213> ORGANISM: Artificial
<220> FEATURE:
<223> OTHER INFORMATION: Synthetic primer

<400> SEQUENCE: 6
ccactcgagc ataatgcc 18

<210> SEQ ID NO 7
<211> LENGTH: 21
<212> TYPE: DNA
<213> ORGANISM: Artificial
<220> FEATURE:
<223> OTHER INFORMATION: Synthetic primer

<400> SEQUENCE: 7
ttcgtgttcg tgtgacttgc a 21

<210> SEQ ID NO 8
<211> LENGTH: 24
<212> TYPE: DNA
<213> ORGANISM: Artificial
<220> FEATURE:
<223> OTHER INFORMATION: Synthetic primer

<400> SEQUENCE: 8
ttatttcctc ccgttaaata atag 24

<210> SEQ ID NO 9
<211> LENGTH: 21
<212> TYPE: DNA
<213> ORGANISM: Artificial
<220> FEATURE:
<223> OTHER INFORMATION: Synthetic primer

<400> SEQUENCE: 9
aggattggca taaaatggtt g 21

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10
ggtttcttga aagaattgga 20

<210> SEQ ID NO 11
<211> LENGTH: 47
<212> TYPE: DNA
<213> ORGANISM: Artificial
<220> FEATURE:
<223> OTHER INFORMATION: Synthetic primer

<400> SEQUENCE: 11
taattttcat gtgattttcc tccatgtcta ctcctttgag ataagtg 47

<210> SEQ ID NO 12
<211> LENGTH: 46
<212> TYPE: DNA
<213> ORGANISM: Artificial
<220> FEATURE:
<223> OTHER INFORMATION: Synthetic primer

<400> SEQUENCE: 12
atatatgttc aataaaataa cttagtccaa atcaatgagt caggga 46

<210> SEQ ID NO 13
<211> LENGTH: 21
<212> TYPE: DNA
<213> ORGANISM: Artificial
<220> FEATURE:
<223> OTHER INFORMATION: Synthetic primer

<400> SEQUENCE: 13
aacgcatcat atcaggtgta c 21

<210> SEQ ID NO 14
<211> LENGTH: 21
<212> TYPE: DNA
<213> ORGANISM: Artificial
<220> FEATURE:
<223> OTHER INFORMATION: Synthetic primer

<400> SEQUENCE: 14
aacgcatcat atcaggtgta c 21

<210> SEQ ID NO 15
<211> LENGTH: 25
<212> TYPE: DNA
<213> ORGANISM: Artificial
<220> FEATURE:
<223> OTHER INFORMATION: Synthetic primer

<400> SEQUENCE: 15
atggaggaaa atcacatgaa aatta 25

<210> SEQ ID NO 16
<211> LENGTH: 25
<212> TYPE: DNA
<213> ORGANISM: Artificial
<220> FEATURE:
<223> OTHER INFORMATION: Synthetic primer

<400> SEQUENCE: 16
ctaagttatt ttattgaaca tatat 25

<210> SEQ ID NO 17
<211> LENGTH: 20
<212> TYPE: DNA
<213> ORGANISM: Artificial
<220> FEATURE:
<223> OTHER INFORMATION: Synthetic primer

<400> SEQUENCE: 17
gcttccaaca aaccttgctc 20

<210> SEQ ID NO 18
<211> LENGTH: 20
<212> TYPE: DNA

<213> ORGANISM: Artificial
<220> FEATURE:
<223> OTHER INFORMATION: Synthetic primer

<400> SEQUENCE: 18
gctcctaatg gaaggatttg 20

<210> SEQ ID NO 19
<211> LENGTH: 44
<212> TYPE: DNA
<213> ORGANISM: Artificial
<220> FEATURE:
<223> OTHER INFORMATION: Synthetic primer

<400> SEQUENCE: 19
ctattcttta ggaggaatac actatggcta aaatgagaat atca 44

<210> SEQ ID NO 20
<211> LENGTH: 43
<212> TYPE: DNA
<213> ORGANISM: Artificial
<220> FEATURE:
<223> OTHER INFORMATION: Synthetic primer

<400> SEQUENCE: 20
accccccttg aacaaatttt tctaaaacaa ttcatccagt aaa 43

<210> SEQ ID NO 21
<211> LENGTH: 22
<212> TYPE: DNA
<213> ORGANISM: Artificial
<220> FEATURE:
<223> OTHER INFORMATION: Synthetic primer

<400> SEQUENCE: 21
gaaaataaca ccaaagatac gt 22

<210> SEQ ID NO 22
<211> LENGTH: 20
<212> TYPE: DNA
<213> ORGANISM: Artificial
<220> FEATURE:
<223> OTHER INFORMATION: Synthetic primer

<400> SEQUENCE: 22
agcccaaatg atagtccaag 20

<210> SEQ ID NO 23
<211> LENGTH: 21
<212> TYPE: DNA
<213> ORGANISM: Artificial
<220> FEATURE:
<223> OTHER INFORMATION: Synthetic primer

<400> SEQUENCE: 23
atggctaaaa tgagaatatc a 21

<210> SEQ ID NO 24
<211> LENGTH: 22
<212> TYPE: DNA
<213> ORGANISM: Artificial
<220> FEATURE:
<223> OTHER INFORMATION: Synthetic primer

<400> SEQUENCE: 24
ctaaaacaat tcatccagta aa 22

<210> SEQ ID NO 25
<211> LENGTH: 399
<212> TYPE: PRT
<213> ORGANISM: Streptococcus pneumoniae

<400> SEQUENCE: 25

```
Cys Gly Ser Lys Thr Ala Asp Lys Pro Ala Asp Ser Gly Ser Ser Glu
1               5                   10                  15

Val Lys Glu Leu Thr Val Tyr Val Asp Glu Gly Tyr Lys Ser Tyr Ile
            20                  25                  30

Glu Glu Val Ala Lys Ala Tyr Glu Lys Glu Ala Gly Val Lys Val Thr
        35                  40                  45

Leu Lys Thr Gly Asp Ala Leu Gly Gly Leu Asp Lys Leu Ser Leu Asp
    50                  55                  60

Asn Gln Ser Gly Asn Val Pro Asp Val Met Met Ala Pro Tyr Asp Arg
65                  70                  75                  80

Val Gly Ser Leu Gly Ser Asp Gly Gln Leu Ser Glu Val Lys Leu Ser
                85                  90                  95

Asp Gly Ala Lys Thr Asp Asp Thr Thr Lys Ser Leu Val Thr Ala Ala
            100                 105                 110

Asn Gly Lys Val Tyr Gly Ala Pro Ala Val Ile Glu Ser Leu Val Met
        115                 120                 125

Tyr Tyr Asn Lys Asp Leu Val Lys Asp Ala Pro Lys Thr Phe Ala Asp
    130                 135                 140

Leu Glu Asn Leu Ala Lys Asp Ser Lys Tyr Ala Phe Ala Gly Glu Asp
145                 150                 155                 160

Gly Lys Thr Thr Ala Phe Leu Ala Asp Trp Thr Asn Phe Tyr Tyr Thr
                165                 170                 175

Tyr Gly Leu Leu Ala Gly Asn Gly Ala Tyr Val Phe Gly Gln Asn Gly
            180                 185                 190

Lys Asp Ala Lys Asp Ile Gly Leu Ala Asn Asp Gly Ser Ile Val Gly
        195                 200                 205

Ile Asn Tyr Ala Lys Ser Trp Tyr Glu Lys Trp Pro Lys Gly Met Gln
    210                 215                 220

Asp Thr Glu Gly Ala Gly Asn Leu Ile Gln Thr Gln Phe Gln Glu Gly
225                 230                 235                 240

Lys Thr Ala Ala Ile Ile Asp Gly Pro Trp Lys Ala Gln Ala Phe Lys
                245                 250                 255

Asp Ala Lys Val Asn Tyr Gly Val Ala Thr Ile Pro Thr Leu Pro Asn
            260                 265                 270

Gly Lys Glu Tyr Ala Ala Phe Gly Gly Gly Lys Ala Trp Val Ile Pro
        275                 280                 285

Gln Ala Val Lys Asn Leu Glu Ala Ser Gln Lys Phe Val Asp Phe Leu
    290                 295                 300

Val Ala Thr Glu Gln Gln Lys Val Leu Tyr Asp Lys Thr Asn Glu Ile
305                 310                 315                 320

Pro Ala Asn Thr Glu Ala Arg Ser Tyr Ala Glu Gly Lys Asn Asp Glu
                325                 330                 335

Leu Thr Thr Ala Val Ile Lys Gln Phe Lys Asn Thr Gln Pro Leu Pro
            340                 345                 350

Asn Ile Ser Gln Met Ser Ala Val Trp Asp Pro Ala Lys Asn Met Leu
        355                 360                 365

Phe Asp Ala Val Ser Gly Gln Lys Asp Ala Lys Thr Ala Ala Asn Asp
```

```
    370                 375                 380

Ala Val Thr Leu Ile Lys Glu Thr Ile Lys Gln Lys Phe Gly Glu
385                 390                 395


<210> SEQ ID NO 26
<211> LENGTH: 293
<212> TYPE: PRT
<213> ORGANISM: Streptococcus pneumoniae

<400> SEQUENCE: 26

Cys Ser Lys Gly Ser Glu Gly Ala Asp Leu Ile Ser Met Lys Gly Asp
1               5                   10                  15

Val Ile Thr Glu His Gln Phe Tyr Glu Gln Val Lys Ser Asn Pro Ser
            20                  25                  30

Ala Gln Gln Val Leu Leu Asn Met Thr Ile Gln Lys Val Phe Glu Lys
        35                  40                  45

Gln Tyr Gly Ser Glu Leu Asp Asp Lys Glu Val Asp Asp Thr Ile Ala
    50                  55                  60

Glu Glu Lys Lys Gln Tyr Gly Glu Asn Tyr Gln Arg Val Leu Ser Gln
65                  70                  75                  80

Ala Gly Met Thr Leu Glu Thr Arg Lys Ala Gln Ile Arg Thr Ser Lys
                85                  90                  95

Leu Val Glu Leu Ala Val Lys Lys Val Ala Glu Ala Glu Leu Thr Asp
            100                 105                 110

Glu Ala Tyr Lys Lys Ala Phe Asp Glu Tyr Thr Pro Asp Val Thr Ala
        115                 120                 125

Gln Ile Ile Arg Leu Asn Asn Glu Asp Lys Ala Lys Glu Val Leu Glu
    130                 135                 140

Lys Ala Lys Ala Glu Gly Ala Asp Phe Ala Gln Leu Ala Lys Asp Asn
145                 150                 155                 160

Ser Thr Asp Glu Lys Thr Lys Glu Asn Gly Gly Glu Ile Thr Phe Asp
                165                 170                 175

Ser Ala Ser Thr Glu Val Pro Glu Gln Val Lys Lys Ala Ala Phe Ala
            180                 185                 190

Leu Asp Val Asp Gly Val Ser Asp Val Ile Thr Ala Thr Gly Thr Gln
        195                 200                 205

Ala Tyr Ser Ser Gln Tyr Tyr Ile Val Lys Leu Thr Lys Lys Thr Glu
    210                 215                 220

Lys Ser Ser Asn Ile Asp Asp Tyr Lys Glu Lys Leu Lys Thr Val Ile
225                 230                 235                 240

Leu Thr Gln Lys Gln Asn Asp Ser Thr Phe Val Gln Ser Ile Ile Gly
                245                 250                 255

Lys Glu Leu Gln Ala Ala Asn Ile Lys Val Lys Asp Gln Ala Phe Gln
            260                 265                 270

Asn Ile Phe Thr Gln Tyr Ile Gly Gly Gly Asp Ser Ser Ser Ser Ser
        275                 280                 285

Ser Thr Ser Asn Glu
    290


<210> SEQ ID NO 27
<211> LENGTH: 713
<212> TYPE: PRT
<213> ORGANISM: Streptococcus pneumoniae

<400> SEQUENCE: 27

Glu Glu Ser Pro Gln Val Val Glu Lys Ser Ser Leu Glu Lys Lys Tyr
```

-continued

```
1               5                   10                  15

Glu Glu Ala Lys Ala Lys Ala Asp Thr Ala Lys Lys Asp Tyr Glu Thr
            20                  25                  30

Ala Lys Lys Lys Ala Glu Asp Ala Gln Lys Lys Tyr Glu Asp Asp Gln
        35                  40                  45

Lys Arg Thr Glu Glu Lys Ala Arg Lys Glu Ala Glu Ala Ser Gln Lys
    50                  55                  60

Leu Asn Asp Val Ala Leu Val Val Gln Asn Ala Tyr Lys Glu Tyr Arg
65                  70                  75                  80

Glu Val Gln Asn Gln Arg Ser Lys Tyr Lys Ser Asp Ala Glu Tyr Gln
                85                  90                  95

Lys Lys Leu Thr Glu Val Asp Ser Lys Ile Glu Lys Ala Arg Lys Glu
            100                 105                 110

Gln Gln Asp Leu Gln Asn Lys Phe Asn Glu Val Arg Ala Val Val Val
        115                 120                 125

Pro Glu Pro Asn Ala Leu Ala Glu Thr Lys Lys Lys Ala Glu Glu Ala
    130                 135                 140

Lys Ala Glu Glu Lys Val Ala Lys Arg Lys Tyr Asp Tyr Ala Thr Leu
145                 150                 155                 160

Lys Val Ala Leu Ala Lys Lys Glu Val Glu Ala Lys Glu Leu Glu Ile
                165                 170                 175

Glu Lys Leu Gln Tyr Glu Ile Ser Thr Leu Glu Gln Glu Val Ala Thr
            180                 185                 190

Ala Gln His Gln Val Asp Asn Leu Lys Lys Leu Leu Ala Gly Ala Asp
        195                 200                 205

Pro Asp Asp Gly Thr Glu Val Ile Glu Ala Lys Leu Lys Lys Gly Glu
    210                 215                 220

Ala Glu Leu Asn Ala Lys Gln Ala Glu Leu Ala Lys Lys Gln Thr Glu
225                 230                 235                 240

Leu Glu Lys Leu Leu Asp Ser Leu Asp Pro Glu Gly Lys Thr Gln Asp
                245                 250                 255

Glu Leu Asp Lys Glu Ala Glu Glu Ala Glu Leu Asp Lys Lys Ala Asp
            260                 265                 270

Glu Leu Gln Asn Lys Val Ala Asp Leu Glu Lys Glu Ile Ser Asn Leu
        275                 280                 285

Glu Ile Leu Leu Gly Gly Ala Asp Pro Glu Asp Asp Thr Ala Ala Leu
    290                 295                 300

Gln Asn Lys Leu Ala Ala Lys Lys Ala Glu Leu Ala Lys Lys Gln Thr
305                 310                 315                 320

Glu Leu Glu Lys Leu Leu Asp Ser Leu Asp Pro Glu Gly Lys Thr Gln
                325                 330                 335

Asp Glu Leu Asp Lys Glu Ala Glu Glu Ala Glu Leu Asp Lys Lys Ala
            340                 345                 350

Asp Glu Leu Gln Asn Lys Val Ala Asp Leu Glu Lys Glu Ile Ser Asn
        355                 360                 365

Leu Glu Ile Leu Leu Gly Gly Ala Asp Ser Glu Asp Asp Thr Ala Ala
    370                 375                 380

Leu Gln Asn Lys Leu Ala Thr Lys Lys Ala Glu Leu Glu Lys Thr Gln
385                 390                 395                 400

Lys Glu Leu Asp Ala Ala Leu Asn Glu Leu Gly Pro Asp Gly Asp Glu
                405                 410                 415

Glu Glu Thr Pro Ala Pro Ala Pro Gln Pro Glu Gln Pro Ala Pro Ala
            420                 425                 430
```

```
Pro Lys Pro Glu Gln Pro Ala Pro Ala Pro Lys Pro Glu Gln Pro Ala
        435                 440                 445

Pro Ala Pro Lys Pro Glu Gln Pro Ala Pro Ala Pro Lys Pro Glu Gln
    450                 455                 460

Pro Ala Pro Ala Pro Lys Pro Glu Gln Pro Ala Lys Pro Glu Lys Pro
465                 470                 475                 480

Ala Glu Glu Pro Thr Gln Pro Glu Lys Pro Ala Thr Pro Lys Thr Gly
                485                 490                 495

Trp Lys Gln Glu Asn Gly Met Trp Tyr Phe Tyr Asn Thr Asp Gly Ser
            500                 505                 510

Met Ala Ile Gly Trp Leu Gln Asn Asn Gly Ser Trp Tyr Tyr Leu Asn
        515                 520                 525

Ala Asn Gly Ala Met Ala Thr Gly Trp Val Lys Asp Gly Asp Thr Trp
    530                 535                 540

Tyr Tyr Leu Glu Ala Ser Gly Ala Met Lys Ala Ser Gln Trp Phe Lys
545                 550                 555                 560

Val Ser Asp Lys Trp Tyr Tyr Val Asn Ser Asn Gly Ala Met Ala Thr
                565                 570                 575

Gly Trp Leu Gln Tyr Asn Gly Ser Trp Tyr Tyr Leu Asn Ala Asn Gly
            580                 585                 590

Asp Met Ala Thr Gly Trp Leu Gln Tyr Asn Gly Ser Trp Tyr Tyr Leu
        595                 600                 605

Asn Ala Asn Gly Asp Met Ala Thr Gly Trp Ala Lys Val Asn Gly Ser
    610                 615                 620

Trp Tyr Tyr Leu Asn Ala Asn Gly Ala Met Ala Thr Gly Trp Ala Lys
625                 630                 635                 640

Val Asn Gly Ser Trp Tyr Tyr Leu Asn Ala Asn Gly Ser Met Ala Thr
                645                 650                 655

Gly Trp Val Lys Asp Gly Asp Thr Trp Tyr Tyr Leu Glu Ala Ser Gly
            660                 665                 670

Ala Met Lys Ala Ser Gln Trp Phe Lys Val Ser Asp Lys Trp Tyr Tyr
        675                 680                 685

Val Asn Gly Leu Gly Ala Leu Ala Val Asn Thr Thr Val Asp Gly Tyr
    690                 695                 700

Lys Val Asn Ala Asn Gly Glu Trp Val
705                 710


<210> SEQ ID NO 28
<211> LENGTH: 471
<212> TYPE: PRT
<213> ORGANISM: Streptococcus pneumoniae

<400> SEQUENCE: 28

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
```

```
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470
```

<210> SEQ ID NO 29
<211> LENGTH: 318
<212> TYPE: PRT
<213> ORGANISM: Streptococcus pneumoniae

<400> SEQUENCE: 29

Met Glu Ile Asn Val Ser Lys Leu Arg Thr Asp Leu Pro Gln Val Gly
1 5 10 15

Val Gln Pro Tyr Arg Gln Val His Ala His Ser Thr Gly Asn Pro His
20 25 30

Ser Thr Val Gln Asn Glu Ala Asp Tyr His Trp Arg Lys Asp Pro Glu
35 40 45

Leu Gly Phe Phe Ser His Ile Val Gly Asn Gly Cys Ile Met Gln Val
50 55 60

Gly Pro Val Asp Asn Gly Ala Trp Asp Val Gly Gly Gly Trp Asn Ala
65 70 75 80

Glu Thr Tyr Ala Ala Val Glu Leu Ile Glu Ser His Ser Thr Lys Glu
85 90 95

Glu Phe Met Thr Asp Tyr Arg Leu Tyr Ile Glu Leu Leu Arg Asn Leu
100 105 110

Ala Asp Glu Ala Gly Leu Pro Lys Thr Leu Asp Thr Gly Ser Leu Ala
115 120 125

Gly Ile Lys Thr His Glu Tyr Cys Thr Asn Asn Gln Pro Asn Asn His
130 135 140

Ser Asp His Val Asp Pro Tyr Pro Tyr Leu Ala Lys Trp Gly Ile Ser
145 150 155 160

Arg Glu Gln Phe Lys His Asp Ile Glu Asn Gly Leu Thr Ile Glu Thr
165 170 175

Gly Trp Gln Lys Asn Asp Thr Gly Tyr Trp Tyr Val His Ser Asp Gly
180 185 190

Ser Tyr Pro Lys Asp Lys Phe Glu Lys Ile Asn Gly Thr Trp Tyr Tyr
195 200 205

Phe Asp Ser Ser Gly Tyr Met Leu Ala Asp Arg Trp Arg Lys His Thr
210 215 220

Asp Gly Asn Trp Tyr Trp Phe Asp Asn Ser Gly Glu Met Ala Thr Gly
225 230 235 240

Trp Lys Lys Ile Ala Asp Lys Trp Tyr Tyr Phe Asn Glu Glu Gly Ala
245 250 255

Met Lys Thr Gly Trp Val Lys Tyr Lys Asp Thr Trp Tyr Tyr Leu Asp
260 265 270

Ala Lys Glu Gly Ala Met Val Ser Asn Ala Phe Ile Gln Ser Ala Asp
275 280 285

Gly Thr Gly Trp Tyr Tyr Leu Lys Pro Asp Gly Thr Leu Ala Asp Lys
290 295 300

Pro Glu Phe Thr Val Glu Pro Asp Gly Leu Ile Thr Val Lys
305 310 315

<210> SEQ ID NO 30
<211> LENGTH: 929
<212> TYPE: PRT
<213> ORGANISM: Streptococcus pneumoniae

<400> SEQUENCE: 30

Met Phe Ala Ser Lys Ser Glu Arg Lys Val His Tyr Ser Ile Arg Lys
1 5 10 15

Phe Ser Ile Gly Val Ala Ser Val Ala Val Ala Ser Leu Phe Leu Gly
20 25 30

Gly Val Val His Ala Glu Gly Val Arg Ser Gly Asn Asn Leu Thr Val
35 40 45

```
Thr Ser Ser Gly Gln Asp Ile Ser Lys Lys Tyr Ala Asp Glu Val Glu
    50                  55                  60

Ser His Leu Glu Ser Ile Leu Lys Asp Val Lys Lys Asn Leu Lys Lys
65                  70                  75                  80

Val Gln His Thr Gln Asn Val Gly Leu Ile Thr Lys Leu Ser Glu Ile
                85                  90                  95

Lys Lys Lys Tyr Leu Tyr Asp Leu Lys Val Asn Val Leu Ser Glu Ala
            100                 105                 110

Glu Leu Thr Ser Lys Thr Lys Glu Thr Lys Glu Lys Leu Thr Ala Thr
        115                 120                 125

Phe Glu Gln Phe Lys Lys Asp Thr Leu Pro Thr Glu Pro Glu Lys Lys
    130                 135                 140

Val Ala Glu Ala Gln Lys Lys Val Glu Glu Ala Lys Lys Lys Ala Glu
145                 150                 155                 160

Asp Gln Lys Glu Lys Asp Arg Arg Asn Tyr Pro Thr Ile Thr Tyr Lys
                165                 170                 175

Thr Leu Glu Leu Glu Ile Ala Glu Ser Asp Val Glu Val Lys Lys Ala
            180                 185                 190

Glu Leu Glu Leu Val Lys Val Lys Ala Lys Glu Ser Gln Asp Glu Glu
        195                 200                 205

Lys Ile Lys Gln Ala Glu Ala Glu Val Glu Ser Lys Gln Ala Glu Ala
    210                 215                 220

Thr Arg Leu Lys Lys Ile Lys Thr Asp Arg Glu Glu Ala Lys Arg Lys
225                 230                 235                 240

Ala Asp Ala Lys Leu Lys Glu Ala Val Glu Lys Asn Val Ala Thr Ser
                245                 250                 255

Glu Gln Asp Lys Pro Lys Arg Arg Ala Lys Arg Gly Val Ser Gly Glu
            260                 265                 270

Leu Ala Thr Pro Asp Lys Lys Glu Asn Asp Ala Lys Ser Ser Asp Ser
        275                 280                 285

Ser Val Gly Glu Glu Thr Leu Pro Ser Pro Ser Leu Asn Met Ala Asn
    290                 295                 300

Glu Ser Gln Thr Glu His Arg Lys Asp Val Asp Glu Tyr Ile Lys Lys
305                 310                 315                 320

Met Leu Ser Glu Ile Gln Leu Asp Arg Arg Lys His Thr Gln Asn Val
                325                 330                 335

Asn Leu Asn Ile Lys Leu Ser Ala Ile Lys Thr Lys Tyr Leu Tyr Glu
            340                 345                 350

Leu Ser Val Leu Lys Glu Asn Ser Lys Lys Glu Glu Leu Thr Ser Lys
        355                 360                 365

Thr Lys Ala Glu Leu Thr Ala Ala Phe Glu Gln Phe Lys Lys Asp Thr
    370                 375                 380

Leu Lys Pro Glu Lys Lys Val Ala Glu Ala Glu Lys Lys Val Glu Glu
385                 390                 395                 400

Ala Lys Lys Lys Ala Lys Asp Gln Lys Glu Glu Asp Arg Arg Asn Tyr
                405                 410                 415

Pro Thr Asn Thr Tyr Lys Thr Leu Glu Leu Glu Ile Ala Glu Ser Asp
            420                 425                 430

Val Lys Val Lys Glu Ala Glu Leu Glu Leu Val Lys Glu Glu Ala Asn
        435                 440                 445

Glu Ser Arg Asn Glu Glu Lys Ile Lys Gln Ala Lys Glu Lys Val Glu
    450                 455                 460
```

```
Ser Lys Lys Ala Glu Ala Thr Arg Leu Glu Lys Ile Lys Thr Asp Arg
465                 470                 475                 480

Lys Lys Ala Glu Glu Glu Ala Lys Arg Lys Ala Glu Glu Ser Glu Lys
                485                 490                 495

Lys Ala Ala Glu Ala Lys Gln Lys Val Asp Ala Glu Glu Tyr Ala Leu
            500                 505                 510

Glu Ala Lys Ile Ala Glu Leu Glu Tyr Glu Val Gln Arg Leu Glu Lys
        515                 520                 525

Glu Leu Lys Glu Ile Asp Glu Ser Asp Ser Glu Asp Tyr Leu Lys Glu
    530                 535                 540

Gly Leu Arg Ala Pro Leu Gln Ser Lys Leu Asp Thr Lys Lys Ala Lys
545                 550                 555                 560

Leu Ser Lys Leu Glu Glu Leu Ser Asp Lys Ile Asp Glu Leu Asp Ala
                565                 570                 575

Glu Ile Ala Lys Leu Glu Val Gln Leu Lys Asp Ala Glu Gly Asn Asn
            580                 585                 590

Asn Val Glu Ala Tyr Phe Lys Glu Gly Leu Glu Lys Thr Thr Ala Glu
        595                 600                 605

Lys Lys Ala Glu Leu Glu Lys Ala Glu Ala Asp Leu Lys Lys Ala Val
    610                 615                 620

Asp Glu Pro Glu Thr Pro Ala Pro Ala Pro Gln Pro Ala Pro Ala Pro
625                 630                 635                 640

Glu Lys Pro Ala Glu Lys Pro Ala Pro Ala Pro Glu Lys Pro Ala Pro
                645                 650                 655

Ala Pro Glu Lys Pro Ala Pro Ala Pro Glu Lys Pro Ala Pro Ala Pro
            660                 665                 670

Glu Lys Pro Ala Pro Ala Pro Glu Lys Pro Ala Pro Thr Pro Glu Thr
        675                 680                 685

Pro Lys Thr Gly Trp Lys Gln Glu Asn Gly Met Trp Tyr Phe Tyr Asn
    690                 695                 700

Thr Asp Gly Ser Met Ala Thr Gly Trp Leu Gln Asn Asn Gly Ser Trp
705                 710                 715                 720

Tyr Tyr Leu Asn Ser Asn Gly Ala Met Ala Thr Gly Trp Leu Gln Asn
                725                 730                 735

Asn Gly Ser Trp Tyr Tyr Leu Asn Ser Asn Gly Ala Met Ala Thr Gly
            740                 745                 750

Trp Leu Gln Tyr Asn Gly Ser Trp Tyr Tyr Leu Asn Ala Asn Gly Asp
        755                 760                 765

Met Ala Thr Gly Trp Leu Gln Tyr Asn Gly Ser Trp Tyr Tyr Leu Asn
    770                 775                 780

Ala Asn Gly Asp Met Ala Thr Gly Trp Phe Gln Tyr Asn Gly Ser Trp
785                 790                 795                 800

Tyr Tyr Leu Asn Ala Asn Gly Asp Met Ala Thr Gly Trp Phe Gln Tyr
                805                 810                 815

Asn Gly Ser Trp Tyr Tyr Leu Asn Ala Asn Gly Asp Met Ala Thr Gly
            820                 825                 830

Trp Leu Gln Tyr Asn Gly Ser Trp Tyr Tyr Leu Asn Ser Asn Gly Ala
        835                 840                 845

Met Val Thr Gly Trp Leu Gln Asn Asn Gly Ser Trp Tyr Tyr Leu Asn
    850                 855                 860

Ala Asn Gly Ser Met Ala Thr Asp Trp Val Lys Asp Gly Asp Thr Trp
865                 870                 875                 880

Tyr Tyr Leu Glu Ala Ser Gly Ala Met Lys Ala Ser Gln Trp Phe Lys
```

```
                885                 890                 895

Val Ser Asp Asn Trp Tyr Tyr Val Asn Gly Ser Gly Ala Leu Ala Val
            900                 905                 910

Asn Thr Thr Val Asp Ser Tyr Arg Val Asn Pro Asn Gly Glu Trp Val
        915                 920                 925

Asn


<210> SEQ ID NO 31
<211> LENGTH: 579
<212> TYPE: PRT
<213> ORGANISM: Streptococcus pneumoniae

<400> SEQUENCE: 31

Met Phe Ala Ser Lys Ser Glu Arg Lys Val His Tyr Ser Ile Arg Lys
1               5                   10                  15

Phe Ser Ile Gly Val Ala Ser Val Val Val Ala Ser Leu Val Met Gly
            20                  25                  30

Ser Val Val His Ala Thr Glu Asn Glu Gly Ser Thr Gln Ala Ala Thr
        35                  40                  45

Phe Ser Asn Met Ala Asn Lys Ser Gln Thr Glu Gln Gly Glu Ile Asn
    50                  55                  60

Ile Glu Arg Asp Lys Ala Lys Thr Ala Val Ser Glu Tyr Lys Glu Lys
65                  70                  75                  80

Lys Val Ser Glu Ile Tyr Thr Lys Leu Glu Arg Asp Arg His Lys Asp
                85                  90                  95

Thr Val Asp Leu Val Asn Lys Leu Gln Glu Ile Lys Asn Glu Tyr Leu
            100                 105                 110

Asn Lys Ile Val Gln Ser Thr Ser Lys Thr Glu Ile Gln Gly Leu Ile
        115                 120                 125

Thr Thr Ser Arg Ser Lys Leu Asp Glu Ala Val Ser Lys Tyr Lys Lys
    130                 135                 140

Ala Pro Ser Ser Ser Ser Ser Ser Gly Ser Ser Thr Lys Pro Glu Ala
145                 150                 155                 160

Ser Asp Thr Ala Lys Pro Asn Lys Pro Thr Glu Leu Glu Lys Lys Val
                165                 170                 175

Ala Glu Ala Glu Lys Lys Val Glu Glu Ala Lys Lys Lys Ala Lys Asp
            180                 185                 190

Gln Lys Glu Glu Asp Tyr Arg Asn Tyr Pro Thr Ile Thr Tyr Lys Thr
        195                 200                 205

Leu Glu Leu Glu Ile Ala Glu Ser Asp Val Glu Val Lys Lys Ala Glu
    210                 215                 220

Leu Glu Leu Val Lys Glu Glu Ala Lys Glu Pro Arg Asn Glu Glu Lys
225                 230                 235                 240

Val Lys Gln Ala Lys Ala Lys Val Glu Ser Glu Glu Thr Glu Ala Thr
                245                 250                 255

Arg Leu Glu Lys Ile Lys Thr Asp Arg Lys Lys Ala Glu Glu Glu Ala
            260                 265                 270

Lys Arg Lys Ala Ala Glu Glu Asp Lys Val Lys Glu Lys Pro Ala Glu
        275                 280                 285

Gln Pro Lys Pro Ala Pro Ala Pro Gln Pro Glu Lys Pro Ala Pro Lys
    290                 295                 300

Pro Glu Asn Pro Ala Pro Lys Pro Glu Asn Pro Ala Pro Lys Pro Glu
305                 310                 315                 320

Lys Pro Ala Glu Gln Gln Ala Glu Glu Asp Tyr Ala Arg Arg Ser Glu
```

```
                325                 330                 335

Glu Glu Tyr Asn Arg Leu Thr Gln Gln Gln Pro Pro Lys Thr Glu Lys
            340                 345                 350

Pro Ala Gln Pro Ser Thr Pro Lys Thr Gly Trp Lys Gln Glu Asn Gly
        355                 360                 365

Met Trp Tyr Phe Tyr Asn Thr Asp Gly Ser Met Ala Thr Gly Trp Leu
    370                 375                 380

Gln Asn Asn Gly Ser Trp Tyr Tyr Leu Asn Ser Asn Gly Ala Met Ala
385                 390                 395                 400

Thr Gly Trp Leu Gln Asn Asn Gly Ser Trp Tyr Tyr Leu Asn Ala Asn
                405                 410                 415

Gly Ser Met Ala Thr Gly Trp Leu Gln Asn Asn Gly Ser Trp Tyr Tyr
            420                 425                 430

Leu Asn Ala Asn Gly Ser Met Ala Thr Gly Trp Leu Gln Tyr Asn Gly
        435                 440                 445

Ser Trp Tyr Tyr Leu Asn Ala Asn Gly Asp Met Ala Thr Gly Trp Leu
    450                 455                 460

Gln Tyr Asn Gly Ser Trp Tyr Tyr Leu Asn Ala Asn Gly Asp Met Ala
465                 470                 475                 480

Thr Gly Trp Leu Gln Tyr Asn Gly Ser Trp Tyr Tyr Leu Asn Ala Asn
                485                 490                 495

Gly Asp Met Ala Thr Gly Trp Leu Gln Tyr Asn Gly Ser Trp Tyr Tyr
            500                 505                 510

Leu Asn Ala Asn Gly Asp Met Ala Thr Gly Trp Val Lys Asp Gly Asp
        515                 520                 525

Thr Trp Tyr Tyr Leu Glu Ala Ser Gly Ala Met Lys Ala Ser Gln Trp
    530                 535                 540

Phe Lys Val Ser Asp Lys Trp Tyr Tyr Val Asn Gly Ser Gly Ala Leu
545                 550                 555                 560

Ala Val Asn Thr Thr Val Asp Gly Tyr Gly Val Asn Ala Asn Gly Glu
                565                 570                 575

Trp Val Asn


<210> SEQ ID NO 32
<211> LENGTH: 693
<212> TYPE: PRT
<213> ORGANISM: Streptococcus pneumoniae

<400> SEQUENCE: 32

Met Phe Ala Ser Lys Ser Glu Arg Lys Val His Tyr Ser Ile Arg Lys
1               5                   10                  15

Phe Ser Val Gly Val Ala Ser Val Val Val Ala Ser Leu Val Met Gly
            20                  25                  30

Ser Val Val His Ala Thr Glu Asn Glu Gly Ala Thr Gln Val Pro Thr
        35                  40                  45

Ser Ser Asn Arg Ala Asn Glu Ser Gln Ala Glu Gln Gly Glu Gln Pro
    50                  55                  60

Lys Lys Leu Asp Ser Glu Arg Asp Lys Ala Arg Lys Glu Val Glu Glu
65                  70                  75                  80

Tyr Val Lys Lys Ile Val Gly Glu Ser Tyr Ala Lys Ser Thr Lys Lys
                85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
```

```
        115                 120                 125

Gln Ile Leu Met Met Glu Ser Arg Ser Lys Val Asp Glu Ala Val Ser
    130                 135                 140

Lys Phe Glu Lys Asp Ser Ser Ser Ser Ser Ser Ser Asp Ser Ser Thr
145                 150                 155                 160

Lys Pro Glu Ala Ser Asp Thr Ala Lys Pro Asn Lys Pro Thr Glu Pro
                165                 170                 175

Gly Glu Lys Val Ala Glu Ala Lys Lys Lys Val Glu Glu Ala Glu Lys
            180                 185                 190

Lys Ala Lys Asp Gln Lys Glu Glu Asp Arg Arg Asn Tyr Pro Thr Ile
        195                 200                 205

Thr Tyr Lys Thr Leu Glu Leu Glu Ile Ala Glu Ser Asp Val Glu Val
    210                 215                 220

Lys Lys Ala Glu Leu Glu Leu Val Lys Val Lys Ala Asn Glu Pro Arg
225                 230                 235                 240

Asp Glu Gln Lys Ile Lys Gln Ala Glu Ala Glu Val Glu Ser Lys Gln
                245                 250                 255

Ala Glu Ala Thr Arg Leu Lys Lys Ile Lys Thr Asp Arg Glu Glu Ala
            260                 265                 270

Glu Glu Glu Ala Lys Arg Arg Ala Asp Ala Lys Glu Gln Gly Lys Pro
        275                 280                 285

Lys Gly Arg Ala Lys Arg Gly Val Pro Gly Glu Leu Ala Thr Pro Asp
    290                 295                 300

Lys Lys Glu Asn Asp Ala Lys Ser Ser Asp Ser Ser Val Gly Glu Glu
305                 310                 315                 320

Thr Leu Pro Ser Pro Ser Leu Lys Pro Glu Lys Lys Val Ala Glu Ala
                325                 330                 335

Glu Lys Lys Val Glu Glu Ala Lys Lys Lys Ala Glu Asp Gln Lys Glu
            340                 345                 350

Glu Asp Arg Arg Asn Tyr Pro Thr Ile Thr Tyr Lys Thr Leu Glu Leu
        355                 360                 365

Glu Ile Ala Glu Ser Asp Val Glu Val Lys Lys Ala Glu Leu Glu Leu
    370                 375                 380

Val Lys Glu Glu Ala Lys Glu Pro Arg Asn Glu Glu Lys Val Lys Gln
385                 390                 395                 400

Ala Lys Ala Glu Val Glu Ser Lys Lys Ala Glu Ala Thr Arg Leu Glu
                405                 410                 415

Lys Ile Lys Thr Asp Arg Lys Lys Ala Glu Glu Glu Ala Lys Arg Lys
            420                 425                 430

Ala Ala Glu Glu Asp Lys Val Lys Glu Lys Pro Ala Glu Gln Pro Gln
        435                 440                 445

Pro Ala Pro Ala Pro Lys Ala Glu Lys Pro Ala Pro Ala Pro Lys Pro
    450                 455                 460

Glu Asn Pro Ala Glu Gln Pro Lys Ala Glu Lys Pro Ala Asp Gln Gln
465                 470                 475                 480

Ala Glu Glu Asp Tyr Ala Arg Arg Ser Glu Glu Glu Tyr Asn Arg Leu
                485                 490                 495

Thr Gln Gln Gln Pro Pro Lys Thr Glu Lys Pro Ala Gln Pro Ser Thr
            500                 505                 510

Pro Lys Thr Gly Trp Lys Gln Glu Asn Gly Met Trp Tyr Phe Tyr Asn
        515                 520                 525

Thr Asp Gly Ser Met Ala Thr Gly Trp Leu Gln Asn Asn Gly Ser Trp
    530                 535                 540
```

```
Tyr Tyr Leu Asn Ser Asn Gly Ala Met Ala Thr Gly Trp Leu Gln Asn
545                 550                 555                 560

Asn Gly Ser Trp Tyr Tyr Leu Asn Ala Asn Gly Ser Met Ala Thr Gly
                565                 570                 575

Trp Leu Gln Asn Asn Gly Ser Trp Tyr Tyr Leu Asn Ala Asn Gly Ser
            580                 585                 590

Met Ala Thr Gly Trp Leu Gln Tyr Asn Gly Ser Trp Tyr Tyr Leu Asn
        595                 600                 605

Ala Asn Gly Asp Met Ala Thr Gly Trp Leu Gln Tyr Asn Gly Ser Trp
    610                 615                 620

Tyr Tyr Leu Asn Ala Asn Gly Asp Met Ala Thr Gly Trp Val Lys Asp
625                 630                 635                 640

Gly Asp Thr Trp Tyr Tyr Leu Glu Ala Ser Gly Ala Met Lys Ala Ser
                645                 650                 655

Gln Trp Phe Lys Val Ser Asp Lys Trp Tyr Tyr Val Asn Gly Ser Gly
            660                 665                 670

Ala Leu Ala Val Asn Thr Thr Val Asp Gly Tyr Gly Val Asn Ala Asn
        675                 680                 685

Gly Glu Trp Val Asn
    690
```

<210> SEQ ID NO 33
<211> LENGTH: 701
<212> TYPE: PRT
<213> ORGANISM: Streptococcus pneumoniae

<400> SEQUENCE: 33

```
Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Val Met Gly
            20                  25                  30

Ser Val Val His Ala Thr Glu Asn Glu Gly Ser Thr Gln Ala Ala Thr
        35                  40                  45

Ser Ser Asn Met Ala Lys Thr Glu His Arg Lys Ala Ala Lys Gln Val
    50                  55                  60

Val Asp Glu Tyr Ile Glu Lys Met Leu Arg Glu Ile Gln Leu Asp Arg
65                  70                  75                  80

Arg Lys His Thr Gln Asn Val Ala Leu Asn Ile Lys Leu Ser Ala Ile
                85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Ala Phe Glu
        115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
        195                 200                 205

Ala Lys Glu Lys Val Glu Ser Lys Lys Ala Glu Ala Thr Arg Leu Glu
```

```
    210                 215                 220

Asn Ile Lys Thr Asp Arg Lys Lys Ala Glu Glu Glu Ala Lys Arg Lys
225                 230                 235                 240

Ala Asp Ala Lys Leu Lys Glu Ala Asn Val Ala Thr Ser Asp Gln Gly
                245                 250                 255

Lys Pro Lys Gly Arg Ala Lys Arg Gly Val Pro Gly Glu Leu Ala Thr
            260                 265                 270

Pro Asp Lys Lys Glu Asn Asp Ala Lys Ser Ser Asp Ser Ser Val Gly
        275                 280                 285

Glu Glu Thr Leu Pro Ser Ser Ser Leu Lys Ser Gly Lys Lys Val Ala
    290                 295                 300

Glu Ala Glu Lys Lys Val Glu Glu Ala Glu Lys Lys Ala Lys Asp Gln
305                 310                 315                 320

Lys Glu Glu Asp Arg Arg Asn Tyr Pro Thr Asn Thr Tyr Lys Thr Leu
                325                 330                 335

Asp Leu Glu Ile Ala Glu Ser Asp Val Lys Val Lys Glu Ala Glu Leu
            340                 345                 350

Glu Leu Val Lys Glu Glu Ala Lys Glu Pro Arg Asp Glu Glu Lys Ile
        355                 360                 365

Lys Gln Ala Lys Ala Lys Val Glu Ser Lys Lys Ala Glu Ala Thr Arg
    370                 375                 380

Leu Glu Asn Ile Lys Thr Asp Arg Lys Lys Ala Glu Glu Glu Ala Lys
385                 390                 395                 400

Arg Lys Ala Ala Glu Glu Asp Lys Val Lys Glu Lys Pro Ala Glu Gln
                405                 410                 415

Pro Gln Pro Ala Pro Ala Thr Gln Pro Glu Lys Pro Ala Pro Lys Pro
            420                 425                 430

Glu Lys Pro Ala Glu Gln Pro Lys Ala Glu Lys Thr Asp Asp Gln Gln
        435                 440                 445

Ala Glu Glu Asp Tyr Ala Arg Arg Ser Glu Glu Glu Tyr Asn Arg Leu
    450                 455                 460

Thr Gln Gln Gln Pro Pro Lys Thr Glu Lys Pro Ala Gln Pro Ser Thr
465                 470                 475                 480

Pro Lys Thr Gly Trp Lys Gln Glu Asn Gly Met Trp Tyr Phe Tyr Asn
                485                 490                 495

Thr Asp Gly Ser Met Ala Thr Gly Trp Leu Gln Asn Asn Gly Ser Trp
            500                 505                 510

Tyr Tyr Leu Asn Ala Asn Gly Ala Met Ala Thr Gly Trp Leu Gln Asn
        515                 520                 525

Asn Gly Ser Trp Tyr Tyr Leu Asn Ala Asn Gly Ser Met Ala Thr Gly
    530                 535                 540

Trp Leu Gln Asn Asn Gly Ser Trp Tyr Tyr Leu Asn Ala Asn Gly Ala
545                 550                 555                 560

Met Ala Thr Gly Trp Leu Gln Tyr Asn Gly Ser Trp Tyr Tyr Leu Asn
                565                 570                 575

Ser Asn Gly Ala Met Ala Thr Gly Trp Leu Gln Tyr Asn Gly Ser Trp
            580                 585                 590

Tyr Tyr Leu Asn Ala Asn Gly Asp Met Ala Thr Gly Trp Leu Gln Asn
        595                 600                 605

Asn Gly Ser Trp Tyr Tyr Leu Asn Ala Asn Gly Asp Met Ala Thr Gly
    610                 615                 620

Trp Leu Gln Tyr Asn Gly Ser Trp Tyr Tyr Leu Asn Ala Asn Gly Asp
625                 630                 635                 640
```

```
Met Ala Thr Gly Trp Val Lys Asp Gly Asp Thr Trp Tyr Tyr Leu Glu
                645                 650                 655

Ala Ser Gly Ala Met Lys Ala Ser Gln Trp Phe Lys Val Ser Asp Lys
            660                 665                 670

Trp Tyr Tyr Val Asn Gly Ser Gly Ala Leu Ala Val Asn Thr Thr Val
        675                 680                 685

Asp Gly Tyr Gly Val Asn Ala Asn Gly Glu Trp Val Asn
    690                 695                 700


<210> SEQ ID NO 34
<211> LENGTH: 693
<212> TYPE: PRT
<213> ORGANISM: Streptococcus pneumoniae

<400> SEQUENCE: 34

Met Phe Ala Ser Lys Ser Glu Arg Lys Val His Tyr Ser Ile Arg Lys
1               5                   10                  15

Phe Ser Val Gly Val Ala Ser Val Val Val Ala Ser Leu Val Met Gly
            20                  25                  30

Ser Val Val His Ala Thr Glu Asn Glu Gly Ala Thr Gln Val Pro Thr
        35                  40                  45

Ser Ser Asn Arg Ala Asn Glu Ser Gln Ala Glu Gln Gly Glu Gln Pro
    50                  55                  60

Lys Lys Leu Asp Ser Glu Arg Asp Lys Ala Arg Lys Glu Val Glu Glu
65                  70                  75                  80

Tyr Val Lys Lys Ile Val Gly Glu Ser Tyr Ala Lys Ser Thr Lys Lys
                85                  90                  95

Arg His Thr Ile Thr Val Ala Leu Val Asn Glu Leu Asn Asn Ile Lys
            100                 105                 110

Asn Glu Tyr Leu Asn Lys Ile Val Glu Ser Thr Ser Glu Ser Gln Leu
        115                 120                 125

Gln Ile Leu Met Met Glu Ser Arg Ser Lys Val Asp Glu Ala Val Ser
    130                 135                 140

Lys Phe Glu Lys Asp Ser Ser Ser Ser Ser Ser Ser Asp Ser Ser Thr
145                 150                 155                 160

Lys Pro Glu Ala Ser Asp Thr Ala Lys Pro Asn Lys Pro Thr Glu Pro
                165                 170                 175

Gly Glu Lys Val Ala Glu Ala Lys Lys Lys Val Glu Glu Ala Glu Lys
            180                 185                 190

Lys Ala Lys Asp Gln Lys Glu Glu Asp Arg Arg Asn Tyr Pro Thr Ile
        195                 200                 205

Thr Tyr Lys Thr Leu Glu Leu Glu Ile Ala Glu Ser Asp Val Glu Val
    210                 215                 220

Lys Lys Ala Glu Leu Glu Leu Val Lys Val Lys Ala Asn Glu Pro Arg
225                 230                 235                 240

Asp Glu Gln Lys Ile Lys Gln Ala Glu Ala Glu Val Glu Ser Lys Gln
                245                 250                 255

Ala Glu Ala Thr Arg Leu Lys Lys Ile Lys Thr Asp Arg Glu Glu Ala
            260                 265                 270

Glu Glu Glu Ala Lys Arg Arg Ala Asp Ala Lys Glu Gln Gly Lys Pro
        275                 280                 285

Lys Gly Arg Ala Lys Arg Gly Val Pro Gly Glu Leu Ala Thr Pro Asp
    290                 295                 300

Lys Lys Glu Asn Asp Ala Lys Ser Ser Asp Ser Ser Val Gly Glu Glu
```

```
305                 310                 315                 320

Thr Leu Pro Ser Pro Ser Leu Lys Pro Glu Lys Lys Val Ala Glu Ala
                325                 330                 335

Glu Lys Lys Val Glu Glu Ala Lys Lys Lys Ala Glu Asp Gln Lys Glu
            340                 345                 350

Glu Asp Arg Arg Asn Tyr Pro Thr Asn Thr Tyr Lys Thr Leu Glu Leu
        355                 360                 365

Glu Ile Ala Glu Ser Asp Val Glu Val Lys Lys Ala Glu Leu Glu Leu
    370                 375                 380

Val Lys Glu Glu Ala Lys Glu Pro Arg Asn Glu Glu Lys Val Lys Gln
385                 390                 395                 400

Ala Lys Ala Glu Val Glu Ser Lys Lys Ala Glu Ala Thr Arg Leu Glu
                405                 410                 415

Lys Ile Lys Thr Asp Arg Lys Lys Ala Glu Glu Glu Ala Lys Arg Lys
            420                 425                 430

Ala Ala Glu Glu Asp Lys Val Lys Glu Lys Pro Ala Glu Gln Pro Gln
        435                 440                 445

Pro Ala Pro Ala Pro Lys Ala Glu Lys Pro Ala Pro Ala Pro Lys Pro
    450                 455                 460

Glu Asn Pro Ala Glu Gln Pro Lys Ala Glu Lys Pro Ala Asp Gln Gln
465                 470                 475                 480

Ala Glu Glu Asp Tyr Ala Arg Arg Ser Glu Glu Glu Tyr Asn Arg Leu
                485                 490                 495

Thr Gln Gln Gln Pro Pro Lys Thr Glu Lys Pro Ala Gln Pro Ser Thr
            500                 505                 510

Pro Lys Thr Gly Trp Lys Gln Glu Asn Gly Met Trp Tyr Phe Tyr Asn
        515                 520                 525

Thr Asp Gly Ser Met Ala Thr Gly Trp Leu Gln Asn Asn Gly Ser Trp
    530                 535                 540

Tyr Tyr Leu Asn Ser Asn Gly Ala Met Ala Thr Gly Trp Leu Gln Asn
545                 550                 555                 560

Asn Gly Ser Trp Tyr Tyr Leu Asn Ala Asn Gly Ser Met Ala Thr Gly
                565                 570                 575

Trp Leu Gln Asn Asn Gly Ser Trp Tyr Tyr Leu Asn Ala Asn Gly Ser
            580                 585                 590

Met Ala Thr Gly Trp Leu Gln Tyr Asn Gly Ser Trp Tyr Tyr Leu Asn
        595                 600                 605

Ala Asn Gly Ser Met Ala Thr Gly Trp Leu Gln Tyr Asn Gly Ser Trp
    610                 615                 620

Tyr Tyr Leu Asn Ala Asn Gly Asp Met Ala Thr Gly Trp Val Lys Asp
625                 630                 635                 640

Gly Asp Thr Trp Tyr Tyr Leu Glu Ala Ser Gly Ala Met Lys Ala Ser
                645                 650                 655

Gln Trp Phe Lys Val Ser Asp Lys Trp Tyr Tyr Val Asn Gly Ser Gly
            660                 665                 670

Ala Leu Ala Val Asn Thr Thr Val Asp Gly Tyr Gly Val Asn Ala Asn
        675                 680                 685

Gly Glu Trp Val Asn
    690
```

<210> SEQ ID NO 35
<211> LENGTH: 866
<212> TYPE: PRT
<213> ORGANISM: Streptococcus pneumoniae

<400> SEQUENCE: 35

```
Met Phe Ala Ser Lys Ser Glu Arg Lys Val His Tyr Ser Ile Arg Lys
1               5                   10                  15

Phe Ser Ile Gly Val Ala Ser Val Val Val Ala Ser Leu Phe Leu Gly
            20                  25                  30

Gly Val Val His Ala Glu Glu Val Arg Arg Gly Asn Asn Leu Thr Val
        35                  40                  45

Thr Ser Ser Gly Asp Glu Val Glu Ser His Tyr Gln Ser Ile Leu Glu
    50                  55                  60

Lys Val Arg Lys Ser Leu Glu Lys Asp Arg His Thr Gln Asn Val Asp
65                  70                  75                  80

Leu Ile Lys Lys Leu Gln Asp Ile Lys Arg Thr Tyr Leu Tyr Asn Leu
                85                  90                  95

Lys Glu Lys Pro Glu Ala Glu Leu Thr Ser Lys Thr Lys Lys Glu Leu
            100                 105                 110

Asp Ala Ala Phe Glu Lys Phe Lys Lys Glu Pro Glu Leu Thr Lys Lys
        115                 120                 125

Leu Ala Glu Ala Glu Lys Lys Ala Lys Asp Gln Lys Glu Glu Asp His
    130                 135                 140

Arg Asn Tyr Pro Thr Asn Thr Tyr Lys Thr Ile Glu Leu Glu Ile Ala
145                 150                 155                 160

Glu Ala Glu Val Gly Val Ala Lys Ala Glu Leu Glu Leu Ala Gln Ala
                165                 170                 175

Gln Val Gln Ile Pro Gln Asp Thr Glu Lys Ile Asn Ala Ala Lys Ala
            180                 185                 190

Lys Val Glu Ala Ala Lys Ser Asn Val Lys Lys Leu Glu Lys Ile Lys
        195                 200                 205

Ser Asp Ile Glu Lys Thr Tyr Leu Tyr Lys Leu Asp Asn Ser Thr Lys
    210                 215                 220

Glu Thr Pro Lys Pro Arg Val Arg Arg Asn Ser Pro Glu Ile Lys Ala
225                 230                 235                 240

Lys Gly Arg Val Lys Asn Tyr Lys Glu Ala Asn Ile Glu Leu Ser Lys
                245                 250                 255

Tyr Met Thr Asp Leu Tyr Lys Leu Asp Asn Ser Thr Lys Glu Thr Pro
            260                 265                 270

Lys Ser Arg Val Arg Arg Asn Ser Pro Gln Val Gly Asp Ser Arg Glu
        275                 280                 285

Leu Lys Glu Thr Ile Asp Lys Ala Lys Lys Thr Leu Ser Thr Tyr Met
    290                 295                 300

Val Thr Arg Leu Thr Lys Leu Asp Pro Ser Val Phe Trp Phe Ala Asp
305                 310                 315                 320

Leu Leu Met Asp Ala Lys Lys Val Val Glu Glu Tyr Lys Thr Lys Leu
                325                 330                 335

Glu Asp Ala Ser Asp Gln Lys Ser Val Glu Asp Leu Arg Lys Glu Ala
            340                 345                 350

Glu Gly Lys Ile Glu Ser Leu Ile Val Thr His Gln Asn Arg Glu Lys
        355                 360                 365

Glu Asn Gln Pro Ala Pro Gln Pro Gly Gly Gln Ala Gly Gly Ser Met
    370                 375                 380

Val Val Pro Pro Val Thr Gln Thr Pro Pro Ser Thr Ser Gln Ser Pro
385                 390                 395                 400

Gly Gln Lys Ala Thr Glu Ala Glu Lys Lys Lys Leu Gln Asp Leu Ile
```

```
                405                 410                 415

Arg Gln Phe Gln Glu Ala Leu Asn Lys Leu Asp Asp Glu Thr Lys Thr
            420                 425                 430

Val Pro Asp Gly Gly Lys Leu Thr Gly Glu Ala Trp Lys Ala Tyr Asn
        435                 440                 445

Glu Thr Arg Thr Tyr Ala Lys Glu Val Val Asp Lys Ser Lys Lys Leu
    450                 455                 460

Leu Ser Gln Thr Ala Val Thr Met Asp Glu Leu Ala Met Gln Leu Thr
465                 470                 475                 480

Lys Leu Asn Asp Ala Met Ser Lys Leu Lys Glu Ala Lys Ala Lys Leu
                485                 490                 495

Val Pro Glu Val Lys Pro Gln Pro Glu Asn Pro Glu Pro Lys Pro Gln
            500                 505                 510

Pro Glu Gly Glu Lys Pro Ser Val Pro Asp Ile Asn Gln Glu Lys Glu
        515                 520                 525

Lys Ala Lys Leu Ala Ile Ala Thr Tyr Met Ser Lys Ile Leu Asp Asp
    530                 535                 540

Ile Lys Lys His His Leu Lys Lys Glu Lys His His Gln Ile Val Ala
545                 550                 555                 560

Leu Ile Lys Asp Leu Asp Lys Leu Lys Lys Gln Ala Leu Ser Glu Ile
                565                 570                 575

Asp Asn Val Asn Thr Lys Val Glu Ile Glu Asn Thr Val His Lys Val
            580                 585                 590

Phe Ala Ala Met Asp Thr Val Val Thr Asn Ser Lys Lys Ala Leu Ile
        595                 600                 605

Gln Asn Thr Pro Gln Val Pro Glu Ala Pro Lys Ser Pro Glu Val Pro
    610                 615                 620

Lys Val Ser Asp Thr Pro Lys Ala Pro Asp Thr Pro Gln Val Pro Glu
625                 630                 635                 640

Ala Pro Lys Ala Pro Asp Thr Pro Gln Ile Pro Glu Ala Pro Ala Pro
                645                 650                 655

Glu Thr Pro Ala Pro Ala Pro Glu Ala Pro Lys Thr Gly Trp Lys Gln
            660                 665                 670

Glu Asn Gly Met Trp Tyr Phe Tyr Asn Thr Asp Gly Ser Met Ala Thr
        675                 680                 685

Gly Trp Leu Glu Tyr Asn Gly Ser Trp Tyr Tyr Leu Asn Ala Asn Gly
    690                 695                 700

Ala Met Ala Thr Gly Trp Leu Glu Tyr Asn Gly Ser Trp Tyr Tyr Leu
705                 710                 715                 720

Asn Thr Asn Gly Ala Met Glu Thr Gly Trp Leu Glu Tyr Asn Gly Ser
                725                 730                 735

Trp Tyr Tyr Leu Asn Thr Asn Gly Ala Met Glu Thr Gly Trp Leu Glu
            740                 745                 750

Tyr Asn Gly Ser Trp Tyr Tyr Leu Asn Thr Asn Gly Ala Met Glu Thr
        755                 760                 765

Gly Trp Leu Glu Tyr Asn Gly Ser Trp Tyr Tyr Leu Asn Thr Asn Gly
    770                 775                 780

Ala Met Glu Thr Gly Trp Leu Glu Tyr Asn Gly Ser Trp Tyr Tyr Leu
785                 790                 795                 800

Asn Ala Asn Gly Ser Met Ala Thr Gly Trp Leu Lys Asp Gly Asp Thr
                805                 810                 815

Trp Tyr Tyr Leu Glu Ala Ser Gly Ala Met Lys Glu Ser Gln Trp Phe
            820                 825                 830
```

```
Lys Val Ser Asp Lys Trp Tyr Tyr Val Asn Gly Ser Gly Ala Leu Ala
        835                 840                 845

Val Asn Thr Thr Val Asp Gly Tyr Gly Val Asn Ala Asn Gly Lys Trp
    850                 855                 860

Val Asn
865


<210> SEQ ID NO 36
<211> LENGTH: 869
<212> TYPE: PRT
<213> ORGANISM: Streptococcus pneumoniae

<400> SEQUENCE: 36

Met Phe Ala Ser Lys Ser Glu Arg Lys Val His Tyr Ser Ile Arg Lys
1               5                   10                  15

Phe Ser Ile Gly Val Ala Ser Val Val Val Ala Ser Leu Val Met Gly
            20                  25                  30

Ser Val Val His Ala Thr Glu Asn Glu Gly Ile Thr Gln Val Pro Thr
        35                  40                  45

Ser Tyr Asn Lys Ala Asn Glu Ser Gln Thr Glu His Arg Lys Ala Ala
    50                  55                  60

Lys Gln Val Asp Glu Asp Ile Lys Lys Met Leu Ser Glu Ile Gln Glu
65                  70                  75                  80

Tyr Ile Lys Lys Met Leu Ser Glu Ile Gln Leu Asp Lys Arg Lys Asp
                85                  90                  95

Thr Gln Asn Arg Thr Leu Asn Arg Lys Leu Ser Ala Ile Gln Thr Lys
            100                 105                 110

Tyr Leu Tyr Glu Leu Arg Val Leu Lys Glu Lys Ser Lys Lys Glu Glu
        115                 120                 125

Leu Thr Ser Lys Thr Lys Lys Glu Leu Asp Ala Ala Phe Glu Lys Phe
    130                 135                 140

Lys Lys Glu Pro Glu Leu Thr Lys Lys Leu Ala Glu Ala Lys Gln Lys
145                 150                 155                 160

Ala Lys Ala Gln Lys Glu Glu Asp Phe Arg Asn Tyr Pro Thr Asn Thr
                165                 170                 175

Tyr Lys Thr Leu Glu Leu Glu Ile Ala Glu Phe Asp Val Lys Val Lys
            180                 185                 190

Glu Ala Asp Leu Glu Leu Val Lys Glu Glu Ala Lys Pro Arg Asn Glu
        195                 200                 205

Glu Lys Ile Lys Gln Ala Lys Ala Lys Val Glu Ser Lys Lys Ala Glu
    210                 215                 220

Ala Thr Arg Leu Glu Glu Ile Lys Thr Glu Arg Lys Arg Ala Glu Glu
225                 230                 235                 240

Glu Ala Lys Arg Lys Ala Gly Glu Ser Glu Glu Lys Ala Ala Glu Ala
                245                 250                 255

Asn Gln Lys Val Asp Thr Lys Glu Gln Gly Lys Pro Lys Arg Arg Ala
            260                 265                 270

Lys Arg Gly Val Ser Gly Glu Leu Ala Thr Pro Asp Lys Lys Glu Asn
        275                 280                 285

Asp Ala Lys Ser Ser Asp Ser Ser Val Gly Glu Glu Thr Leu Pro Ser
    290                 295                 300

Pro Ser Leu Asn Met Ala Asn Glu Ser Gln Thr Glu His Arg Lys Asp
305                 310                 315                 320

Val Asp Glu Tyr Ile Lys Lys Met Leu Ser Gly Ile Gln Leu Asp Arg
```

```
                325                 330                 335

Arg Lys Gln Thr Gln Asn Val Asn Leu Asn Ile Lys Leu Ser Ala Ile
            340                 345                 350

Lys Thr Lys Tyr Leu Tyr Glu Leu Ser Val Leu Lys Glu Asn Ser Lys
        355                 360                 365

Lys Glu Glu Leu Thr Ser Lys Thr Lys Ala Glu Leu Thr Ala Ala Phe
    370                 375                 380

Glu Gln Phe Lys Lys Asp Thr Leu Lys Pro Glu Lys Lys Val Ala Glu
385                 390                 395                 400

Ala Glu Lys Lys Val Glu Glu Ala Lys Lys Lys Ala Lys Asp Gln Lys
                405                 410                 415

Glu Glu Asp Arg Arg Asn Tyr Pro Thr Asn Thr Tyr Lys Thr Leu Glu
            420                 425                 430

Leu Glu Ile Ala Glu Ser Asp Val Lys Val Lys Glu Ala Glu Leu Glu
        435                 440                 445

Leu Val Lys Glu Glu Ala Asn Glu Ser Arg Asn Glu Glu Lys Ile Lys
    450                 455                 460

Gln Ala Lys Glu Lys Val Glu Ser Lys Lys Ala Glu Ala Thr Arg Leu
465                 470                 475                 480

Glu Lys Ile Lys Thr Asp Arg Lys Lys Ala Glu Glu Glu Ala Lys Arg
                485                 490                 495

Lys Ala Glu Glu Ser Glu Lys Lys Ala Ala Glu Ala Lys Gln Lys Val
            500                 505                 510

Asp Ala Glu Glu Tyr Ala Leu Glu Ala Lys Ile Ala Glu Leu Glu Tyr
        515                 520                 525

Glu Val Gln Arg Leu Glu Lys Glu Leu Lys Glu Ile Asp Glu Ser Asp
    530                 535                 540

Ser Glu Asp Tyr Leu Lys Glu Gly Leu Arg Ala Pro Leu Gln Ser Lys
545                 550                 555                 560

Leu Asp Thr Lys Lys Ala Lys Leu Ser Lys Leu Glu Glu Leu Ser Asp
                565                 570                 575

Lys Ile Asp Glu Leu Asp Val Asn Cys Asn Leu Arg Ser Gln Leu Lys
            580                 585                 590

Asp Ala Glu Gly Asn Asn Asn Val Glu Ala Tyr Phe Lys Glu Gly Leu
        595                 600                 605

Glu Lys Thr Thr Ala Glu Lys Lys Ala Glu Leu Glu Lys Ala Glu Ala
    610                 615                 620

Asp Leu Lys Lys Ala Val Asp Glu Pro Glu Thr Pro Ala Pro Ala Pro
625                 630                 635                 640

Gln Pro Ala Pro Ala Pro Glu Lys Pro Ala Glu Lys Gln Ala Pro Ala
                645                 650                 655

Ser Ser Pro Glu Lys Pro Ala Pro Ala Pro Glu Lys Pro Gly Pro Ala
            660                 665                 670

Pro Glu Lys Pro Ala Pro Ala Pro Glu Lys Pro Ala Pro Thr Pro Glu
        675                 680                 685

Thr Pro Lys Thr Gly Trp Lys Gln Glu Asn Gly Met Trp Tyr Phe Tyr
    690                 695                 700

Asn Thr Asp Gly Ser Met Ala Thr Gly Trp Leu Gln Asn Asn Gly Ser
705                 710                 715                 720

Trp Tyr Tyr Leu Asn Ser Asn Gly Ala Met Ala Thr Gly Trp Leu Gln
                725                 730                 735

Asn Asn Gly Ser Trp Tyr Tyr Leu Asn Ser Asn Gly Ala Met Ala Thr
            740                 745                 750
```

```
Gly Trp Leu Gln Tyr Asn Gly Ser Trp Tyr Tyr Leu Asn Ala Asn Gly
        755                 760                 765

Asp Met Ala Thr Gly Trp Leu Gln Tyr Asn Gly Ser Trp Tyr Tyr Leu
    770                 775                 780

Asn Ala Asn Gly Asp Met Ala Thr Gly Trp Leu Gln Tyr Asn Gly Ser
785                 790                 795                 800

Trp Tyr Tyr Leu Asn Ala Asn Gly Asp Met Ala Thr Gly Trp Val Lys
                805                 810                 815

Asp Gly Asp Thr Trp Tyr Tyr Leu Glu Ala Ser Gly Ala Met Lys Ala
            820                 825                 830

Arg Trp Phe Lys Val Ser Asp Lys Trp Tyr Tyr Val Asn Gly Ser Gly
        835                 840                 845

Ala Leu Ala Val Asn Thr Thr Val Asp Ser Tyr Arg Val Asn Ala Asn
    850                 855                 860

Gly Glu Trp Val Asn
865
```

<210> SEQ ID NO 37
<211> LENGTH: 681
<212> TYPE: PRT
<213> ORGANISM: Streptococcus pneumoniae

<400> SEQUENCE: 37

```
Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Phe Leu Gly
            20                  25                  30

Gly Val Ala His Ala Glu Gly Val Arg Ile Gly Asn Asn Ser Thr Val
        35                  40                  45

Thr Ser Ser Gly Asp Glu Val Glu Ser His Leu Gln Ser Ile Leu Lys
    50                  55                  60

Asp Val Asn Lys Asn Leu Lys Lys Val Gln His Thr Gln Asn Val Gly
65                  70                  75                  80

Leu Leu Thr Lys Leu Ser Glu Ile Lys Arg Lys Tyr Leu Tyr Glu Leu
                85                  90                  95

Lys Val Asn Gly Leu Glu Glu Lys Ser Lys Ala Glu Leu Thr Ser Lys
            100                 105                 110

Thr Lys Lys Glu Leu Thr Ala Ala Phe Glu Gln Phe Lys Lys Asp Thr
        115                 120                 125

Leu Ser Thr Glu Leu Glu Lys Lys Val Ala Glu Ala Gln Lys Lys Val
    130                 135                 140

Ala Glu Ala Glu Lys Lys Ala Lys Ala Gln Lys Glu Glu Asp His Arg
145                 150                 155                 160

Asn Tyr Pro Thr Asn Thr Tyr Lys Thr Leu Glu Leu Glu Ile Ala Glu
                165                 170                 175

Ser Asp Val Glu Val Lys Lys Ala Glu Leu Glu Leu Leu Lys Glu Glu
            180                 185                 190

Ala Lys Glu Ser Arg Asp Glu Gly Thr Ile Lys Gln Ala Glu Ala Lys
        195                 200                 205

Val Glu Ser Lys Lys Ala Glu Ala Thr Lys Leu Glu Lys Ile Lys Thr
    210                 215                 220

Asp Arg Glu Lys Ala Glu Glu Glu Ala Lys Arg Arg Ala Asp Ala Lys
225                 230                 235                 240

Leu Gln Glu Ala Asn Val Ala Thr Ser Gly Gln Asp Lys Ser Lys Arg
```

```
                245                 250                 255

Arg Ala Lys Arg Ala Val Pro Gly Glu Pro Ala Thr Pro Asp Lys Lys
            260                 265                 270

Glu Asn Asp Ala Lys Ser Ser Asp Ser Ser Val Gly Glu Glu Thr Leu
        275                 280                 285

Pro Ser Pro Ser Leu Lys Pro Glu Lys Lys Val Ala Glu Ala Glu Lys
    290                 295                 300

Lys Val Glu Glu Ala Glu Lys Lys Ala Lys Asp Gln Lys Glu Glu Asp
305                 310                 315                 320

Arg Arg Asn Tyr Pro Thr Asn Thr Tyr Lys Thr Leu Glu Leu Glu Ile
                325                 330                 335

Ala Glu Ser Asp Val Lys Val Lys Glu Ala Glu Leu Glu Leu Val Lys
            340                 345                 350

Glu Glu Val Asn Glu Pro Arg Asn Glu Glu Lys Val Lys Gln Ala Lys
        355                 360                 365

Ala Glu Val Glu Ser Lys Lys Ala Glu Ala Thr Arg Leu Glu Lys Ile
    370                 375                 380

Lys Thr Asp Arg Lys Lys Ala Glu Glu Ala Lys Arg Lys Ala Ala Glu
385                 390                 395                 400

Glu Asp Lys Val Lys Glu Lys Pro Ala Pro Ala Pro Gln Pro Ala Pro
                405                 410                 415

Ala Pro Gln Pro Glu Lys Pro Ala Glu Glu Thr Pro Ala Pro Ala Pro
            420                 425                 430

Lys Pro Glu Lys Pro Thr Glu Gln Pro Lys Ala Glu Lys Pro Asp Asp
        435                 440                 445

Gln Gln Ala Glu Glu Asp Tyr Ala Arg Arg Ser Glu Glu Glu Tyr Asn
    450                 455                 460

Arg Leu Thr Gln Gln Gln Pro Pro Lys Pro Glu Gln Pro Ala Pro Ala
465                 470                 475                 480

Pro Lys Ile Gly Trp Lys Gln Glu Asn Gly Met Trp Tyr Phe Tyr Asn
                485                 490                 495

Thr Asp Gly Ser Met Ala Thr Gly Trp Leu Gln Asn Asn Gly Ser Trp
            500                 505                 510

Tyr Tyr Leu Asn Ala Asn Gly Ala Met Ala Thr Gly Trp Leu Gln Asn
        515                 520                 525

Asn Gly Ser Trp Tyr Tyr Leu Asn Ala Asn Gly Ser Met Ala Thr Gly
    530                 535                 540

Trp Leu Gln Tyr Asn Gly Ser Trp Tyr Tyr Leu Asn Ser Asn Gly Ala
545                 550                 555                 560

Met Ala Thr Gly Trp Leu Gln Asn Asn Gly Ser Trp Tyr Tyr Leu Asn
                565                 570                 575

Ala Asn Gly Ser Met Ala Thr Gly Trp Leu Gln Tyr Asn Gly Ser Trp
            580                 585                 590

Tyr Tyr Leu Asn Ser Asn Gly Ala Met Val Thr Gly Trp Leu Gln Asn
        595                 600                 605

Asn Gly Ser Trp Tyr Tyr Leu Asn Ala Asn Gly Ser Met Ala Thr Asp
    610                 615                 620

Trp Val Lys Asp Gly Asp Thr Trp Tyr Tyr Leu Glu Ala Ser Gly Ala
625                 630                 635                 640

Met Lys Ala Ser Gln Trp Phe Lys Val Ser Asp Lys Trp Tyr Tyr Val
                645                 650                 655

Asn Gly Ser Gly Ala Leu Ala Val Asn Thr Thr Val Asp Ser Tyr Arg
            660                 665                 670
```

```
Val Asn Ala Asn Gly Glu Trp Val Asn
        675                 680


<210> SEQ ID NO 38
<211> LENGTH: 769
<212> TYPE: PRT
<213> ORGANISM: Streptococcus pneumoniae

<400> SEQUENCE: 38

Met Phe Lys Ser Asn Tyr Glu Arg Lys Met Cys Tyr Ser Ile Arg Lys
1               5                   10                  15

Phe Ser Ile Gly Val Ala Ser Val Ala Val Ala Ser Leu Val Met Gly
            20                  25                  30

Ser Val Val His Ala Thr Glu Asn Glu Gly Thr Thr Gln Ala Pro Thr
        35                  40                  45

Ser Ser Asn Arg Gly Asn Glu Ser Gln Ala Glu Gln Arg Arg Glu Leu
    50                  55                  60

Asp Leu Glu Arg Asp Lys Val Lys Lys Glu Val Arg Glu Tyr Lys Glu
65                  70                  75                  80

Lys Lys Val Lys Glu Leu Tyr Ser Lys Ser Thr Lys Ser Arg His Lys
                85                  90                  95

Lys Thr Val Asp Ile Val Asn Lys Leu Gln Asn Ile Asn Asn Glu Tyr
            100                 105                 110

Leu Asn Lys Ile Ile Gln Ser Thr Ser Thr Tyr Glu Glu Leu Gln Lys
        115                 120                 125

Leu Met Met Glu Ser Gln Ser Glu Val Asp Lys Ala Val Ser Glu Phe
    130                 135                 140

Glu Lys Asp Leu Ser Ser Ser Ser Ser Ser Gly Ser Ser Thr Glu Pro
145                 150                 155                 160

Glu Ala Ser Asp Thr Ala Lys Pro Asn Lys Pro Thr Glu Leu Glu Lys
                165                 170                 175

Lys Val Ala Glu Ala Gln Gln Lys Val Glu Glu Ala Glu Lys Lys Ala
            180                 185                 190

Lys Asp Gln Lys Glu Glu Asp Tyr Arg Asn Tyr Pro Thr Ile Thr Tyr
        195                 200                 205

Lys Thr Leu Glu Leu Glu Ile Ala Glu Phe Asp Val Lys Val Lys Glu
    210                 215                 220

Ala Glu Leu Glu Leu Val Lys Val Lys Ala Lys Glu Ser Arg Asp Glu
225                 230                 235                 240

Lys Lys Ile Lys Gln Ala Glu Ala Glu Val Glu Ser Lys Gln Ala Glu
                245                 250                 255

Ala Thr Arg Leu Lys Lys Ile Lys Thr Asp Arg Lys Lys Ala Glu Glu
            260                 265                 270

Glu Ala Lys Leu Lys Glu Ala Val Glu Lys Asn Ala Ala Thr Ser Glu
        275                 280                 285

Gln Gly Lys Pro Lys Arg Arg Val Lys Arg Arg Ala Leu Gly Glu Gln
    290                 295                 300

Ala Thr Pro Asp Lys Lys Asp Tyr Phe Glu Lys Asp Phe Arg Pro Ala
305                 310                 315                 320

Phe Asn Lys Asn Arg Gln Met Val Ala Ile Gln Glu Ser Leu Asn Lys
                325                 330                 335

Leu Asp Gly Glu Thr Lys Thr Val Pro Asp Gly Ala Lys Leu Thr Gly
            340                 345                 350

Glu Ala Gly Asn Ala Tyr Asn Glu Val Arg Asp Tyr Ala Ile Lys Val
```

```
        355                 360                 365

Val Ser Glu Asn Lys Lys Leu Leu Ser Gln Thr Ala Val Thr Met Asp
    370                 375                 380

Glu Leu Ala Met Gln Leu Thr Lys Leu Asn Asp Ala Met Ser Lys Leu
385                 390                 395                 400

Arg Glu Ala Lys Ala Lys Leu Val Pro Glu Val Lys Pro Gln Pro Glu
            405                 410                 415

Asn Pro Glu His Gln Arg Pro Thr Thr Pro Ala Pro Asp Thr Lys Pro
            420                 425                 430

Ile Pro Gln Pro Glu Gly Lys Lys Pro Ser Val Pro Asp Ile Asn Gln
        435                 440                 445

Glu Lys Glu Lys Ala Lys Leu Ala Val Ala Thr Tyr Met Ser Lys Ile
    450                 455                 460

Leu Asp Asp Ile Gln Lys His His Leu Gln Lys Glu Lys His Arg Gln
465                 470                 475                 480

Ile Val Ala Leu Ile Lys Glu Leu Asp Glu Phe Lys Lys Gln Ala Leu
            485                 490                 495

Ser Glu Ile Asp Asn Val Asn Thr Lys Val Glu Ile Glu Asn Thr Val
            500                 505                 510

His Lys Ile Phe Ala Asp Met Asp Ala Val Val Thr Lys Phe Lys Lys
        515                 520                 525

Gly Leu Thr Gln Asp Thr Pro Lys Glu Pro Asp Asn Lys Lys Pro Ser
    530                 535                 540

Ala Pro Lys Pro Gly Met Gln Pro Ser Pro Gln Pro Glu Gly Lys Lys
545                 550                 555                 560

Pro Ser Val Pro Ala Gln Pro Gly Thr Glu Asp Lys Lys Pro Ser Ala
            565                 570                 575

Pro Lys Pro Gly Met Gln Pro Ser Pro Gln Pro Glu Gly Lys Lys Pro
            580                 585                 590

Ser Val Pro Ala Gln Pro Gly Thr Glu Asp Lys Lys Pro Ser Ala Pro
        595                 600                 605

Lys Pro Asp Met Gln Pro Ser Pro Gln Pro Glu Gly Lys Lys Pro Ser
    610                 615                 620

Val Pro Ala Gln Pro Gly Thr Glu Asp Lys Lys Pro Ser Ala Pro Lys
625                 630                 635                 640

Pro Gly Met Gln Pro Ser Pro Gln Pro Glu Gly Lys Lys Pro Ser Val
            645                 650                 655

Pro Ala Gln Pro Gly Thr Glu Asp Lys Lys Pro Ser Ala Pro Lys Pro
            660                 665                 670

Asp Met Gln Pro Ser Pro Gln Pro Glu Gly Lys Lys Pro Ser Val Pro
        675                 680                 685

Ala Gln Pro Gly Thr Glu Asp Lys Lys Pro Ser Ala Pro Lys Pro Asp
    690                 695                 700

Met Gln Pro Ser Pro Gln Pro Glu Gly Lys Lys Pro Ser Val Pro Glu
705                 710                 715                 720

Ile Asn Gln Glu Lys Glu Lys Ala Lys Leu Ala Val Ala Thr Glu Lys
            725                 730                 735

Lys Leu Pro Ser Thr Gly Val Ala Ser Asn Leu Val Leu Glu Ile Ile
            740                 745                 750

Gly Leu Leu Gly Leu Ile Gly Thr Ser Phe Ile Ala Met Lys Arg Arg
        755                 760                 765

Lys
```

<210> SEQ ID NO 39
<211> LENGTH: 503
<212> TYPE: PRT
<213> ORGANISM: Streptococcus pneumoniae

<400> SEQUENCE: 39

Met Phe Ala Ser Lys Ser Glu Arg Lys Val His Tyr Ser Ile Arg Lys
1 5 10 15

Phe Ser Ile Gly Val Ala Ser Val Ala Val Ala Ser Leu Val Met Gly
20 25 30

Ser Val Val His Ala Thr Glu Asn Glu Gly Ser Thr Gln Ala Ala Thr
35 40 45

Ser Ser Asn Met Ala Asn Lys Ser Gln Thr Glu Gln Gly Glu Ile Asn
50 55 60

Ile Glu Arg Asp Lys Ala Lys Thr Ala Val Ser Glu Tyr Lys Glu Lys
65 70 75 80

Lys Val Ser Glu Ile Tyr Thr Lys Leu Glu Arg Asp Arg His Lys Asp
85 90 95

Thr Val Asp Leu Val Asn Lys Leu Gln Glu Ile Lys Asn Glu Tyr Leu
100 105 110

Asn Lys Ile Val Glu Ser Thr Ser Thr Ile Glu Ile Gln Gly Leu Ile
115 120 125

Thr Thr Ser Arg Ser Lys Leu Asp Glu Ala Val Ser Lys Tyr Lys Lys
130 135 140

Ala Pro Ser Ser Ser Ser Ser Ser Gly Ser Ser Thr Lys Pro Glu Thr
145 150 155 160

Pro Gln Pro Glu Thr Ser Lys Pro Glu Val Lys Pro Glu Pro Glu Thr
165 170 175

Pro Lys Pro Glu Val Lys Pro Glu Pro Glu Thr Pro Lys Pro Glu Val
180 185 190

Lys Pro Glu Pro Glu Thr Pro Lys Pro Glu Val Lys Pro Glu Leu Glu
195 200 205

Thr Pro Lys Pro Glu Val Lys Pro Glu Pro Glu Thr Pro Lys Pro Glu
210 215 220

Val Lys Pro Glu Pro Glu Thr Pro Lys Pro Glu Val Lys Pro Glu Pro
225 230 235 240

Glu Thr Pro Lys Pro Glu Val Lys Pro Glu Leu Glu Thr Pro Lys Pro
245 250 255

Glu Val Lys Pro Glu Leu Glu Thr Pro Lys Pro Glu Val Lys Pro Glu
260 265 270

Pro Glu Thr Pro Lys Pro Glu Val Lys Pro Glu Leu Glu Thr Pro Lys
275 280 285

Pro Glu Val Lys Pro Glu Pro Glu Thr Pro Lys Pro Glu Val Lys Pro
290 295 300

Glu Leu Glu Thr Pro Lys Pro Glu Val Lys Pro Glu Pro Glu Thr Pro
305 310 315 320

Lys Pro Glu Val Lys Pro Glu Leu Glu Thr Pro Lys Pro Glu Val Lys
325 330 335

Pro Glu Pro Glu Thr Pro Lys Pro Glu Val Lys Pro Glu Pro Glu Thr
340 345 350

Pro Lys Pro Glu Val Lys Pro Glu Pro Glu Thr Pro Lys Pro Glu Val
355 360 365

Lys Pro Glu Pro Glu Thr Pro Lys Pro Glu Val Lys Pro Glu Pro Glu
370 375 380

Thr Pro Lys Pro Glu Val Lys Pro Glu Pro Glu Thr Pro Lys Pro Glu
385 390 395 400

Val Lys Pro Glu Pro Glu Thr Pro Lys Pro Glu Val Lys Pro Glu Pro
405 410 415

Glu Thr Pro Lys Pro Glu Val Lys Pro Asp Asn Ser Lys Pro Gln Ala
420 425 430

Asp Asp Lys Lys Pro Ser Thr Pro Asn Asn Leu Ser Lys Asp Lys Gln
435 440 445

Ser Ser Asn Gln Ala Ser Thr Asn Glu Asn Lys Lys Gln Gly Pro Ala
450 455 460

Thr Asn Lys Pro Lys Lys Ser Leu Pro Ser Thr Gly Ser Ile Ser Asn
465 470 475 480

Leu Ala Leu Glu Ile Ala Gly Leu Leu Thr Leu Ala Gly Ala Thr Ile
485 490 495

Leu Ala Lys Lys Arg Met Lys
500

<210> SEQ ID NO 40
<211> LENGTH: 612
<212> TYPE: PRT
<213> ORGANISM: Streptococcus pneumoniae

<400> SEQUENCE: 40

Met Phe Ala Ser Lys Asn Glu Arg Lys Val His Tyr Ser Ile Arg Lys
1 5 10 15

Phe Ser Ile Gly Val Ala Ser Val Ala Val Ala Ser Leu Phe Met Gly
20 25 30

Ser Val Val His Ala Thr Glu Lys Glu Val Thr Thr Gln Val Ala Thr
35 40 45

Ser Ser Asn Lys Ala Asn Lys Ser Gln Thr Glu His Met Lys Ala Ala
50 55 60

Lys Gln Val Asp Glu Tyr Ile Glu Lys Met Leu Ser Glu Ile Gln Leu
65 70 75 80

Asp Arg Arg Lys His Thr Gln Asn Val Gly Leu Leu Thr Lys Leu Gly
85 90 95

Ala Ile Lys Thr Glu Tyr Leu Arg Gly Leu Ser Val Ser Lys Glu Lys
100 105 110

Ser Thr Ala Glu Leu Pro Ser Glu Ile Lys Glu Lys Leu Thr Ala Ala
115 120 125

Phe Glu Gln Phe Lys Lys Asp Thr Leu Lys Ser Gly Lys Lys Val Ala
130 135 140

Glu Ala Gln Lys Lys Ala Lys Asp Gln Lys Glu Ala Lys Gln Glu Ile
145 150 155 160

Glu Ala Leu Ile Val Lys His Lys Gly Arg Glu Ile Asp Leu Asp Arg
165 170 175

Lys Lys Ala Lys Ala Ala Val Thr Glu His Leu Lys Lys Leu Leu Asn
180 185 190

Asp Ile Glu Lys Asn Leu Lys Lys Glu Gln His Thr His Thr Val Glu
195 200 205

Leu Ile Lys Asn Leu Lys Asp Ile Glu Lys Thr Tyr Leu His Lys Leu
210 215 220

Asp Glu Ser Thr Gln Lys Ala Gln Leu Gln Lys Leu Ile Ala Glu Ser
225 230 235 240

Gln Ser Lys Leu Asp Glu Ala Phe Ser Lys Phe Lys Asn Gly Leu Ser

```
                245                 250                 255

Ser Ser Ser Asn Ser Gly Ser Ser Thr Lys Pro Glu Thr Pro Gln Pro
            260                 265                 270

Glu Thr Pro Lys Pro Glu Val Lys Pro Glu Leu Glu Thr Pro Lys Pro
        275                 280                 285

Glu Val Lys Pro Glu Pro Glu Thr Pro Lys Pro Glu Val Lys Pro Glu
    290                 295                 300

Leu Glu Thr Pro Lys Pro Glu Val Lys Pro Glu Pro Glu Thr Pro Lys
305                 310                 315                 320

Pro Glu Val Lys Pro Glu Leu Glu Thr Pro Lys Pro Glu Val Lys Pro
                325                 330                 335

Glu Leu Glu Thr Pro Lys Pro Glu Val Lys Pro Glu Pro Glu Thr Pro
            340                 345                 350

Lys Pro Glu Val Lys Pro Glu Leu Glu Thr Pro Lys Pro Glu Val Lys
        355                 360                 365

Pro Glu Leu Glu Thr Pro Lys Pro Glu Val Lys Pro Glu Leu Glu Thr
    370                 375                 380

Pro Lys Pro Glu Val Lys Pro Glu Leu Glu Thr Pro Lys Pro Glu Val
385                 390                 395                 400

Lys Pro Glu Leu Glu Thr Pro Lys Pro Glu Val Lys Pro Glu Leu Glu
                405                 410                 415

Thr Pro Lys Pro Glu Val Lys Pro Glu Leu Glu Thr Pro Lys Pro Glu
            420                 425                 430

Val Lys Pro Glu Leu Glu Thr Pro Lys Pro Glu Val Lys Pro Glu Pro
        435                 440                 445

Glu Thr Pro Lys Pro Glu Val Lys Pro Glu Pro Glu Thr Pro Lys Pro
    450                 455                 460

Glu Val Lys Pro Glu Leu Glu Thr Pro Lys Pro Glu Val Lys Pro Glu
465                 470                 475                 480

Leu Glu Thr Pro Lys Pro Glu Val Lys Pro Glu Leu Glu Thr Pro Lys
                485                 490                 495

Pro Glu Val Lys Pro Glu Pro Glu Thr Pro Lys Pro Glu Val Lys Pro
            500                 505                 510

Glu Leu Glu Thr Pro Lys Pro Glu Val Lys Pro Glu Pro Glu Ile Pro
        515                 520                 525

Lys Pro Glu Val Lys Pro Asp Asn Ser Lys Pro Gln Ala Asp Asp Lys
    530                 535                 540

Lys Pro Ser Thr Pro Asn Asn Leu Ser Lys Asp Lys Gln Ser Ser Asn
545                 550                 555                 560

Gln Ala Ser Thr Asn Glu Asn Lys Lys Gln Gly Pro Ala Thr Asn Lys
                565                 570                 575

Pro Lys Lys Ser Leu Pro Ser Thr Gly Ser Ile Ser Asn Leu Ala Leu
            580                 585                 590

Glu Ile Ala Gly Leu Leu Thr Leu Ala Gly Ala Thr Ile Leu Ala Lys
        595                 600                 605

Lys Arg Met Lys
    610
```

<210> SEQ ID NO 41
<211> LENGTH: 635
<212> TYPE: PRT
<213> ORGANISM: Streptococcus pneumoniae

<400> SEQUENCE: 41

```
Met Asn Lys Lys Lys Met Ile Leu Thr Ser Leu Ala Ser Val Ala Ile
1               5                   10                  15

Leu Gly Ala Gly Phe Val Ala Ser Gln Pro Thr Phe Val Arg Ala Glu
            20                  25                  30

Glu Ser Pro Val Ala Ser Gln Ser Lys Ala Glu Lys Asp Tyr Asp Ala
        35                  40                  45

Ala Val Lys Lys Ser Glu Ala Ala Lys Lys Ala Tyr Glu Glu Ala Lys
    50                  55                  60

Lys Ala Leu Glu Glu Ala Lys Val Ala Gln Lys Lys Tyr Glu Asp Asp
65                  70                  75                  80

Gln Lys Lys Thr Glu Glu Lys Ala Glu Leu Glu Lys Glu Ala Ser Glu
                85                  90                  95

Ala Ile Ala Lys Ala Thr Glu Glu Val Gln Gln Ala Tyr Leu Ala Tyr
            100                 105                 110

Gln Arg Ala Ser Asn Lys Ala Glu Ala Ala Lys Met Ile Glu Glu Ala
        115                 120                 125

Gln Arg Arg Glu Asn Glu Ala Arg Ala Lys Phe Thr Thr Ile Arg Thr
    130                 135                 140

Thr Met Val Val Pro Glu Pro Glu Gln Leu Ala Glu Thr Lys Lys Lys
145                 150                 155                 160

Ala Glu Glu Ala Lys Ala Lys Glu Pro Lys Leu Ala Lys Lys Ala Ala
                165                 170                 175

Glu Ala Lys Ala Lys Leu Glu Glu Ala Glu Lys Lys Ala Thr Glu Ala
            180                 185                 190

Lys Gln Lys Val Asp Ala Glu Glu Val Ala Pro Gln Ala Lys Ile Ala
        195                 200                 205

Glu Leu Glu Asn Gln Val His Arg Leu Glu Gln Glu Leu Lys Glu Ile
    210                 215                 220

Asp Glu Ser Glu Ser Glu Asp Tyr Ala Lys Glu Gly Phe Arg Ala Pro
225                 230                 235                 240

Leu Gln Ser Lys Leu Asp Ala Lys Lys Ala Lys Leu Ser Lys Leu Glu
                245                 250                 255

Glu Leu Ser Asp Lys Ile Asp Glu Leu Asp Ala Glu Ile Ala Lys Leu
            260                 265                 270

Glu Asp Gln Leu Lys Ala Ala Glu Glu Asn Asn Asn Val Glu Asp Tyr
        275                 280                 285

Phe Lys Glu Gly Leu Glu Lys Thr Ile Ala Ala Lys Lys Ala Glu Leu
    290                 295                 300

Glu Lys Thr Glu Ala Asp Leu Lys Lys Ala Val Asn Glu Pro Glu Lys
305                 310                 315                 320

Ser Ala Glu Glu Pro Ser Gln Pro Glu Lys Pro Ala Glu Glu Ala Pro
                325                 330                 335

Ala Pro Glu Gln Pro Thr Glu Pro Thr Gln Pro Glu Lys Pro Ala Glu
            340                 345                 350

Glu Thr Pro Ala Pro Lys Pro Glu Lys Pro Ala Glu Gln Pro Lys Ala
        355                 360                 365

Glu Lys Thr Asp Asp Gln Gln Ala Glu Glu Asp Tyr Ala Arg Arg Ser
    370                 375                 380

Glu Glu Glu Tyr Asn Arg Leu Thr Gln Gln Gln Pro Pro Lys Ala Glu
385                 390                 395                 400

Lys Pro Ala Pro Ala Pro Gln Pro Glu Gln Pro Ala Pro Ala Pro Lys
                405                 410                 415

Thr Gly Trp Lys Gln Glu Asn Gly Met Trp Tyr Phe Tyr Asn Thr Asp
```

```
            420                 425                 430

Gly Ser Met Ala Thr Gly Trp Leu Gln Asn Asn Gly Ser Trp Tyr Tyr
        435                 440                 445

Leu Asn Ser Asn Gly Ala Met Ala Thr Gly Trp Leu Gln Tyr Asn Gly
    450                 455                 460

Ser Trp Tyr Tyr Leu Asn Ala Asn Gly Ala Met Ala Thr Gly Trp Ala
465                 470                 475                 480

Lys Val Asn Gly Ser Trp Tyr Tyr Leu Asn Ala Asn Gly Ser Met Ala
                485                 490                 495

Thr Gly Trp Val Lys Asp Gly Asp Thr Trp Tyr Tyr Leu Glu Ala Ser
            500                 505                 510

Gly Ala Met Lys Ala Ser Gln Trp Phe Lys Val Ser Asp Lys Trp Tyr
        515                 520                 525

Tyr Val Asn Ser Asn Gly Ala Met Ala Thr Gly Trp Leu Gln Tyr Asn
    530                 535                 540

Gly Ser Trp Tyr Tyr Leu Asn Ala Asn Gly Ala Met Ala Thr Gly Trp
545                 550                 555                 560

Ala Lys Val Asn Gly Ser Trp Tyr Tyr Leu Asn Ala Asn Gly Ser Met
                565                 570                 575

Ala Thr Gly Trp Val Lys Asp Gly Asp Thr Trp Tyr Tyr Leu Glu Ala
            580                 585                 590

Ser Gly Ala Met Lys Ala Ser Gln Trp Phe Lys Val Ser Asp Lys Trp
        595                 600                 605

Tyr Tyr Val Asn Gly Ser Gly Ser Leu Ala Val Asn Thr Thr Val Asp
    610                 615                 620

Gly Tyr Thr Val Asn Glu Asn Gly Glu Trp Val
625                 630                 635


<210> SEQ ID NO 42
<211> LENGTH: 665
<212> TYPE: PRT
<213> ORGANISM: Streptococcus pneumoniae

<400> SEQUENCE: 42

Met Lys Ser Ile Asn Lys Phe Leu Thr Met Leu Ala Ala Leu Leu Leu
1               5                   10                  15

Thr Ala Ser Ser Leu Phe Ser Ala Ala Thr Val Phe Ala Ala Gly Thr
            20                  25                  30

Thr Thr Thr Ser Val Thr Val His Lys Leu Leu Ala Thr Asp Gly Asp
        35                  40                  45

Met Asp Lys Ile Ala Asn Glu Leu Glu Thr Gly Asn Tyr Ala Gly Asn
    50                  55                  60

Lys Val Gly Val Leu Pro Ala Asn Ala Lys Glu Ile Ala Gly Val Met
65                  70                  75                  80

Phe Val Trp Thr Asn Thr Asn Asn Glu Ile Ile Asp Glu Asn Gly Gln
                85                  90                  95

Thr Leu Gly Val Asn Ile Asp Pro Gln Thr Phe Lys Leu Ser Gly Ala
            100                 105                 110

Met Pro Ala Thr Ala Met Lys Lys Leu Thr Glu Ala Glu Gly Ala Lys
        115                 120                 125

Phe Asn Thr Ala Asn Leu Pro Ala Ala Lys Tyr Lys Ile Tyr Glu Ile
    130                 135                 140

His Ser Leu Ser Thr Tyr Val Gly Glu Asp Gly Ala Thr Leu Thr Gly
145                 150                 155                 160
```

```
Ser Lys Ala Val Pro Ile Glu Ile Glu Leu Pro Leu Asn Asp Val Val
                165                 170                 175

Asp Ala His Val Tyr Pro Lys Asn Thr Glu Ala Lys Pro Lys Ile Asp
            180                 185                 190

Lys Asp Phe Lys Gly Lys Ala Asn Pro Asp Thr Pro Arg Val Asp Lys
        195                 200                 205

Asp Thr Pro Val Asn His Gln Val Gly Asp Val Val Glu Tyr Glu Ile
    210                 215                 220

Val Thr Lys Ile Pro Ala Leu Ala Asn Tyr Ala Thr Ala Asn Trp Ser
225                 230                 235                 240

Asp Arg Met Thr Glu Gly Leu Ala Phe Asn Lys Gly Thr Val Lys Val
                245                 250                 255

Thr Val Asp Asp Val Ala Leu Glu Ala Gly Asp Tyr Ala Leu Thr Glu
            260                 265                 270

Val Ala Thr Gly Phe Asp Leu Lys Leu Thr Asp Ala Gly Leu Ala Lys
        275                 280                 285

Val Asn Asp Gln Asn Ala Glu Lys Thr Val Lys Ile Thr Tyr Ser Ala
    290                 295                 300

Thr Leu Asn Asp Lys Ala Ile Val Glu Val Pro Glu Ser Asn Asp Val
305                 310                 315                 320

Thr Phe Asn Tyr Gly Asn Asn Pro Asp His Gly Asn Thr Pro Lys Pro
                325                 330                 335

Asn Lys Pro Asn Glu Asn Gly Asp Leu Thr Leu Thr Lys Thr Trp Val
            340                 345                 350

Asp Ala Thr Gly Ala Pro Ile Pro Ala Gly Ala Glu Ala Thr Phe Asp
        355                 360                 365

Leu Val Asn Ala Gln Thr Gly Lys Val Val Gln Thr Val Thr Leu Thr
    370                 375                 380

Thr Asp Lys Asn Thr Val Thr Val Asn Gly Leu Asp Lys Asn Thr Glu
385                 390                 395                 400

Tyr Lys Phe Val Glu Arg Ser Ile Lys Gly Tyr Ser Ala Asp Tyr Gln
                405                 410                 415

Glu Ile Thr Thr Ala Gly Glu Ile Ala Val Lys Asn Trp Lys Asp Glu
            420                 425                 430

Asn Pro Lys Pro Leu Asp Pro Thr Glu Pro Lys Val Val Thr Tyr Gly
        435                 440                 445

Lys Lys Phe Val Lys Val Asn Asp Lys Asp Asn Arg Leu Ala Gly Ala
    450                 455                 460

Glu Phe Val Ile Ala Asn Ala Asp Asn Ala Gly Gln Tyr Leu Ala Arg
465                 470                 475                 480

Lys Ala Asp Lys Val Ser Gln Glu Glu Lys Gln Leu Val Val Thr Thr
                485                 490                 495

Lys Asp Ala Leu Asp Arg Ala Val Ala Ala Tyr Asn Ala Leu Thr Ala
            500                 505                 510

Gln Gln Gln Thr Gln Gln Glu Lys Glu Lys Val Asp Lys Ala Gln Ala
        515                 520                 525

Ala Tyr Asn Ala Ala Val Ile Ala Ala Asn Asn Ala Phe Glu Trp Val
    530                 535                 540

Ala Asp Lys Asp Asn Glu Asn Val Val Lys Leu Val Ser Asp Ala Gln
545                 550                 555                 560

Gly Arg Phe Glu Ile Thr Gly Leu Leu Ala Gly Thr Tyr Tyr Leu Glu
                565                 570                 575

Glu Thr Lys Gln Pro Ala Gly Tyr Ala Leu Leu Thr Ser Arg Gln Lys
```

```
            580                 585                 590

Phe Glu Val Thr Ala Thr Ser Tyr Ser Ala Thr Gly Gln Gly Ile Glu
        595                 600                 605

Tyr Thr Ala Gly Ser Gly Lys Asp Asp Ala Thr Lys Val Val Asn Lys
    610                 615                 620

Lys Ile Thr Ile Pro Gln Thr Gly Gly Ile Gly Thr Ile Ile Phe Ala
625                 630                 635                 640

Val Ala Gly Ala Ala Ile Met Gly Ile Ala Val Tyr Ala Tyr Val Lys
                645                 650                 655

Asn Asn Lys Asp Glu Asp Gln Leu Ala
            660                 665


<210> SEQ ID NO 43
<211> LENGTH: 431
<212> TYPE: PRT
<213> ORGANISM: Streptococcus pyogenes

<400> SEQUENCE: 43

Met Phe Lys Lys Lys Pro Phe Arg Glu Glu His Val Met Ser Trp Asn
1               5                   10                  15

Trp Lys Lys Thr Ser Val Leu Gly Thr Leu Ser Leu Ala Ser Val Leu
            20                  25                  30

Pro Leu Thr Ala Cys Val Ser Gly Gly Gly Lys Gly Val Lys Glu Thr
        35                  40                  45

Asp Gly Lys Thr Ile Val Val Ser Val Asp Glu Gly Tyr Val Asp Tyr
    50                  55                  60

Ile Lys Ser Ile Lys Gly Glu Phe Glu Lys Glu His Lys Val Thr Val
65                  70                  75                  80

Lys Val Lys Lys Glu Gly Met Met Asp Thr Leu Asp Lys Leu Ser Thr
                85                  90                  95

Asp Gly Pro Thr Gly Ala Ser Pro Asp Val Phe Leu Ala Pro Phe Asp
            100                 105                 110

Arg Val Gly Gly Leu Gly Thr Glu Gly Gln Ile Ala Glu Val Thr Leu
        115                 120                 125

Gly Asn Ser Lys Glu Phe Asp Asp Thr Val Lys Lys Leu Val Thr Ile
    130                 135                 140

Asp Gly Lys Thr Tyr Gly Ala Pro Asp Val Ile Glu Thr Leu Val Thr
145                 150                 155                 160

Tyr Tyr Asn Lys Asp Leu Val Pro Gln Ala Pro Lys Ser Phe Thr Glu
                165                 170                 175

Leu Glu Val Leu Gln Lys Asp Ser Lys Phe Ala Phe Ala Ser Glu Pro
            180                 185                 190

Gly Lys Ser Val Gly Phe Leu Ala Lys Trp Thr Asp Phe Tyr Tyr Gly
        195                 200                 205

Tyr Gly Leu Ile Ala Gly Tyr Gly Gly Tyr Ile Phe Gly Asp Lys Gly
    210                 215                 220

Thr Lys Pro Ser Asp Leu Gly Leu Gly Asn Asp Gly Thr Val Glu Gly
225                 230                 235                 240

Leu Asn Tyr Ala Lys Gln Trp Tyr Gly Thr Trp Pro Gln Gly Met Gln
                245                 250                 255

Asp Thr Lys Lys Ala Gly Asp Phe Ile Thr Glu Gln Phe Ile Ser Lys
            260                 265                 270

Lys Ala Gly Val Ile Ile Asp Gly Pro Trp Ala Ala Ser Ser Phe Lys
        275                 280                 285
```

```
Asp Ala Gly Val Asn Phe Gly Val Met Glu Ile Pro Thr Leu Thr Asn
    290                 295                 300

Gly Lys Lys Tyr Gln Pro Phe Ala Gly Gly Lys Ala Trp Val Ile Ser
305                 310                 315                 320

Asn Tyr Ser Lys Gly Lys Thr Thr Ala Gln Lys Phe Leu Asp Tyr Val
                325                 330                 335

Thr Asn Ala Glu Asn Gln Lys Arg Phe Tyr Asp Lys Thr Gln Glu Ile
            340                 345                 350

Pro Ala Asn Leu Thr Ala Arg Asn Tyr Ala Ser Lys Glu Gly Asn Glu
        355                 360                 365

Leu Thr Lys Ala Val Ile Ser Gln Phe Glu Asn Ala Gln Pro Met Pro
    370                 375                 380

Asn Ile Pro Glu Met Ala Glu Val Trp Glu Pro Gly Ala Asn Met Phe
385                 390                 395                 400

Phe Asn Val Ala Ser Gly Lys Glu Glu Ala Ser Lys Ala Ala Lys Glu
                405                 410                 415

Ala Ala Lys Thr Ile Lys Glu Ala Ile Glu Gln Lys Tyr Ala Glu
            420                 425                 430


<210> SEQ ID NO 44
<211> LENGTH: 419
<212> TYPE: PRT
<213> ORGANISM: Streptococcus suis

<400> SEQUENCE: 44

Met Lys His Asn Leu Leu Lys Ser Val Ala Leu Leu Ala Ala Ser Thr
1               5                   10                  15

Ala Val Leu Ala Ala Cys Ser Asn Ser Gly Ser Ser Thr Glu Ala Ser
            20                  25                  30

Lys Ser Ala Glu Gly Ser Lys Glu Leu Thr Val Tyr Val Asp Gln Gly
        35                  40                  45

Tyr Glu Ser Tyr Ile Asn Asp Val Lys Ala Gly Phe Glu Lys Glu Asn
    50                  55                  60

Gly Val Ser Val Thr Val Lys Thr Gly Asp Ala Leu Thr Gly Leu Asp
65                  70                  75                  80

Asn Leu Ser Leu Asp Asn Gln Ser Gly Ser Ala Pro Asp Val Met Met
                85                  90                  95

Ala Pro Tyr Asp Arg Val Gly Ser Leu Gly Ser Glu Gly Gln Leu Ser
            100                 105                 110

Glu Leu Thr Leu Ala Asp Asp Ser Lys Ala Asp Asp Thr Thr Thr Ala
        115                 120                 125

Leu Val Thr Asn Gly Gly Lys Val Tyr Gly Ser Pro Ala Val Ile Glu
    130                 135                 140

Thr Leu Val Leu Tyr Tyr Asn Lys Asp Leu Leu Thr Glu Ala Pro Lys
145                 150                 155                 160

Thr Phe Ala Glu Leu Glu Thr Leu Ala Lys Asp Ser Lys Tyr Ala Phe
                165                 170                 175

Ala Gly Glu Glu Gly Lys Thr Ser Ala Phe Leu Ala Asp Trp Thr Asn
            180                 185                 190

Phe Tyr Tyr Thr Tyr Gly Leu Leu Ser Gly Tyr Gly Gly Tyr Val Phe
        195                 200                 205

Gly Glu Asn Gly Thr Asn Pro Lys Asp Ile Gly Leu Ala Asn Glu Gly
    210                 215                 220

Ala Ile Lys Ala Ile Glu Tyr Ala Lys Thr Trp Tyr Glu Lys Trp Pro
225                 230                 235                 240
```

```
Gln Gly Leu Gln Asp Gly Thr Ala Ala Asn Asn Leu Ile Asn Thr Gln
                245                 250                 255

Phe Thr Asp Gly Lys Ala Ala Ala Ile Ile Glu Gly Pro Trp Lys Ala
            260                 265                 270

Ala Ser Tyr Lys Glu Ala Gly Val Asn Tyr Gly Val Ala Thr Ile Pro
        275                 280                 285

Thr Leu Val Asn Gly Lys Asn Tyr Ser Ala Phe Gly Gly Gly Lys Ala
    290                 295                 300

Trp Val Val Pro Ala Gly Ala Lys Asn Gln Glu Met Ala Gln Lys Phe
305                 310                 315                 320

Val Asp Phe Leu Thr Ala Thr Asp Gln Gln Lys Ala Leu Tyr Asp Ala
                325                 330                 335

Thr Asn Glu Val Pro Ala Asn Thr Glu Ala Arg Glu Tyr Ala Val Ser
            340                 345                 350

Lys Lys Asp Glu Leu Thr Thr Ala Val Ile Asn Gln Phe Ala Ser Ala
        355                 360                 365

Gln Pro Met Pro Asn Ile Ser Glu Met Gly Ser Val Trp Thr Pro Ala
    370                 375                 380

Gly Asn Met Leu Phe Glu Ala Ala Ser Gly Ser Lys Asp Ala Lys Thr
385                 390                 395                 400

Ala Ala Thr Asp Ala Val Lys Ala Ile Ala Asp Glu Ile Ala Gln Lys
                405                 410                 415

His Ser Asn


<210> SEQ ID NO 45
<211> LENGTH: 419
<212> TYPE: PRT
<213> ORGANISM: Streptococcus equi

<400> SEQUENCE: 45

Met Ala Trp Asp Trp Lys Lys Ala Gly Val Val Gly Val Val Ser Leu
1               5                   10                  15

Ala Ser Thr Met Val Leu Ser Ala Cys Ser Gly Gly His Gln Lys Glu
            20                  25                  30

Ala Lys Gln Lys Asp Asp Asn Thr Ile Val Val Ser Val Asp Glu Gly
        35                  40                  45

Tyr Ala Asp Tyr Ile Lys Glu Ile Lys Thr Ala Phe Glu Lys Asp Asn
    50                  55                  60

Lys Val Lys Val Lys Val Lys Lys Glu Gly Met Ile Asp Thr Leu Asp
65                  70                  75                  80

Lys Leu Ser Thr Asp Gly Pro Thr Gly Ala Ser Pro Asp Val Phe Leu
                85                  90                  95

Ala Pro Tyr Asp Arg Val Gly Gly Leu Gly Ser Glu Gly Gln Ile Ala
            100                 105                 110

Glu Val Ser Leu Gly Asn Ala Asp Gln Phe Asp Asp Thr Val Lys Lys
        115                 120                 125

Leu Val Thr Ile Asn Gly Lys Val Tyr Gly Ala Pro Asn Val Ile Glu
    130                 135                 140

Thr Leu Val Met Tyr Tyr Asn Lys Asp Leu Val Ser Glu Ala Pro Lys
145                 150                 155                 160

Thr Phe Ala Asp Ile Glu Glu Leu Asn Lys Asp Pro Lys Phe Ala Phe
                165                 170                 175

Ala Ser Glu Asp Gly Lys Ser Val Gly Phe Leu Ala Lys Trp Thr Asp
            180                 185                 190
```

```
Phe Tyr Tyr Gly Tyr Gly Leu Ile Ala Gly Tyr Gly Ala Tyr Val Phe
        195                 200                 205

Gly Asp Lys Gly Thr Asp Pro Lys Asp Leu Gly Ile Gly Asn Ala Gly
    210                 215                 220

Thr Ile Glu Gly Leu Glu Tyr Ala Lys Lys Trp Tyr Ser Val Trp Pro
225                 230                 235                 240

Gln Gly Met Gln Asp Thr Gln Lys Ala Gly Asp Phe Ile Thr Glu Gln
                245                 250                 255

Phe Thr Ser Lys Lys Ala Gly Val Ile Ile Asp Gly Pro Trp Ala Ala
            260                 265                 270

Ala Ser Phe Lys Glu Ala Gly Val Asn Phe Gly Val Ala Gln Ile Pro
        275                 280                 285

Ser Leu Pro Asn Gly Gly Ser Tyr Gln Ala Phe Gly Gly Gly Lys Ala
    290                 295                 300

Trp Val Ile Ser Asn Tyr Ser Lys Asn Lys Lys Leu Ala Gln Gln Phe
305                 310                 315                 320

Leu Asp Tyr Val Thr Asn Glu Lys Asn Gln Lys Ala Phe Tyr Asp Lys
                325                 330                 335

Met Gln Glu Ile Pro Ala Asn Leu Ala Ala Arg Ser Tyr Ala Ala Glu
            340                 345                 350

Gln Gly Asn Glu Leu Thr Lys Ala Val Ile Gly Gln Phe Ser Asn Ala
        355                 360                 365

Gln Pro Met Pro Asn Ile Pro Glu Met Ala Glu Val Trp Gly Pro Gly
    370                 375                 380

Ala Asn Met Phe Phe Glu Val Ala Ala Gly Lys Lys Thr Pro Ala Lys
385                 390                 395                 400

Ala Ala Lys Glu Ala Ala Lys Thr Ile Gln Glu Ala Ile Ala Gln Lys
                405                 410                 415

Tyr Thr Glu
```

<210> SEQ ID NO 46
<211> LENGTH: 423
<212> TYPE: PRT
<213> ORGANISM: Streptococcus mitis

<400> SEQUENCE: 46

```
Met Ser Ser Lys Phe Met Lys Ser Ala Ala Val Leu Gly Thr Val Thr
1               5                   10                  15

Leu Ala Ser Leu Leu Leu Val Ala Cys Gly Ser Lys Ser Ala Asp Lys
            20                  25                  30

Ala Ala Asp Ser Gly Ser Ser Glu Ala Lys Glu Leu Thr Val Tyr Val
        35                  40                  45

Asp Glu Gly Tyr Lys Ser Tyr Ile Glu Glu Val Ala Lys Ala Tyr Glu
    50                  55                  60

Lys Asp Ser Gly Val Lys Val Thr Ile Lys Thr Gly Asp Ala Leu Gly
65                  70                  75                  80

Gly Leu Asp Lys Leu Ser Leu Asp Asn Gln Ser Gly Asp Val Pro Asp
                85                  90                  95

Ile Met Met Ala Pro Tyr Asp Arg Val Gly Ser Leu Gly Thr Asp Gly
            100                 105                 110

Gln Leu Ser Glu Val Lys Leu Ser Asp Ser Ala Lys Thr Asp Asp Lys
        115                 120                 125

Thr Lys Ser Leu Val Thr Ala Ala Asp Gly Lys Val Tyr Gly Ala Pro
    130                 135                 140
```

```
Ala Val Ile Glu Ser Leu Val Met Tyr Tyr Asn Lys Asp Leu Ile Lys
145                 150                 155                 160

Glu Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Ala Tyr Gly Leu Leu Ala Gly Asn Gly
        195                 200                 205

Ala Tyr Val Phe Gly Gln Asn Gly Lys Asp Ala Lys Asp Ile Gly Leu
    210                 215                 220

Ala Asn Glu Gly Ser Ile Thr Gly Ile Asn Tyr Ala Lys Ser Trp Tyr
225                 230                 235                 240

Glu Lys Trp Pro Lys Gly Met Gln Asp Thr Glu Gly Ala Gly Asn Leu
                245                 250                 255

Ile Gln Thr His Phe Gln Glu Gly Lys Thr Ala Ala Ile Ile Asp Gly
            260                 265                 270

Pro Trp Lys Ala Gln Ala Phe Lys Asp Ala Lys Val Asn Tyr Gly Val
        275                 280                 285

Ala Thr Ile Pro Thr Leu Pro Asn Gly Lys Glu Tyr Ala Ala Phe Gly
    290                 295                 300

Gly Gly Lys Ala Trp Val Ile Pro Gln Ala Thr Lys Asn Leu Glu Ala
305                 310                 315                 320

Ser Gln Lys Phe Val Asp Phe Leu Val Ser Thr Glu Gln Gln Lys Val
                325                 330                 335

Leu Tyr Asp Lys Thr Asn Glu Ile Pro Ala Asn Thr Glu Ala Arg Ser
            340                 345                 350

Tyr Ala Glu Gly Lys Asn Asp Glu Leu Thr Thr Ala Val Ile Lys Gln
        355                 360                 365

Phe Lys Asn Ala Gln Pro Met Pro Asn Ile Ser Gln Met Ser Ala Val
    370                 375                 380

Trp Asp Pro Ala Lys Asn Met Leu Phe Asp Ala Val Ser Gly Lys Lys
385                 390                 395                 400

Asp Ala Lys Thr Ala Ala Asn Asp Ala Val Thr Arg Ile Lys Glu Thr
                405                 410                 415

Ile Lys Gln Lys Phe Gly Glu
            420


<210> SEQ ID NO 47
<211> LENGTH: 423
<212> TYPE: PRT
<213> ORGANISM: Streptococcus pseudopneumoniae

<400> SEQUENCE: 47

Met Ser Ser Lys Phe Met Lys Ser Ala Ala Val Leu Gly Thr Ala Thr
1               5                   10                  15

Leu Ala Ser Leu Leu Leu Val Ala Cys Gly Ser Lys Thr Ala Asp Lys
            20                  25                  30

Pro Ala Glu Ser Gly Ser Ser Glu Ala Lys Glu Ile Thr Leu Tyr Val
        35                  40                  45

Glu Asp Gln Tyr Lys Ala Tyr Ala Glu Thr Val Ala Lys Ala Tyr Lys
    50                  55                  60

Glu Gln Ser Gly Thr Thr Val Asn Ile Lys Ser Gly Asp Gln Leu Gly
65                  70                  75                  80

Gly Leu Asp Lys Leu Ser Leu Asp Asn Gln Ser Gly Gln Ala Ala Asp
```

```
                85                  90                  95

Val Met Met Ala Pro Tyr Asp Arg Val Gly Ser Leu Gly Ser Asp Gly
            100                 105                 110

Gln Leu Ser Glu Val Lys Leu Ser Asp Gly Ala Lys Thr Glu Asp Thr
        115                 120                 125

Thr Lys Ser Leu Val Thr Ala Ala Asp Gly Lys Val Tyr Gly Ala Pro
    130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Ser Ala Phe Leu Ala
            180                 185                 190

Asp Trp Thr Asn Phe Tyr Tyr Ala Tyr Gly Leu Leu Ala Gly Asn Gly
        195                 200                 205

Ala Tyr Val Phe Gly Gln Asn Gly Lys Asp Pro Lys Asp Ile Gly Leu
    210                 215                 220

Ala Asn Asp Gly Ser Ile Ala Gly Ile Asn Tyr Ala Lys Ser Trp Tyr
225                 230                 235                 240

Glu Lys Trp Pro Lys Gly Met Gln Asp Gly Thr Ala Ala Gly Asn Leu
                245                 250                 255

Ile Gln Thr Gln Phe Gln Glu Gly Lys Thr Ala Ala Ile Ile Asp Gly
            260                 265                 270

Pro Trp Lys Ala Gln Ala Leu Lys Asp Ala Lys Val Asn Tyr Gly Val
        275                 280                 285

Ala Thr Ile Pro Thr Leu Pro Asn Gly Lys Glu Tyr Ala Ala Phe Gly
    290                 295                 300

Gly Gly Lys Ala Trp Ile Ile Pro Ser Ser Thr Lys Asn Leu Glu Gly
305                 310                 315                 320

Ala Gln Lys Phe Val Asp Phe Leu Val Ser Thr Glu Gln Gln Lys Ala
                325                 330                 335

Phe Tyr Asp Ala Thr Asn Glu Ile Pro Ala Asn Thr Glu Ala Arg Ser
            340                 345                 350

Tyr Ala Glu Gly Lys Asn Asp Glu Leu Thr Thr Ala Val Ile Lys Gln
        355                 360                 365

Phe Lys Asn Ala Gln Pro Ile Pro Asn Ile Ser Gln Met Ser Ala Val
    370                 375                 380

Trp Glu Pro Ala Ala Asn Met Leu Phe Asp Thr Val Ser Gly Gln Lys
385                 390                 395                 400

Asp Ala Lys Thr Ala Ala Asn Asp Ala Val Thr Leu Ile Lys Glu Thr
                405                 410                 415

Ile Lys Gln Lys Phe Gly Glu
            420


<210> SEQ ID NO 48
<211> LENGTH: 315
<212> TYPE: PRT
<213> ORGANISM: Streptococcus pyogenes

<400> SEQUENCE: 48

Met Lys Thr Ser Arg Lys Ile Leu Thr Gly Val Val Thr Val Ala Ser
1               5                   10                  15

Val Leu Thr Leu Ala Ala Cys His Ser Thr Ser Glu Gly Thr Asn Val
            20                  25                  30
```

```
Ile Thr Met Lys Asp Asp Thr Ile Thr Val Ser Asp Phe Tyr Asn Glu
        35                  40                  45

Ala Lys Asn Ser Ser Ala Ala Gln Gln Ser Met Leu Asn Leu Val Leu
    50                  55                  60

Ser Arg Val Phe Glu Ser Gln Tyr Gly Lys Gln Val Ser Glu Lys Glu
65                  70                  75                  80

Val Lys Gln Ser Tyr Asp Lys Thr Ala Lys Gln Tyr Gly Ser Ser Phe
                85                  90                  95

Ser Gly Ala Leu Gln Gln Ala Gly Leu Thr Pro Glu Thr Tyr Lys Lys
            100                 105                 110

Gln Ile Arg Thr Thr Met Leu Val Glu His Ala Val Lys Lys Ala Ala
        115                 120                 125

Lys Lys Glu Leu Thr Asp Lys Asn Tyr Glu Lys Ala Tyr Lys Asp Tyr
    130                 135                 140

Thr Pro Ser Met Thr Thr Gln Val Met Ala Leu Asn Asp Glu Glu Lys
145                 150                 155                 160

Ala Lys Lys Ala Leu Asp Asp Val Lys Ala Glu Gly Ala Asp Phe Ala
                165                 170                 175

Ala Ile Ala Lys Asp Lys Thr Thr Ala Ala Asn Lys Lys Ile Asp Tyr
            180                 185                 190

Thr Phe Asp Ser Ala Ser Thr Thr Leu Pro Ser Glu Val Ile Lys Ala
        195                 200                 205

Ala Ser Lys Leu Lys Glu Gly Asp His Ser Glu Val Ile Thr Val Leu
    210                 215                 220

Asp Ser Ala Thr Tyr Gln Lys Lys Phe Tyr Ile Val Lys Val Leu Lys
225                 230                 235                 240

Lys Ala Glu Lys Lys Ala Asp Trp Lys Ser Ser Lys Pro Arg Leu Lys
                245                 250                 255

Glu Ile Ile Leu Lys Glu Lys Thr Asn Asp Thr Asn Phe Gln Asn Lys
            260                 265                 270

Val Ile Ser Ser Ala Leu Asp Lys Ala Asn Val Lys Ile Lys Asp Lys
        275                 280                 285

Ala Phe Ala Asn Ile Leu Ala Gln Phe Ala Ser Lys Lys Asp Thr Lys
    290                 295                 300

Ala Asn Asn Asn Leu Gly Thr Pro Val Gly Gln
305                 310                 315


<210> SEQ ID NO 49
<211> LENGTH: 333
<212> TYPE: PRT
<213> ORGANISM: Streptococcus suis

<400> SEQUENCE: 49

Met Lys Gln Thr Lys Lys Ile Leu Ala Gly Ala Val Thr Leu Phe Ala
1               5                   10                  15

Ala Val Thr Leu Ala Ala Cys Ser Asn Ala Ala Asp Lys Asp Ile Ile
            20                  25                  30

Thr Met Lys Gly Asn Thr Ile Thr Val Ser Glu Phe Tyr Glu Lys Val
        35                  40                  45

Lys Thr Asn Ser Gln Ala Gln Gln Val Leu Leu Ser Met Val Ile Ser
    50                  55                  60

Asn Val Phe Glu Asn Gln Tyr Gly Asp Lys Val Ser Ala Glu Glu Val
65                  70                  75                  80

Asn Lys Glu Tyr Asp Lys Lys Ala Glu Gln Leu Gly Ala Ser Phe Asn
                85                  90                  95
```

```
Ala Ala Leu Ser Ser Ala Gly Leu Thr Glu Glu Ser Tyr Lys Glu Gln
            100                 105                 110

Ile Arg Thr Asn Lys Leu Val Glu Tyr Ala Val Lys Gln Ala Ala Glu
        115                 120                 125

Lys Glu Leu Thr Asp Glu Asn Tyr Lys Ala Ala Tyr Asp Ala Tyr Thr
    130                 135                 140

Pro Glu Val Thr Ala Arg Val Ile Lys Leu Ala Asp Glu Ala Lys Ala
145                 150                 155                 160

Lys Glu Val Leu Ala Ala Ala Gln Ala Glu Gly Ala Asp Phe Ala Gln
                165                 170                 175

Leu Ala Lys Asp Asn Ser Thr Asp Thr Thr Thr Lys Asp Asn Gly Gly
            180                 185                 190

Glu Val Lys Phe Asp Ser Thr Ser Thr Thr Val Pro Ala Glu Val Gln
        195                 200                 205

Lys Ala Val Phe Ala Leu Asp Ala Gly Gln Val Gly Ala Ser Val Ile
    210                 215                 220

Ser Ser Val Asp Met Lys Thr Tyr Thr Thr Ser Tyr Tyr Val Val Lys
225                 230                 235                 240

Leu Asp Ala Lys Ser Glu Lys Ser Ala Lys Trp Glu Asp Tyr Lys Asp
                245                 250                 255

Lys Leu Lys Glu Ile Ile Leu Ala Gln Lys Gln Arg Asp Ser Ser Phe
            260                 265                 270

Val Ala Thr Val Leu Lys Glu Ala Leu Gln Lys Ala Asn Val Lys Val
        275                 280                 285

Lys Asp Ser Ala Phe Gln Asn Leu Leu Ser Gln Tyr Val Thr Thr Glu
    290                 295                 300

Glu Ser Ser Ser Ser Ser Thr Lys Ser Ser Ser Ser Ser Thr Glu Ser
305                 310                 315                 320

Ser Ser Ser Thr Thr Glu Ser Ser Ser Ser Ser Gly Gln
                325                 330


<210> SEQ ID NO 50
<211> LENGTH: 333
<212> TYPE: PRT
<213> ORGANISM: Streptococcus equi

<400> SEQUENCE: 50

Met Lys Arg Ser Thr Lys Leu Leu Ala Gly Ile Val Thr Leu Ala Ser
1               5                   10                  15

Ala Met Thr Leu Ala Ala Cys Gln Ser Thr Asn Asp Asn Thr Ser Val
            20                  25                  30

Ile Thr Met Lys Gly Asp Thr Ile Ser Val Ser Asp Phe Tyr Asn Glu
        35                  40                  45

Thr Lys Asn Thr Glu Val Ser Gln Arg Ala Met Leu Asn Leu Val Val
    50                  55                  60

Ser Arg Val Phe Glu Asp Gln Tyr Gly Lys Lys Val Ser Lys Lys Lys
65                  70                  75                  80

Thr Glu Glu Ala Tyr Asn Lys Ser Ala Glu Gln Tyr Gly Ala Ser Phe
                85                  90                  95

Ser Ala Ala Leu Ala Gln Ser Gly Leu Thr Thr Asp Thr Tyr Lys Arg
            100                 105                 110

Gln Ile Arg Ser Ala Met Leu Val Glu Tyr Ala Val Lys Glu Ala Ala
        115                 120                 125

Lys Lys Glu Leu Thr Asp Ala Asp Tyr Lys Lys Ala Tyr Glu Ser Tyr
```

```
    130                 135                 140

Thr Pro Glu Met Thr Thr Gln Val Ile Thr Leu Asp Asn Glu Glu Thr
145                 150                 155                 160

Ala Lys Ala Val Leu Gly Glu Val Lys Ala Glu Gly Ala Asp Phe Ala
                165                 170                 175

Ala Ile Ala Lys Glu Lys Thr Thr Ala Ala Asp Lys Lys Val Asp Tyr
            180                 185                 190

Lys Phe Asp Ser Gly Asp Thr Lys Leu Pro Ala Asp Val Ile Lys Ala
        195                 200                 205

Ala Ser Gly Leu Lys Glu Gly Asp Ile Ser Glu Val Val Ser Val Leu
    210                 215                 220

Asp Pro Ala Thr Tyr Gln Asn Lys Phe Tyr Ile Val Lys Val Thr Lys
225                 230                 235                 240

Lys Ala Glu Lys Ala Ser Asp Trp Lys Lys Tyr Lys Lys Arg Leu Lys
                245                 250                 255

Glu Ile Val Leu Ala Glu Lys Thr Gln Asn Ile Asp Phe Gln Asn Lys
            260                 265                 270

Val Ile Ala Lys Ala Leu Asp Lys Ala Asn Val Lys Ile Lys Asp Gln
        275                 280                 285

Ala Phe Ala Asn Ile Leu Ala Gln Tyr Ala Asn Thr Asp Lys Lys Ala
    290                 295                 300

Ser Lys Ala Asn Thr Ser Lys Ser Asp Gln Lys Ser Ser Ser Asp Ser
305                 310                 315                 320

Ser Lys Asp Ser Gln Ser Ser Lys Ser Lys Ser Glu Lys
                325                 330


<210> SEQ ID NO 51
<211> LENGTH: 312
<212> TYPE: PRT
<213> ORGANISM: Streptococcus mitis

<400> SEQUENCE: 51

Met Lys Lys Lys Leu Leu Ala Gly Ala Ile Thr Leu Leu Ser Val Ala
1               5                   10                  15

Thr Leu Ala Ala Cys Ser Lys Gly Ser Glu Gly Ala Asp Leu Ile Ser
            20                  25                  30

Met Lys Gly Asp Val Ile Thr Glu His Gln Phe Tyr Glu Gln Val Lys
        35                  40                  45

Ser Asn Pro Ser Ala Gln Gln Val Leu Leu Asn Leu Thr Ile Gln Lys
    50                  55                  60

Val Phe Glu Lys Gln Tyr Gly Ser Glu Val Asp Asp Lys Glu Val Asn
65                  70                  75                  80

Asp Thr Ile Ala Glu Glu Glu Lys Gln Tyr Gly Glu Asn Tyr Gln Arg
                85                  90                  95

Val Leu Ser Gln Ala Gly Met Thr Leu Glu Thr Arg Lys Ala Gln Ile
            100                 105                 110

Arg Thr Ser Lys Leu Val Glu Leu Ala Val Lys Lys Ala Ala Glu Ala
        115                 120                 125

Glu Leu Thr Asp Asp Ala Tyr Lys Lys Ala Phe Asp Glu Tyr Thr Pro
    130                 135                 140

Asp Val Thr Ala Gln Ile Ile Arg Leu Asp Asn Glu Asp Lys Ala Lys
145                 150                 155                 160

Glu Ile Leu Glu Lys Ala Lys Ala Ser Asp Ala Asp Phe Ala Gln Leu
                165                 170                 175
```

```
Ala Lys Asp Asn Ser Thr Asp Glu Lys Thr Lys Ala Asn Gly Gly Glu
            180                 185                 190

Ile Thr Phe Asp Ser Ala Ser Thr Glu Val Pro Glu Gln Val Lys Lys
        195                 200                 205

Ala Ala Phe Ala Leu Asp Val Asn Gly Ile Ser Asp Val Ile Ser Val
    210                 215                 220

Thr Gly Thr Gln Ala Tyr Ser Ser Gln Tyr Tyr Ile Val Lys Leu Ile
225                 230                 235                 240

Lys Lys Thr Glu Lys Ser Ser Asn Ile Asp Asp Tyr Lys Glu Lys Leu
                245                 250                 255

Lys Thr Val Ile Leu Thr Gln Lys Gln Asn Asp Ala Ser Phe Val Gln
            260                 265                 270

Ser Ile Ile Gly Lys Glu Leu Gln Ala Ala Asn Ile Lys Val Lys Asp
        275                 280                 285

Gln Ala Phe Gln Asn Ile Phe Thr Gln Tyr Ile Gly Gly Gly Asp Ser
    290                 295                 300

Ser Ser Ser Ser Ser Ser Lys Glu
305                 310


<210> SEQ ID NO 52
<211> LENGTH: 333
<212> TYPE: PRT
<213> ORGANISM: Streptococcus mutans

<400> SEQUENCE: 52

Met Lys Lys Arg Thr Ile Ala Thr Gly Leu Val Thr Leu Leu Ser Ile
1               5                   10                  15

Val Thr Leu Ala Ala Cys Ser Lys Thr Asn Gln Asn Ser Lys Ile Ala
            20                  25                  30

Thr Met Lys Gly Asp Thr Ile Thr Val Ala Asp Phe Tyr Asn Glu Val
        35                  40                  45

Lys Asn Ser Thr Ala Ser Lys Gln Ala Val Leu Ser Leu Leu Val Ser
    50                  55                  60

Lys Val Phe Glu Lys Gln Tyr Gly Asp Lys Val Ser Asp Lys Glu Val
65                  70                  75                  80

Thr Lys Ala Tyr Asn Glu Ala Ala Lys Tyr Tyr Gly Asp Ser Phe Ser
                85                  90                  95

Ser Ala Leu Ala Ser Arg Gly Tyr Thr Lys Glu Asp Tyr Lys Lys Gln
            100                 105                 110

Ile Arg Ser Glu Lys Leu Ile Glu Tyr Ala Val Lys Glu Glu Ala Lys
        115                 120                 125

Lys Glu Ile Thr Asp Ala Ser Tyr Lys Ser Ala Tyr Lys Asp Tyr Lys
    130                 135                 140

Pro Glu Val Thr Ala Gln Val Ile Gln Leu Asp Ser Glu Asp Lys Ala
145                 150                 155                 160

Lys Ser Val Leu Glu Glu Ala Lys Ala Asp Gly Ala Asp Phe Ala Lys
                165                 170                 175

Ile Ala Lys Asp Asn Thr Lys Gly Asp Lys Thr Glu Tyr Ser Phe Asp
            180                 185                 190

Ser Gly Ser Thr Asn Leu Pro Ser Gln Val Leu Ser Ala Ala Leu Asn
        195                 200                 205

Leu Asp Lys Asp Gly Val Ser Asp Val Ile Lys Ala Ser Asp Ser Thr
    210                 215                 220

Thr Tyr Lys Pro Val Tyr Tyr Ile Val Lys Ile Thr Lys Lys Thr Asp
225                 230                 235                 240
```

```
Lys Asn Ala Asp Trp Lys Ala Tyr Lys Lys Arg Leu Lys Glu Ile Ile
                245                 250                 255

Val Ser Gln Lys Leu Asn Asp Ser Asn Phe Arg Asn Ala Val Ile Gly
            260                 265                 270

Lys Ala Phe Lys Lys Ala Asn Val Lys Ile Lys Asp Lys Ala Phe Ser
        275                 280                 285

Glu Ile Leu Ser Gln Tyr Ala Ala Ala Ser Gly Ser Gly Ser Ser Gly
    290                 295                 300

Ser Thr Thr Thr Thr Thr Ala Ala Ser Ser Ala Ala Thr Thr Ala Ala
305                 310                 315                 320

Asp Asp Gln Thr Thr Ala Ala Glu Thr Thr Ala Ala Glu
                325                 330


<210> SEQ ID NO 53
<211> LENGTH: 312
<212> TYPE: PRT
<213> ORGANISM: Streptococcus pseudopneumoniae

<400> SEQUENCE: 53

Met Lys Lys Lys Leu Leu Ala Gly Ala Ile Thr Leu Leu Ser Val Ala
1               5                   10                  15

Thr Leu Ala Ala Cys Ser Lys Gly Ser Glu Gly Ala Asp Leu Ile Ser
            20                  25                  30

Met Lys Gly Asp Val Ile Thr Glu His Gln Phe Tyr Glu Gln Val Lys
        35                  40                  45

Ser Asn Pro Ser Ala Gln Gln Val Leu Leu Asn Met Thr Ile Gln Lys
    50                  55                  60

Val Phe Glu Lys Gln Tyr Gly Ser Glu Leu Asp Asp Lys Glu Val Asp
65                  70                  75                  80

Asp Thr Ile Ala Glu Glu Glu Lys Gln Tyr Gly Glu Asn Tyr Gln Arg
                85                  90                  95

Val Leu Ser Gln Ala Gly Met Thr Leu Glu Thr Arg Lys Ala Gln Ile
            100                 105                 110

Arg Thr Ser Lys Leu Val Glu Leu Ala Val Lys Lys Ala Ala Glu Ala
        115                 120                 125

Glu Leu Thr Asp Asp Ala Tyr Lys Lys Ala Phe Asp Glu Tyr Thr Pro
    130                 135                 140

Asp Val Thr Val Gln Ile Ile Arg Leu Asp Asn Glu Asp Lys Ala Lys
145                 150                 155                 160

Glu Val Leu Glu Lys Ala Lys Ala Glu Gly Ala Asp Phe Ala Gln Leu
                165                 170                 175

Ala Lys Asp Asn Ser Thr Asp Glu Lys Thr Lys Ala Asn Gly Gly Glu
            180                 185                 190

Ile Thr Phe Asp Ser Ala Ser Thr Glu Val Pro Glu Gln Val Lys Lys
        195                 200                 205

Ala Ala Phe Ala Leu Asp Val Asn Gly Ile Ser Asp Val Ile Thr Ala
    210                 215                 220

Thr Gly Thr Gln Ala Tyr Ser Ser Gln Tyr Tyr Ile Val Lys Leu Ile
225                 230                 235                 240

Lys Lys Thr Glu Lys Ser Ser Asn Ile Asp Asp Tyr Lys Glu Lys Leu
                245                 250                 255

Lys Thr Val Ile Leu Thr Gln Lys Gln Asn Asp Ser Thr Phe Val Gln
            260                 265                 270

Ser Ile Ile Gly Lys Glu Leu Gln Ala Ala Asn Ile Lys Val Lys Asp
```

```
        275                 280                 285

Gln Ala Phe Gln Asn Ile Phe Thr Gln Tyr Ile Gly Gly Gly Asp Ser
    290                 295                 300

Ser Ser Ser Ser Ser Ser Lys Glu
305                 310


<210> SEQ ID NO 54
<211> LENGTH: 23
<212> TYPE: DNA
<213> ORGANISM: Artificial
<220> FEATURE:
<223> OTHER INFORMATION: Synthetic primer

<400> SEQUENCE: 54

gactagcaaa tactaacaac aag                                              23


<210> SEQ ID NO 55
<211> LENGTH: 18
<212> TYPE: DNA
<213> ORGANISM: Artificial
<220> FEATURE:
<223> OTHER INFORMATION: Synthetic primer

<400> SEQUENCE: 55

ggatccgtcg acctgcag                                                    18


<210> SEQ ID NO 56
<211> LENGTH: 47
<212> TYPE: DNA
<213> ORGANISM: Artificial
<220> FEATURE:
<223> OTHER INFORMATION: Synthetic primer

<400> SEQUENCE: 56

cttgttgtta gtatttgcta gtcgaattcg aaaagccctg acaacgc                    47


<210> SEQ ID NO 57
<211> LENGTH: 43
<212> TYPE: DNA
<213> ORGANISM: Artificial
<220> FEATURE:
<223> OTHER INFORMATION: Synthetic primer

<400> SEQUENCE: 57

ctgcaggtcg acggatccaa catcattgtc attcatattt ttc                        43


<210> SEQ ID NO 58
<211> LENGTH: 37
<212> TYPE: DNA
<213> ORGANISM: Artificial
<220> FEATURE:
<223> OTHER INFORMATION: Synthetic primer

<400> SEQUENCE: 58

gggaggccaa atataatgaa gaaaaaatta ttggcag                               37


<210> SEQ ID NO 59
<211> LENGTH: 43
<212> TYPE: DNA
<213> ORGANISM: Artificial
<220> FEATURE:
<223> OTHER INFORMATION: Synthetic primer

<400> SEQUENCE: 59

gacatagtgt attcctccta aatggactat tcgtttgatg tac                        43
```

<210> SEQ ID NO 60
<211> LENGTH: 43
<212> TYPE: DNA
<213> ORGANISM: Artificial
<220> FEATURE:
<223> OTHER INFORMATION: Synthetic primer

<400> SEQUENCE: 60
gtacatcaaa cgaatagtcc atttaggagg aatacactat gtc 43

<210> SEQ ID NO 61
<211> LENGTH: 39
<212> TYPE: DNA
<213> ORGANISM: Artificial
<220> FEATURE:
<223> OTHER INFORMATION: Synthetic primer

<400> SEQUENCE: 61
aagcggaaga gcgtctatct ctattgataa attcaaagg 39

<210> SEQ ID NO 62
<211> LENGTH: 18
<212> TYPE: DNA
<213> ORGANISM: Artificial
<220> FEATURE:
<223> OTHER INFORMATION: Synthetic primer

<400> SEQUENCE: 62
tagacgctct tccgcttc 18

<210> SEQ ID NO 63
<211> LENGTH: 19
<212> TYPE: DNA
<213> ORGANISM: Artificial
<220> FEATURE:
<223> OTHER INFORMATION: Synthetic primer

<400> SEQUENCE: 63
tcattatatt tggcctccc 19

<210> SEQ ID NO 64
<211> LENGTH: 5943
<212> TYPE: DNA
<213> ORGANISM: Artificial
<220> FEATURE:
<223> OTHER INFORMATION: Artificial vector

<400> SEQUENCE: 64
aactaactca acgctagtag tggatttaat cccaaatgag ccaacagaac cagaaccaga 60
aacagaatca gaacaagtaa cattggattt agaaatggaa gaagaaaaaa gcaatgactt 120
cgtgtgaata atgcacgaaa tcgttgctta tttttttaa aagcggtata ctagatataa 180
cgaaacaacg aactgaatag aaacgaaaaa agagccatga cacatttata aaatgtttga 240
cgacatttta taaatgcata gcccgataag attgccaaac caacgcttat cagttagtca 300
gatgaactct tccctcgtaa gaagttattt aattaacttt gtttgaagac ggtatataac 360
cgtactatca ttatataggg aaatcagaga gttttcaagt atctaagcta ctgaatttaa 420
gaattgttaa gcaatcaatc ggaaatcgtt tgattgcttt ttttgtattc atttatagaa 480
ggtggagttt gtatgaatca tgatgaatgt aaaacttata taaaaaatag tttattggag 540
ataagaaaat tagcaaatat ctatacacta gaaacgttta agaaagagtt agaaaagaga 600

-continued

```
aatatctact tagaaacaaa atcagataag tatttttctt cggaggggga agattatata    660
tataagttaa tagaaaataa caaaataatt tattcgatta gtggaaaaaa attgacttat    720
aaaggaaaaa aatctttttc aaaacatgca atattgaaac agttgaatga aaaagcaaac    780
caagttaatt aaacaaccta ttttatagga tttataggaa aggagaacag ctgaatgaat    840
atccctttg ttgtagaaac tgtgcttcat gacggcttgt taaagtacaa atttaaaaat    900
agtaaaattc gctcaatcac taccaagcca ggtaaaagca aaggggctat ttttgcgtat    960
cgctcaaaat caagcatgat tggcggtcgt ggtgttgttc tgacttccga ggaagcgatt   1020
caagaaaatc aagatacatt tacacattgg acacccaacg tttatcgtta tggaacgtat   1080
gcagacgaaa accgttcata cacgaaagga cattctgaaa acaatttaag acaaatcaat   1140
accttcttta ttgattttga tattcacacg gcaaaagaaa ctatttcagc aagcgatatt   1200
ttaacaaccg ctattgattt aggttttatg cctactatga ttatcaaatc tgataaaggt   1260
tatcaagcat attttgtttt agaaacgcca gtctatgtga cttcaaaatc agaatttaaa   1320
tctgtcaaag cagccaaaat aatttcgcaa aatatccgag aatattttgg aaagtctttg   1380
ccagttgatc taacgtgtaa tcattttggt attgctcgca taccaagaac ggacaatgta   1440
gaattttttg atcctaatta ccgttattct ttcaaagaat ggcaagattg gtctttcaaa   1500
caaacagata ataagggctt tactcgttca agtctaacgg ttttaagcgg tacagaaggc   1560
aaaaaacaag tagatgaacc ctggtttaat ctcttattgc acgaaacgaa attttcagga   1620
gaaaagggtt taatagggcg taataacgtc atgtttaccc tctctttagc ctactttagt   1680
tcaggctatt caatcgaaac gtgcgaatat aatatgtttg agtttaataa tcgattagat   1740
caacccttag aagaaaaaga agtaatcaaa attgttagaa gtgcctattc agaaaactat   1800
caaggggcta atagggaata cattaccatt ctttgcaaag cttgggtatc aagtgattta   1860
accagtaaag atttatttgt ccgtcaaggg tggtttaaat tcaagaaaaa aagaagcgaa   1920
cgtcaacgtg ttcatttgtc agaatggaaa gaagatttaa tggcttatat tagcgaaaaa   1980
agcgatgtat acaagcctta tttagtgacg accaaaaaag agattagaga agtgctaggc   2040
attcctgaac ggacattaga taaattgctg aaggtactga aggcgaatca ggaaattttc   2100
tttaagatta aaccaggaag aaatggtggc attcaacttg ctagtgttaa atcattgttg   2160
ctatcgatca ttaaagtaaa aaaagaagaa aaagaaagct atataaaggc gctgacaaat   2220
tcttttgact tagagcatac attcattcaa gagactttaa acaagctagc agaacgccct   2280
aaaacggaca cacaactcga tttgtttagc tatgatacag gctgaaaata aaacccgcac   2340
tatgccatta catttatatc tatgatacgt gtttgttttt tctttgctgt ttagcgaatg   2400
attagcagaa atatacagag taagatttta attaattatt aggggggagaa ggagagagta   2460
gcccgaaaac ttttagttgg cttggactga acgaagtgag ggaaaggcta ctaaaacgtc   2520
gaggggcagt gagagcgaag cgaacacttg atttttttaat tttctatctt ttataggtca   2580
ttagagtata cttatttgtc ctataaacta tttagcagca taatagattt attgaatagg   2640
tcatttaagt tgagcatatt agaggaggaa aatcttggag aaatatttga agaacccgat   2700
tacatggatt ggattagttc ttgtggttac gtggttttta actaaaagta gtgaattttt   2760
gatttttggt gtgtgtgtct tgttgttagt atttgctagt cgaattcgaa aagccctgac   2820
aacccttgtt cctaaaaagg aataagcgtt cggtcagtaa ataatagaaa taaaaaatca   2880
gacctaagac tgatgacaaa aagagaaaat tttgataaaa tagtcttaga attaaattaa   2940
aaagggaggc caaatataat gaaaaatatg aatgacaatg atgttggatc cgtcgacctg   3000
```

```
cagccaagct tatcgattct agacgctctt ccgcttcctc gctcactgac tcgctgcgct   3060

cggtcgttcg gctgcggcga gcggtatcag ctcactcaaa ggcggtaata cggttatcca   3120

cagaatcagg ggataacgca ggaaagaaca tgtgagcaaa aggccagcaa aaggccagga   3180

accgtaaaaa ggccgcgttg ctggcgtttt tccataggct ccgcccccct gacgagcatc   3240

acaaaaatcg acgctcaagt cagaggtggc gaaacccgac aggactataa agataccagg   3300

cgtttccccc tggaagctcc ctcgtgcgct ctcctgttcc gaccctgccg cttaccggat   3360

acctgtccgc ctttctccct tcgggaagcg tggcgctttc tcatagctca cgctgtaggt   3420

atctcagttc ggtgtaggtc gttcgctcca agctgggctg tgtgcacgaa ccccccgttc   3480

agcccgaccg ctgcgcctta tccggtaact atcgtcttga gtccaacccg gtaagacacg   3540

acttatcgcc actggcagca gccactggta acaggattag cagagcgagg tatgtaggcg   3600

gtgctacaga gttcttgaag tggtggccta actacggcta cactagaaga acagtatttg   3660

gtatctgcgc tctgctgaag ccagttacct tcggaaaaag agttggtagc tcttgatccg   3720

gcaaacaaac caccgctggt agcggtggtt tttttgtttg caagcagcag attacgcgca   3780

gaaaaaaagg atctcaagaa gatcctttga tcttttctac ggggtctgac gctcagtgga   3840

acgaaaactc acgttaaggg attttggtca tgagattatc aaaaaggatc ttcacctaga   3900

tccttttaaa ttaaatctag aatcgatacg attttgaagt ggcaacagat aaaaaaaagc   3960

agtttaaaat tgttgctgaa cttttaaaac aagcaaatac aatcattgtc gcaacagata   4020

gcgacagaga aggcgaaaac attgcctggt cgatcattca taaagcaaat gccttttcta   4080

aagataaaac gtataaaaga ctatggatca atagtttaga aaaagatgtg atccgtagcg   4140

gttttcaaaa tttgcaacca ggaatgaatt actatccctt ttatcaagaa gcgcacaaaa   4200

agaaaaacga aatgatacac caatcagtgc aaaaaaagat ataatgggag ataagacggt   4260

tcgtgttcgt gctgacttgc accatatcat aaaaatcgaa acagcaaaga atggcggaaa   4320

cgtaaaagaa gttatggaaa taagacttag aagcaaactt aagagtgtgt tgatagtgca   4380

gtatcttaaa attttgtata ataggaattg aagttaaatt agatgctaaa aatttgtaat   4440

taagaaggag tgattacatg aacaaaaata taaaatattc tcaaaacttt ttaacgagtg   4500

aaaaagtact caaccaaata ataaaacaat tgaatttaaa agaaaccgat accgtttacg   4560

aaattggaac aggtaaaggg catttaacga cgaaactggc taaaataagt aaacaggtaa   4620

cgtctattga attagacagt catctattca acttatcgtc agaaaaatta aaactgaata   4680

ctcgtgtcac tttaattcac caagatattc tacagtttca attccctaac aaacagaggt   4740

ataaaattgt tgggagtatt ccttaccatt taagcacaca aattattaaa aaagtggttt   4800

ttgaaagcca tgcgtctgac atctatctga ttgttgaaga aggattctac aagcgtacct   4860

tggatattca ccgaacacta gggttgctct tgcacactca agtctcgatt cagcaattgc   4920

ttaagctgcc agcggaatgc tttcatccta aaccaaaagt aaacagtgtc ttaataaaac   4980

ttacccgcca taccacagat gttccagata aatattggaa gctatatacg tactttgttt   5040

caaaatgggt caatcgagaa tatcgtcaac tgtttactaa aaatcagttt catcaagcaa   5100

tgaaacacgc caaagtaaac aatttaagta ccgttactta tgagcaagta ttgtctattt   5160

ttaatagtta tctattattt aacgggagga aataattcta tgagtcgctt ttgtaaattt   5220

ggaaagttac acgttactaa agggaatgta gataaattat taggtatact actgacagct   5280

tccaaggagc taaagaggtc cctagcgctc ttatcatggg gaagctcgga tcatatgcaa   5340
```

-continued

```
gacaaaataa actcgcaaca gcacttggag aaatgggacg aatcgagaaa accctcttta   5400

cgctggatta catatctaat aaagccgtaa ggagacgggt tcaaaaaggt ttaaataaag   5460

gagaagcaat caatgcatta gctagaatta tattttttgg acaacgtgga gaatttagag   5520

aacgtgctct ccaagaccag ttacaaagag ctagtgcact aaacataatt attaacgcta   5580

taagtgtgtg gaacactgta tatatggaaa aagccgtaga agaattaaaa gcaagaggag   5640

aatttagaga agatttaatg ccatatgcgt ggccgttagg atgggaacat atcaattttc   5700

ttggagaata caaatttgaa ggattacatg acactgggca aatgaattta cgtcctttac   5760

gtataaaaga gccgttttat tcttaatata acggctcttt ttatagaaaa aatccttagc   5820

gtggtttttt tccgaaatgc tggcggtacc ccaagaatta gaaatgagta gatcaaatta   5880

ttcacgaata gaatcaggaa aatcagatcc aaccataaaa acactagaac aaattgcaaa   5940

gtt                                                                 5943
```

STREPTOCOCCAL VACCINES

CROSS-REFERENCE TO RELATED APPLICATIONS

This application is a National Stage application under 35 U.S.C. § 371 of International Application No. PCT/EP2021/069352, having an International Filing Date of Jul. 12, 2021, which claims priority to Swedish Application Serial No. 2050901-4, filed on Jul. 16, 2020. The disclosure of the prior application is considered part of the disclosure of this application, and is incorporated in its entirety into this application.

SEQUENCE LISTING

This application contains a Sequence Listing that has been submitted electronically as an ASCII text file named "55867-0004US1SEQ.txt." The ASCII text file, created on Dec. 19, 2022, is 148,020 bytes in size. The material in the ASCII text file is hereby incorporated by reference in its entirety.

TECHNICAL FIELD

The present invention relates to the field of vaccines against *Streptococcus pneumoniae* and other streptococci, in particular serotype-independent vaccines against *Streptococcus pneumoniae.*

BACKGROUND TO THE INVENTION

*Streptococcus pneumoniae* (the pneumococcus) is a major cause of morbidity and mortality globally. It is the most common cause of common respiratory tract infections such as otitis and sinusitis, but also a major contributor to more severe diseases including pneumonia, as well as sepsis and meningitis, i.e., invasive pneumococcal disease (IPD). Risk groups include young children and the elderly as well as immunocompromised individuals. Also, it has been shown that influenza virus infections also predispose for pneumococcal infections. Even though pneumococci cause infections with sometimes lethal outcomes, pneumococci normally colonize healthy children in the nasopharynx from where they may spread to susceptible individuals. Several pneumococcal virulence factors have been described and a major one is the polysaccharide capsule. So far 100 different so-called capsular serotypes have been identified depending on structural differences in the capsular polysaccharide. Current pneumococcal vaccines target a limited number of these capsules either as a polysaccharide-based vaccine (PPV23) targeting 23 different capsular serotypes, or as so called pneumococcal conjugated vaccines (PCVs), where a protein has been coupled to the sugar to get a better immune response especially in the risk groups. First, a 7-valent vaccine (PCV7) was launched that was changed to either a 10-valent (PCV10) or 13-valent vaccine (PCV13) around year 2010. PCVs have been introduced in childhood vaccination programs in many countries world-wide and have resulted in significant decreases in the number of IPD cases among vaccinated children. Vaccination has also resulted in an almost complete eradication of vaccine type (VT) strains from the nasopharynx of healthy children. However, this has not decreased pneumococcal carriage rates in children, due to replacement of VT with non-vaccine type strains (NVT). This profound serotype replacement in the carrier population has led to an expansion of NVTs among IPD cases, also in non-vaccinated age groups, affecting the efficacy of the PCVs. In Sweden in 2016, the IPD incidence among the elderly did not decrease post-vaccination, and more than 70% of the IPD cases were caused by NVTs. PCV13 includes additionally 3 serotypes not included in PCV10, i.e. serotypes 3, 6A and 19A. So far, the efficacy against IPD caused by serotype 3 is being debated, and in Sweden, serotype 3 now constitutes a major serotype among IPD cases in the elderly.

Extracellular vesicles (EVs), also termed membrane vesicles (MVs) are membrane-derived vesicles released by bacteria. Pneumococcal EVs have been isolated from liquid cultures previously (Olaya-Abril et al. J. Proteomics. 2014; 106:46-60). EVs have been shown to carry many pneumococcal virulence factors and proteins known to be membrane associated, but also to contain a cytosolic cargo enriched for the LytA autolysin, and the cytotoxin pneumolysin (Codemo et al. MBio. 2018; 9(2)). EVs can be internalized by host cells such as dendritic cells (DCs), and lead to DC activation and release of pro-inflammatory cytokines. In vivo experiments have shown that intramuscular immunization of mice with pneumococcal EVs protect mice after intranasal challenge with the same pneumococcal serotype. It has been demonstrated that pneumococci growing on solid support, mimicking the biofilm mode of growth occurring during natural infection, exhibited a different expression pattern of surface antigens as compared to planktonic growth in liquid culture (WO2018/124959).

Opsonophagocytosis is the primary mechanism for clearance of pneumococci from the host, and the measurement of opsonophagocytic antibodies appears to correlate with vaccine-induced protection. However, it has proven difficult to design vaccines that elicit an efficient response in form of opsonophagocytic antibodies.

Taken together, the above issues stress the need for novel vaccine approaches especially for adults and the elderly, where NVTs now cause the major part of severe pneumococcal infections. Thus, an objective of the present invention is the provision of alternative or improved immunogenic compositions for conferring serotype-independent immunological responses and/or alternative or improved responses in terms of opsonophagocitic antibodies and/or protection in experimental models. Further objects include provision of improved and/or alternative immunogenic compositions relating to streptococcal pathogens.

Definitions

The term membrane vesicles (MVs) refers to membrane-derived vesicles released by bacteria, in particular streptococci, such as *Streptococcus pneumoniae*. The MVs can carry many virulence factors and proteins, both soluble and membrane-associated.

*Streptococcus pneumoniae* membrane vesicle microparticles (MP) refers to membrane vesicle microparticles of a particular type, derived from culture on solid phase medium, as described in WO2018/124959. The MPs have distinct profile of various antigens compared to membrane vesicles of the type generated by bacteria in liquid culture. The term particularly excludes membrane vesicles of the type generated by bacteria in liquid culture.

Antigen refers to structures to which antibodies generated by the adaptive immune system of vertebrates specifically bind. Antigens are often proteins, peptides or polysaccharides (sometimes containing a lipid moiety). In the context of vaccines, an antigen is an ingredient in a vaccine against which a specific antibody response is intended to be elicited in the host to which the vaccine is administered. Some vaccines contain several antigens. In the vaccine context, a vaccine antigen generally bears a structural resemblance to a pathogen antigen present in a pathogen against which the vaccine is intended to be used. A vaccine antigen may be a fragment or a modified version of the pathogen antigen, or a complete pathogen antigen presented in a non-pathogenic form e.g. as an inactivated pathogen or a recombinant protein produced in a non-pathogenic host.

PspA refers to Pneumococcal surface protein A, which is a surface exposed protein that associates with the pneumococcal cell wall via non-covalent affinity binding to phospho-choline residues through its choline binding domain. PspA has been reported to have dual properties. It is a lactoferrin-binding protein and in addition a protein that may prevent complement activation. The sequence of PspA is highly variable in both amino acid sequence and length. PspA has been suggested as a vaccine candidate but the variability of the protein among pneumococcal strains are considered as a limiting factor for cross-protection. In a number of studies PspA has been reported to be an immune-dominant protein that provides immunological protection upon immunization. However, due to the high variability of the protein it is considered to not provide good cross-protection for a diverse set of pneumococcal serotypes or isolates. See Khan N. et al. (Front. Microbiol. 2017 2; 8:742) for a review on PspA. A reference sequence from strain TIGR4 is presented in SEQ ID NO: 27. MalX is a maltose/maltodextrin-binding protein required for the uptake of maltose (a disaccharide of glucose) and maltodextrin (glucose oligosaccharides) from the host environment. Streptococcal MalX homologues are present in most streptococcal species including *Streptococcus pneumoniae, Streptococcus pyogenes, Streptococcus suis, Streptococcus equi, Streptococcus mitis*, and *Streptococcus pseudopneumoniae*. MalX is a lipoprotein and as such attached to a lipid (diacylglycerol) in the outer leaflet of the plasma membrane through covalent thioester bond linkage via its N-terminal cysteine residue of the mature protein. Pneumococcal malX deletion strains have been found attenuated in virulence in mouse model system and were recently identified to induce a $T_H17$ based immune response and immunization provided protection against pneumococcal colonization (Moffitt K. L. et al. Cell Host Microbe 201117; 9(2):158-65). malX is a highly conserved gene that is present in more than 99.6% of the sequenced *S. pneumoniae* strains (n=8351 strains) obtained from PubMLST and has a very high sequence conservation (98.5% of these sequences with >98% sequence identity to the TIGR4 allele on the nucleotide level). A reference sequence from strain *S. pneumoniae* TIGR4 is presented in SEQ ID NO: 25, from *Streptococcus pyogenes* in SEQ ID NO: 43, from *Streptococcus suis* in SEQ ID NO: 44 from *Streptococcus equi* in SEQ ID NO: 45, from *Streptococcus mitis* in SEQ ID NO: 46 and from *Streptococcus pseudopneumoniae* in SEQ ID NO: 47.

PrsA, also termed PpmA in the literature, is also a lipoprotein like MalX (described in the previous section). Streptococcal PrsA homologues are present in most streptococcal species including *Streptococcus pneumoniae, Streptococcus pyogenes, Streptococcus suis, Streptococcus equi, Streptococcus mitis, Streptococcus mutans* and *Streptococcus* pseudopneumoniae. It functions as a Parvulin-like peptidyl-prolyl cis-trans isomerase (PPI), thereby acting as a chaperon that assists secreted proteins to fold properly by catalyzing isomerization of peptidyl bonds preceding proline residues. In addition to the Parvulin-like PPI domain the protein also contains a large N-terminal domain and a short C-terminal domain of unknown function but suggested to be involved in the chaperone function as revealed by the crystal structure of the *Bacillus subtilis* PrsA orthologue (Jakob R. P. et al. J. Biol. Chem. 2015 6; 290(6):3278-92). PrsA-deficient pneumococci have decreased virulent properties and have been shown to contribute to nasal colonization and to early stages of infection. Immunization of mice with the avirulent pneumococcal strain T4Δpab induced antibody responses against several antigens including PrsA (Chimalapati S. et al. Infect. Immun. 201179(12):4965-76). However, this type of immunization provided poor cross-protection. Immunization with an orthologue of PrsA from *Streptococcus suis* was reported to provide good cross-protection against different *S. suis* serotypes in a murine model (Ref: PMID 30629173). prsA is a highly conserved gene that is present in more than 99.6% of the sequenced *S. pneumoniae* strains (n=8351 strains) obtained from PubMLST and has a very high a sequence conservation (99.5% of these sequences with >98% sequence identity to the TIGR4 allele on the nucleotide level). A reference sequence from strain TIGR4 is provided in SEQ ID NO: 26, from *Streptococcus pyogenes* in SEQ ID NO: 48, from *Streptococcus suis* in SEQ ID NO: 49, from *Streptococcus equi* in SEQ ID NO: 50, from *Streptococcus mitis* in SEQ ID NO: 51, from *Streptococcus mutans* in SEQ ID NO: 52 and from *Streptococcus pseudopneumoniae* in SEQ ID NO: 53.

Pneumolysin (termed Ply herein) is a 53 kDa cholesterol dependent cytolysin released by *Streptococcus pneumoniae* upon lysis. It is one of the major virulence factors of this bacterium. It forms pores in all eukaryotic cells that have cholesterol in their membranes. The formation of pores by Ply frequently results in host cell death as membrane integrity is destroyed. Ply plays a central role in protecting the pneumococcus from complement attack and aiding its spread to other tissues/organs. Ply is able to activate the classical complement pathway, even in the absence of Ply specific antibody (Mitchell T. J. et al. Subcell. Biochem. 2014; 80:145-60). A reference sequence from strain TIGR4 is presented in SEQ ID NO: 28. LytA is the major autolysin of *Streptococcus pneumoniae*. Lysis is caused by cleaving the lactyl-amide bond between the stem peptides and the glycan strands of peptidoglycan, resulting in hydrolysis of the cell wall. LytA is considered as a virulence factor since lytA deficient pneumococci are much less virulent in a murine infection model (Canvi J. R. et al J. Infect. Dis. 1995 172(1):119-23). However, the explicit contribution of LytA to pneumococcal virulence is still unclear. It is possible that LytA-mediated lysis releases other virulence factors such as pneumolysin. LytA could also be released to lyse neighbouring non-competent pneumococcal cells in a fratricidal manner. This would potentially facilitate genetic exchange between naturally competent pneumococcal populations that easily take up and incorporate DNA by homologous recombination. A third possibility is that LytA mediates lysis to release proteins involved in immune evasion or cell wall components that may interfere with the host immune response (Mellroth et al. J Biol Chem. 2012; 287(14):11018-29.). A reference sequence from strain TIGR4 is presented in SEQ ID NO: 29.

PspC/CbpA (choline binding protein A) is a protein that binds the phosphocholine present in the teichoic acid and the lipoteichoic acid of the cell membrane and the cell wall. It is a major pneumococcal adhesin. It promotes pneumococcal adherence via a human-specific interaction with the ectodomain of the polymeric Ig receptor. It also prevents activation of C3b and complement-mediated opsonophagocytosis of pneumococci (Bergmann& Hammerschmidt Microbiology. 2006; 152(Pt 2):295-303.). The pspC locus is highly polymorphic and 11 major groups of this protein have been identified. Single PspC proteins are identified by sequential numbers separated from the group number by a dot (Iannelli et al. Gene. 2002; 284(1-2):63-71) as follows: PspC1.1, PspC2.1, PspC2.2, PspC3.1, PspC3.4, PspC4.2/PspC10.1, PspC5.1, PspC6.1/PspC9.1, PspC7.1, PspC8.1, PspC11.1 and PspC11.4 (SEQ ID NOs: 30-41, respectively).

RrgB is the major subunit and stalk protein of the pneumococcal pilus. *S. pneumoniae* pilus 1 is encoded by a genetic islet (PI-1) present in about 30% of the pneumococcal strains and is implicated in adhesion to epithelial cells, lung infection, and virulence. Pilus 1 is composed of the backbone subunit RrgB, the minor pilin subunits RrgA, and RrgC (Barocchi, et al. Proc Natl Acad Sci USA. 2006; 103(8):2857-62). A reference sequence from strain TIGR4 is presented in SEQ ID NO: 42.

The term protective immunity in the present context refers to immunization measures resulting in any degree of reduction in the likelihood of developing the condition for which the protective immunity is relevant, including a minor, substantial or major reduction in likelihood of developing the condition as well as total prevention. Preferably, the degree of likelihood reduction is at least a minor reduction.

The term sequence identity expressed in percentage is defined as the value determined by comparing two optimally aligned sequences over a comparison window, wherein a portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Unless indicated otherwise, the comparison window is the entire length of the sequence being referred to. In this context, optimal alignment is the alignment produced by the BLASTP algorithm as implemented online by the US National Center for Biotechnology Information (see The NCBI Handbook, 2nd edition [https://www.ncbi.nlm.nih.gov/books/NBK143764/]), with the following input parameters: Word length=3, Matrix=BLOSUM62, Gap cost=11, Gap extension cost=1.

BRIEF DESCRIPTION OF THE FIGURES

FIG. 3. Intranasal immunization with MP confers protection against intranasal pneumococcal infection. (A, B) T4 membrane particles (MP) confer cross-protection against infection with a serotype 1 strain. (A) Intranasal immunization of C57BL/6 mice MP from strain T4 of serotype 4, and then infection with strain BHN733 of serotype 1, resulted in 80% survival. 20 mice per group. (B) Bacteria (in colony forming units, CFU) in the lungs of immunized and infected mice in (A) after sacrifice. Each dot represents one mouse. (C,D) Immunization with MP of serotype 3 confers antibody-dependent protection against intranasal infection with the same strain that is dependent on proteins, but not on capsule. (C) Percentage of mice that survived the intranasal infection with serotype 3 bacteria of wild type C57BL/6 mice or of B-cell deficient mice (muMt knockout mice) immunized with MPs from the same serotype 3 strain BHN428, or of wild type mice immunized with MPs from the serotype 4 strain T4. 20 mice per group. (D) Number of bacteria (CFU) in the lungs of mice from (C) at sacrifice. Each dot represents one mouse. (E,F) Protection conferred by MPs against intranasal pneumococcal challenge is not dependent on the cholesterol-binding cytotoxin pneumolysin. (E) Percentage survival after intranasal infection with T4 of wild type C57BL/6 mice immunized with MPs from T4 or its pneumolysin deficient strain T4Δply. 10 mice per group, 5 mice immunized with adjuvant as control. (F) Number of bacteria (CFU) in the lungs of mice at sacrifice. Each dot represents one mouse, *=$p<0.05$; =$p<0.01$; *=$p<0.001$; ****=$p<0.0001$.

FIG. 4. Intranasal immunization of mice with MP increases survival after intranasal pneumococcal challenge in a 7-day survival model. (A-D) Intranasal immunization of C57BL/6 mice with MPs from strain T4 increases survival after intranasal challenge with strain BHN733 of serotype 1 (corresponding to the experiments in FIG. 3). Bacterial counts (CFU) in the blood of mice immunized with (A) PBS, (B) Adjuvant only, (C) MPs from T4, or (D) MPs+Adjuvant, and then infected with strain BHN733 of serotype 1. Each dot represents one mouse. (E-H) Immunization of mice with MPs from serotype 3 protects against intranasal infection with the same strain. Bacterial counts (CFU) in the blood of mice immunized with (E) Adjuvant only, (F) MPs from serotype 3+Adjuvant or (G) MPs from serotype 4+Adjuvant, and then infected with strain BHN428 of serotype 3. (H) CFU in the blood of mice deficient in B cells immunized with MPs from the serotype 3 strain BHN428, and then infected with the same strain (FIG. 1C). In all graphs, each dot represents one mouse. (I-K) The cytotoxin pneumolysin does not affect the protective effect by MPs. CFU in the blood of mice immunized with (I) Adjuvant only, (J) MPs from T4+Adjuvant or (K) MPs from T4Δply+Adjuvant, and then infected with strain T4. Each dot represents one mouse.

(A-F) Intranasal immunization with MPs from different T4 mutants, subsequently followed by bacterial challenge with a serotype 1(BHN733) strain, in a 7-day survival experiment, as shown in FIG. 5A,B. CFU in the blood the blood of mice is shown for the groups immunized with (A) T4 MP+Adjuvant, (B) T4ΔpspAΔmalX MP+Adjuvant, (C) T4ΔpspAXΔprsA MP+adjuvant, (D) T4AmalXΔprsA MP+Adjuvant, (E) T4ΔpspAΔmalXΔprsA MP+Adjuvant and (F) Adjuvant only. Each dot represents one mouse. Each dot represents one mouse. Red-colored dots represent mice that were sacrificed at that time point.

Figure 14:
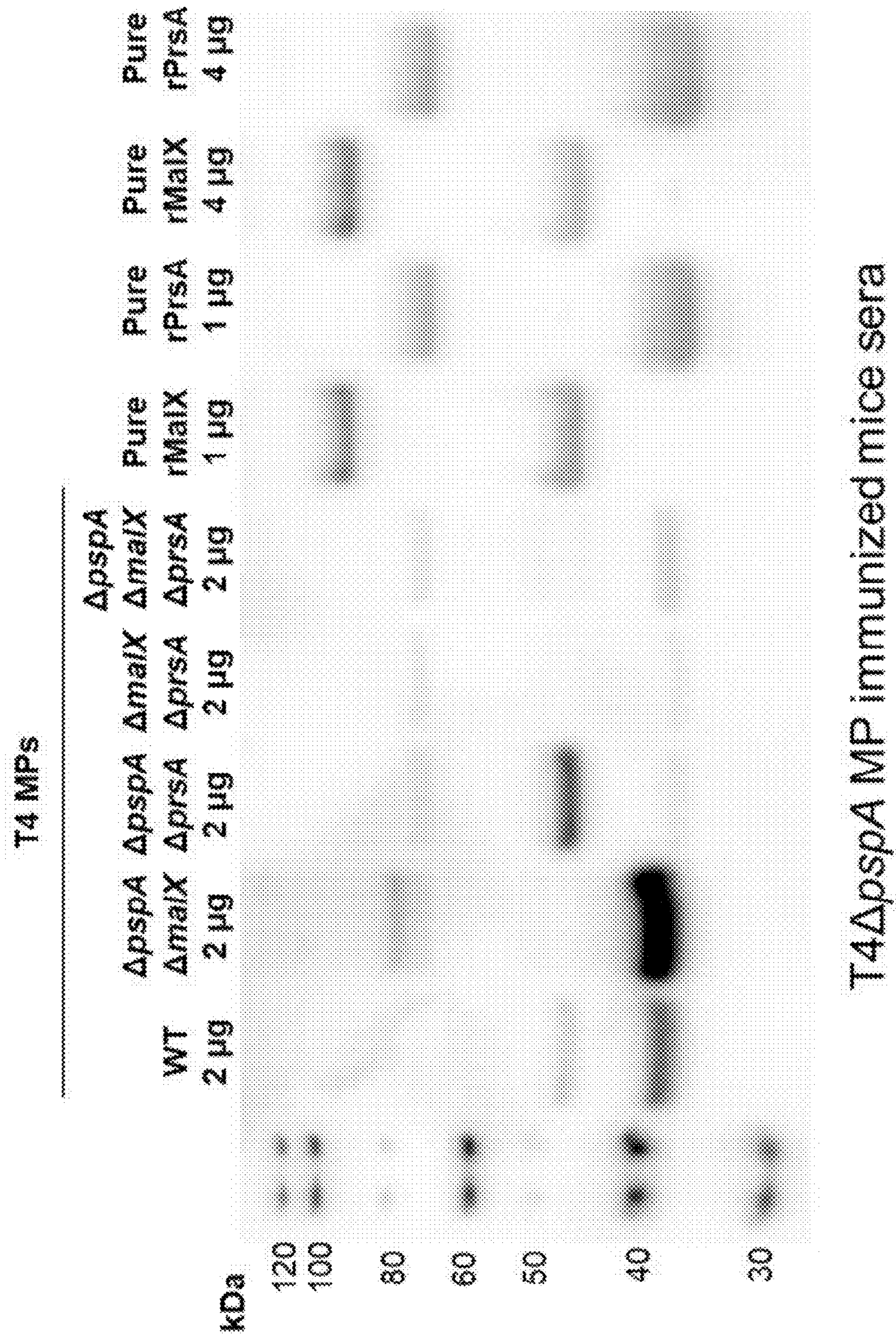

FIG. 14. Detection of MalX and PrsA in membrane particles as compared to purified recombinant proteins. Western blot using pooled sera of mice that were immunized with membrane particles from T4ΔpspA for antigen detection. MalX and PrsA were identified as main antigens. Secondary antibody anti-mouse IgG was used for detection.

Figure 15:
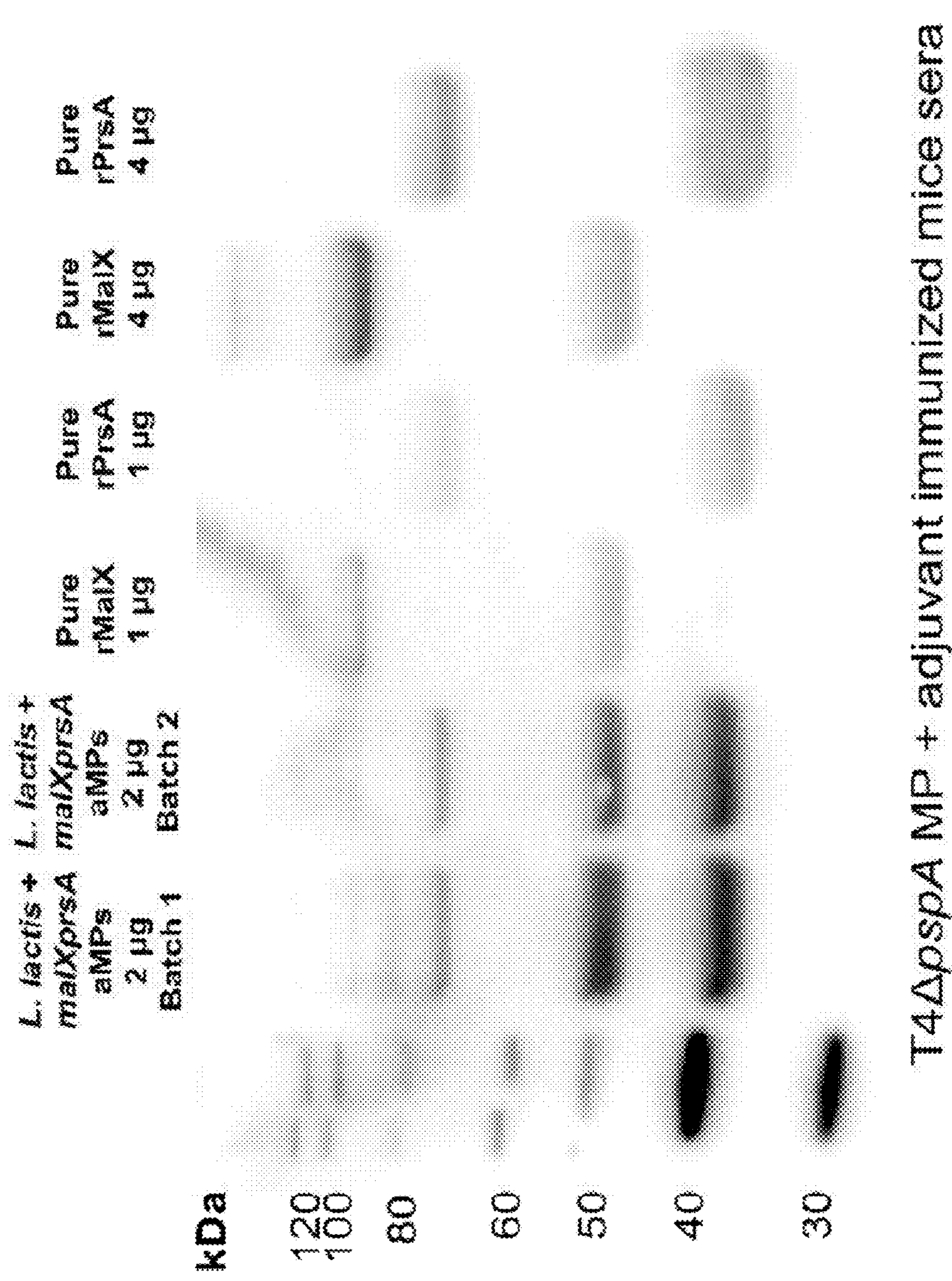

FIG. 15. Antisera from mice immunized with T4pspA MPs reacts strongly with artificial membrane particles (aMPs).

SUMMARY OF THE INVENTION

The present invention relates to the following items. The subject matter disclosed in the items below should be regarded disclosed in the same manner as if the subject matter were disclosed in patent claims.

1. An immunogenic composition comprising bacterial (preferably streptococcal) membrane vesicles (MVs), said MVs comprising a streptococcal MalX antigen and/or a streptococcal PrsA antigen, wherein the MVs preferably do not comprise an immunogenic amount of a streptococcal PspA antigen, wherein the MVs are preferably *Streptococcus pneumoniae* MVs.
2. An immunogenic composition comprising a streptococcal MalX antigen and/or a streptococcal PrsA antigen, characterized in that the composition does not comprise an immunogenic amount of a streptococcal PspA antigen, wherein when present, the sequence(s) of the MalX antigen and/or the PrsA antigen is/are preferably derived from *Streptococcus pneumoniae.*
3. An immunogenic composition comprising a streptococcal MalX antigen and/or a streptococcal PrsA antigen, characterized in that the MalX antigen and/or the PrsA antigen are not associated with a membrane vesicle derived from the same strain as the antigen(s), wherein when present, the sequence(s) of the MalX antigen and/or the PrsA antigen is/are preferably derived from *Streptococcus pneumoniae.*
4. The composition according to any of the preceding items, wherein composition comprises the MalX antigen.
5. The composition according to any of the preceding items, wherein composition comprises the PrsA antigen.
6. The composition according to any of the preceding items, wherein composition comprises both the MalX antigen and the PrsA antigen.
7. The composition according to any of the preceding items, wherein the MalX antigen is present at a concentration of at least 0.001 μg/ml, preferably at least 0.05 μg/ml, more preferably at least 0.1 μg/ml, most preferably at least 1 μg/ml.
8. The composition according to any of the preceding items, wherein the PrsA antigen is present at a concentration of at least 0.001 μg/ml, preferably at least 0.05 μg/ml, more preferably at least 0.1 μg/ml, most preferably at least 1 μg/ml.
9. The composition according to any of the preceding items, wherein both the PrsA antigen and the MalX antigen are present at relative amounts of 10:1 to 1:10 by weight, preferably 5:1 to 1:5, more preferably 2:1 to 1:2, most preferably about 1:1.
10. The composition according to any of the preceding items, wherein the PspA antigen is absent or present at a concentration of less than 0.01 μg/ml, preferably less than 0.005 μg/ml, more preferably less than 0.001 μg/ml, most preferably absent.
11. The composition according to any of the preceding items, wherein the MalX antigen comprises a sequence having at least 70%, preferably 80%, more preferably 85%, yet more preferably 90%, still more preferably 95%, most preferably 100% sequence identity to any one of SEQ ID NOs: 25 or 43-47 over a stretch of at least 50 amino-acids, preferably at least 100 amino acids, more preferably at least 200 amino acids, most preferably over the entire sequence presented in said SEQ ID NO.
12. The composition according to any of the preceding items, wherein the MalX antigen comprises a sequence having at least 70%, preferably 80%, more preferably 85%, yet more preferably 90%, still more preferably 95%, most preferably 100% sequence identity to SEQ ID NO: 25.
13. The composition according to any of the preceding items, wherein the PrsA antigen comprises a sequence having at least 70%, preferably 80%, more preferably 85%, yet more preferably 90%, still more preferably 95%, most preferably 100% sequence identity to any one of SEQ ID NOs: 26 or 48-53 over a stretch of at least 50 amino-acids, preferably at least 100 amino acids, more preferably at least 200 amino acids, most preferably over the entire sequence presented in said SEQ ID NO.
14. The composition according to any of the preceding items, wherein the PrsA antigen comprises a sequence having at least 70%, preferably 80%, more preferably 85%, yet more preferably 90%, still more preferably 95%, most preferably 100% sequence identity to SEQ ID NO: 26.
15. The composition according to any of the preceding items, wherein the PspA antigen comprises a sequence having at least 70%, preferably 80%, more preferably 85%, yet more preferably 90%, still more preferably 95%, most preferably 100% sequence identity to SEQ ID NO: 27.
16. The composition according to item 1 or item dependent thereon, wherein the membrane vesicles are of the type *Streptococcus pneumoniae* membrane vesicle microparticles.
17. The composition according to any of items 2-3, or any items dependent thereon, wherein the antigens are associated with MVs, which may be native or artificial MVs.
18. The composition according to item 1 or any item dependent thereon or item, 17, wherein the MVs comprise MalX at the level of ≥0.001 μg/μg, preferably ≥0.01 μg/μg, more preferably ≥0.02 μg/μg, yet more preferably ≥0.05 μg/μg, most preferably ≥0.1 μg/μg of the total protein in the MVs.
19. The composition according to item 1 or any item dependent thereon or item 17 or any item dependent thereon, wherein the MVs comprise PrsA at the level of ≥0.001 μg/μg, preferably ≥0.01 μg/μg, more preferably ≥0.02 μg/μg, yet more preferably ≥0.05 μg/μg, most preferably ≥0.1 μg/μg of the total protein in the MVs.

20. The composition according to item 1 or any item dependent thereon or item 17 or any item dependent thereon, wherein the MVs lack PspA, or PspA is present at a level which is less than 0.01 μg/μg, preferably less than 0.05 μg/μg, yet more preferably less than 0.001 μg/μg of the total protein in the MVs, most preferably the MVs lack PspA.

21. The composition according to item 1 or any item dependent thereon or item 17 or any item dependent thereon, wherein MVs are 5-1000 nm in diameter, preferably 5-300 nm, more preferably 15-175 nm, most preferably 10-125 nm.

22. The composition according to item 1 or any item dependent thereon or item 17 or any item dependent thereon, comprising MVs in an amount of 1 μg/ml, preferably 5 μg/ml, more preferably 10 μg/ml, most preferably 100 μg/ml.

23. The composition according to item 1 or any item dependent thereon or item 17 or any item dependent thereon, wherein the MVs are derived from any *Streptococcus pneumoniae* strain, preferably any strain/s of serotype 1, 3, 4, 5, 6A, 6B, 6C, 6D, 7F, 8, 9N, 9V, 10A, 11A, 11B, 12F, 13, 14, 15A, 15B, 15C, 16F, 17F, 18C, 19A, 19F, 20, 21, 22F, 23A, 23B, 23F, 24F, 31, 33F, 34, 35B, 35F, 37, 38, including strains TIGR4, P1031, BHN418, and A66.

24. The composition according to any of the preceding items, wherein the composition comprises the MalX antigen and/or the PrsA antigen associated with membrane vesicles from a host cell being a firmicute.

25. The composition according to any of the preceding items, wherein the antigen(s) is/are associated with membrane vesicles from a host cell, where the antigen(s) is/are heterologous in relation to the host cell.

26. The composition according to item 25, wherein the host cell is of the genus *Lactobacillus* or *Lactococcus*.

27. The composition according to item 26, wherein the host cell is a *Lactococcus lactis*-cell.

28. The composition according to item 1 or any item dependent thereon or item 17 or any item dependent thereon, wherein the membrane vesicles are artificial membrane particles.

29. The composition according to item 1 or any item dependent thereon or item 17 or any item dependent thereon, wherein the membrane vesicles comprise disrupted bacterial cells, preferably mechanically disrupted cells.

30. The composition according to item 1 or any item dependent thereon or item 17 or any item dependent thereon, wherein the membrane vesicles comprise membrane vesicles derived from mechanically disrupted bacterial cells.

31. The composition according to item 2 or any item dependent thereon, wherein the composition comprises the MalX antigen and/or the PrsA antigen not associated with streptococcal (preferably *Streptococcus pneumoniae*) membrane vesicles.

32. The composition according to any of the preceding items, wherein the composition comprises the MalX antigen and/or the PrsA antigen as isolated proteins, preferably recombinant proteins, or as peptides such as synthetic peptides or truncated recombinant proteins.

33. The composition according to any of the preceding items, wherein the composition further comprises a nanoparticle carrier.

34. The composition according to item 33, wherein the nanoparticle carrier comprises an ISCOM, an ISCOM matrix, a liposome, a polymeric nanoparticle, an inorganic nanoparticle, a non-biodegradable nanoparticle, a calcium phosphate particle, an emulsion or a virus-like particle.

35. The composition according to any of the preceding items, wherein the composition is devoid of whole *Streptococcus* cells, preferably *Streptococcus pneumoniae* cells.

36. The composition according to any of the preceding items, further comprising capsular polysaccharides from a *Streptococcus* sp., preferably *Streptococcus pneumoniae*.

37. The composition according to any of the preceding items, for use as a medicament.

38. The composition according to any of the preceding items, wherein the composition is a vaccine.

39. The composition according to any of the preceding items, wherein the composition further comprises an adjuvant, preferably aluminium hydroxide, a lipid-based substance such as squalene, an immune-stimulating component or a protein from a microbe such as diphtheria (preferably CRM), cholera (preferably choleratoxoid CTB or mmCT) or *Escherichia coli* (preferably non-toxic heat-labile toxin such as LTK63 or dmLT).

40. The composition according to any of the preceding items, wherein the composition is capable of eliciting serotype independent antibodies against a *Streptococcus* sp., preferably *Streptococcus pneumoniae*, when administered to a mammalian host.

41. The composition according to any of the preceding items, wherein the composition is capable of eliciting opsonophagocitic antibodies against a *Streptococcus* sp., preferably *Streptococcus pneumoniae*, when administered to a mammalian host.

42. The composition according to any of the preceding items, wherein the composition is capable of eliciting serotype-independent antibodies against a *Streptococcus* sp., preferably *Streptococcus pneumoniae*, when administered to a mammalian host.

43. The composition according to any of the preceding items, for use in a method for inducing protective immunity against a *Streptococcus* sp. in a subject.

44. The composition according to any of the preceding items, for use in a method for inducing protective immunity against *Streptococcus pneumoniae* in a subject.

45. The composition according to any of the preceding items, for use in a method for inducing protective immunity against a *Streptococcus* sp. in a subject, wherein the immunity is protective against a condition selected from pneumococcal sinusitis, pneumococcal otitis, pneumococcal pneumonia and invasive pneumococcal disease including but not limited to pneumococcal sepsis and pneumococcal meningitis, preferably invasive pneumococcal disease.

46. The composition according to any of the preceding items, for use according to any of items 43-45, wherein the protective immunity is serotype-independent.

47. A method for manufacturing a composition according to item 28 or any item dependent thereon, comprising:

a. expressing a streptococcal MalX antigen and/or a streptococcal PrsA antigen in a suitable host cell, preferably heterologously;
b. generating membrane vesicles by disrupting the host cell expressing said antigens; and
c. recovering the generated membrane vesicles to form an immunogenic composition comprising a streptococcal MalX antigen and/or a streptococcal PrsA antigen associated with membrane vesicles.

48. The method according to item 47, wherein the host cells are mechanically disrupted, preferably by shear forces, most preferably with a French press.
49. The method according to any of items 47-48, wherein the recovering step comprises precipitation by centrifugation followed by resuspension.

DETAILED DESCRIPTION

The present invention is based on the inventor's studies on membrane vesicles secreted by *Streptococcus pneumoniae*. These vesicles are known to differ in properties between cells grown in liquid culture and on solid media. Intranasal immunization with the membrane vesicles confers serotype-independent cross-protection against invasive pneumococcal disease (Example 1), reduces pneumococcal load in the airways (Example 1) and leads to production of pneumococcal-specific antibodies with opsonophagocytic activity (Example 2). The membrane vesicles can confer antibody-dependent, and mainly serotype-independent, protection against challenge with serotype 3 pneumococci (Examples 3 and 4).

The inventors conducted further studies to elucidate the specific antigens responsible for the immunogenic effects of the membrane vesicles. The cytotoxin pneumolysin Ply (while a known vaccine candidate) was found not to be required (Example 5).

In addition, a major membrane vesicle protein PspA, while a dominant immunogen in the MPs and a known vaccine antigen candidate, was unexpectedly found to be not required for the cross-protection. In fact, the inventors surprisingly discovered that better protection could in fact be achieved with membrane vesicle preparation devoid of PspA (Example 6). The inventors further unexpectedly discovered that cross-protection mediated by membrane vesicles against invasive pneumococcal disease is dependent on the lipoproteins PrsA and MalX (Example 7). Thus, the inventors have discovered the use a cocktail of MP from different serotypes lacking PspA, but presenting MalX and PrsA, as a novel vaccine approach that can target most non-vaccine pneumococci, especially in the elderly.

It was also demonstrated that antibodies raised against MPs containing MalX and/or PrsA recognized their native antigens much more efficiently than plain protein recombinant versions, indicating that the antibody binding is to a significant degree dependent on features missing from the plain recombinant proteins (Example 9). Such features include the presence of the signal peptide and the lipid modification of the terminal cysteine residue, e.g. N-palmitoyl cysteine or S-diacylglycerol cysteine. Therefore, the antigens as presented in their native context incorporated in MPs are superior as vaccine antigens compared to plain recombinant proteins.

Finally, the inventors demonstrated that MalX and/or PrsA-containing membrane vesicles may be generated artificially through mechanical cell disruption, for large-scale production (Examples 10 and 11).

The above studies resulted in the invention of novel immunogenic compositions and methods disclosed below.

Immunogenic Compositions

In a first aspect, the present invention provides an immunogenic composition comprising bacterial membrane vesicles (preferably streptococcal, most preferably *Streptococcus pneumoniae* membrane vesicles) (MVs), preferably said MVs comprising a streptococcal MalX antigen and/or a streptococcal PrsA antigen. Preferably, the MVs do not comprise an immunogenic amount of a streptococcal PspA antigen. In a preferred combination, both MalX and PrsA are present, but PspA absent. It should be understood that the MVs of the first aspect may be of the type produced by bacteria through biological processes, or be artificial MVs produced through disruption of bacteria as described herein.

In a second aspect, the present invention provides an immunogenic composition comprising a streptococcal MalX antigen and/or a streptococcal PrsA antigen, characterized in that the composition does not comprise an immunogenic amount of a streptococcal PspA antigen. In a preferred variation of the second aspect, there is provided an immunogenic composition comprising a streptococcal MalX antigen and a streptococcal PrsA antigen associated with membrane vesicles from a host cell, characterized in that the MalX antigen and the PrsA antigen are not associated with a membrane vesicle derived from the same strain as the antigens, and wherein the sequence(s) of the MalX antigen and the PrsA antigen are derived from *Streptococcus pneumoniae*. It should be understood that the antigens in the composition of the second aspect may be associated with MVs produced by bacteria through biological processes, or with artificial MVs produced through disruption of bacteria as described herein.

In a third aspect, the present invention provides an immunogenic composition comprising a streptococcal MalX antigen and/or a streptococcal PrsA antigen, characterized in that the MalX antigen and/or the PrsA antigen are not associated with a membrane vesicle derived from the same strain as the antigen(s).

The antigens may be associated with membrane vesicles from host organisms to which they have been introduced by genetic engineering. In this case, the antigen(s) would be associated with a membrane vesicle but in a non-native context. Preferably, the antigens are heterologous in relation to the membrane vesicles. It is also contemplated that the MalX antigen and/or the PrsA antigen may not be associated with any membrane vesicle. The antigens in the composition of the third aspect may be associated with MVs either produced by bacteria through biological processes, or with artificial MVs produced through disruption of bacteria as described herein.

Antigens

Preferably, the composition of the first, second or third aspect comprises the MalX antigen. Also preferably, the composition comprises the PrsA antigen. More preferably, the composition comprises both the MalX antigen and the PrsA antigen. When both the PrsA antigen and the MalX antigen are present, they may be present at relative amounts of 10:1 to 1:10 by weight, preferably 5:1 to 1:5, more preferably 2:1 to 1:2, most preferably about 1:1. Alternatively, the PrsA antigen and the MalX antigen may be present at relative amounts of 10:1 to 1:10 on a molar basis, preferably 5:1 to 1:5, more preferably 2:1 to 1:2, most preferably about 1:1.

On weight basis, the MalX antigen may be present at a concentration of at least 0.001 μg/ml, preferably at least 0.05 μg/ml, more preferably at least 0.1 μg/ml, most preferably at least 1 μg/ml. The PrsA antigen may present at a concentration of at least 0.001 μg/ml, preferably at least 0.05 μg/ml, more preferably at least 0.1 μg/ml, most preferably at least 1 μg/ml. The PspA antigen may be absent or present at a concentration of less than 0.01 μg/ml, preferably less than 0.005 μg/ml, more preferably less than 0.001 μg/ml, most preferably absent.

On molar basis, the MalX antigen may be present at a concentration of at least 0.025 nM, preferably at least 1.25 nM, more preferably at least 2.5 nM, most preferably at least 25 nM. The PrsA antigen may present at a concentration of at least 0.025 nM, preferably at least 1.25 nM, more preferably at least 2.5 nM, most preferably at least 25 nM. The PspA antigen may be absent or present at a concentration of less than 0.25 nM, preferably at less than 0.05 nM, more preferably less than 0.01 nM, most preferably absent.

The MalX and/or PrsA antigens may be proteins, peptides or peptidomimetics sharing a sequence similarity with the naturally occurring antigens. The antigens may be a fragment or a modified version of the naturally occurring antigen, or a complete antigen.

The sequence of the MalX antigen is preferably derived from *Streptococcus pneumoniae*. The MalX antigen may comprise a sequence having at least 70%, preferably 80%, more preferably 85%, yet more preferably 90%, still more preferably 95%, most preferably 100% sequence identity to any one of SEQ ID NOs: 25 or 43-47. The MalX antigen may comprise a sequence having at least 70%, preferably 80%, more preferably 85%, yet more preferably 90%, still more preferably 95%, most preferably 100% sequence identity to SEQ ID NO: 25.

The sequence of the PrsA antigen is preferably derived from *Streptococcus pneumoniae*. The PrsA antigen may comprise a sequence having at least 70%, preferably 80%, more preferably 85%, yet more preferably 90%, still more preferably 95%, most preferably 100% sequence identity to any one of SEQ ID NOs: 26 or 48-53.

The PrsA antigen may comprises a sequence having at least 70%, preferably 80%, more preferably 85%, yet more preferably 90%, still more preferably 95%, most preferably 100% sequence identity to SEQ ID NO: 26.

The sequence of the PspA antigen is preferably derived from *Streptococcus pneumoniae*. The PspA antigen may comprises a sequence having at least 70%, preferably 80%, more preferably 85%, yet more preferably 90%, still more preferably 95%, most preferably 100% sequence identity to SEQ ID NO: 27.

The sequence identity referred to above may be determined over a stretch of at least 50 amino acids, preferably at least 100 amino acids, more preferably at least 200 amino acids, most preferably over the entire sequence presented in the SEQ ID NO serving as the reference.

Membrane Vesicle Composition

Preferably, the composition of the first aspect comprises the MalX antigen and/or the PrsA antigen, most preferably both. The antigens are regarded present when they are present in at least immunogenic amounts, i.e., such amount that the composition is capable of inducing an immune response against the antigen after the composition has been administered to a vertebrate host, such as a human or a mouse.

The membrane vesicles (MVs) of the composition of the first aspect may be of the type *Streptococcus pneumoniae* membrane vesicle microparticles. Such *Streptococcus pneumoniae* membrane vesicle microparticle may be characterized by that they comprise:

i. the protein Ply at the level of ≥0.070 μg/μg total protein in the MP;
ii. the protein LytA at the level of ≥0.070 μg/μg total protein in the MP;
iii. the protein PspC at the level of ≥0.130 μg/μg total protein in the MP; and/or
iv. the protein RrgB at the level of ≥0.020 μg/μg total protein in the MP.

The microparticle may comprise the protein Ply at the level of ≥0.070 μg/μg total protein in the MP. The microparticle may comprise the protein Ply at the level of ≥0.15, preferably ≥0.2, more preferably ≥0.3, most preferably ≥0.35 μg/μg total protein in the MP.

The microparticle may comprise the protein LytA at the level of ≥0.070 μg/μg total protein in the MP. The microparticle may comprise the protein LytA at the level of ≥0.08, preferably ≥0.09, yet more preferably ≥0.1 μg/μg, most preferably ≥0.2 μg/μg total protein in the MP.

The microparticle, MP, may comprise the protein PspC at the level of ≥0.130 μg/μg total protein in the MP. The microparticle may comprise comprising the protein PspC at the level of ≥0.15, preferably ≥0.18, more preferably ≥0.2, most preferably ≥0.3 μg/μg total protein in the MP.

The microparticle may comprise the protein RrgB at the level of ≥0.02 μg/μg total protein in the MP. The microparticle may comprise the protein RgrB at the level of ≥0.022, preferably ≥0.025, most preferably ≥0.028 μg/μg total protein in the MP.

The protein Ply may comprise a sequence having at least 70%, preferably 80%, more preferably 85%, yet more preferably 90%, still more preferably 95%, most preferably 100% sequence identity to SEQ ID NO: 28.

The protein LytA may comprise a sequence having at least 70%, preferably 80%, more preferably 85%, yet more preferably 90%, still more preferably 95%, most preferably 100% sequence identity to SEQ ID NO: 29.

The protein PspC may comprise a sequence having at least 40% or 70%, preferably 80%, more preferably 85%, yet more preferably 90%, still more preferably 95%, most preferably 100% sequence identity to SEQ ID NOs: 30.

The protein PspC may comprise a sequence having at least 70%, preferably 80%, more preferably 85%, yet more preferably 90%, still more preferably 95%, most preferably 100% sequence identity to any one of SEQ ID NOs: 30-41.

The protein RgrB may comprise a sequence having at least 70%, preferably 80%, more preferably 85%, yet more preferably 90%, still more preferably 95%, most preferably 100% sequence identity to SEQ ID NO: 42.

The membrane vesicle microparticles may be as described in WO 2018/123959.

Preferably, the antigens in the compositions of the first, second and/or third aspects are associated with MVs.

The MVs may comprise MalX at the level of ≥0.001 μg/μg, preferably ≥0.01 μg/μg, more preferably ≥0.02 μg/μg, yet more preferably ≥0.05 μg/μg, most preferably ≥0.1 μg/μg total protein in the MVs.

The MVs may comprise PrsA at the level of ≥0.001 μg/μg, preferably ≥0.01 μg/μg, more preferably ≥0.02 μg/μg, yet more preferably ≥0.05 μg/μg, most preferably ≥0.1 μg/μg total protein in the MVs.

The MVs may lack PspA, or PspA may be present at a level which is less than 0.01 μg/μg, preferably less than 0.05 ag/μg, yet more preferably less than 0.001 μg/μg total protein in the MV. Most preferably, the MVs lack PspA.

The MVs may be 5-1000 nm in diameter, preferably 5-300 nm, more preferably 15-175 nm, most preferably 10-125 nm.

The composition of the first, second or third aspects may comprise MVs in an amount of 1 μg/ml, preferably 5 μg/ml, more preferably 10 μg/ml, most preferably 100 μg/ml.

The MVs may be derived from any *Streptococcus pneumoniae* strains, preferably any strain/s of serotype 1, 3, 4, 5, 6A, 6B, 6C, 6D, 7F, 8, 9N, 9V, 10A, 11A, 11B, 12F, 13, 14, 15A, 15B, 15C, 16F, 17F, 18C, 19A, 19F, 20, 21, 22F, 23A, 23B, 23F, 24F, 31, 33F, 34, 35B, 35F, 37, 38, including strains TIGR4, P1031, BHN418 and A66.

Composition of Membrane Vesicles from Other Bacteria than Streptococci

The composition of the first, second or third aspects may comprise the MalX antigen and/or the PrsA antigen not associated with streptococcal membrane vesicles (in particular *Streptococcus pneumoniae* membrane vesicles). Instead, the antigens may be associated with other bacterial membrane vesicles from gram-positive and/or gram-negative bacteria such as firmicutes including Lactobacillales order, Bacillales order, proteobacteria such as *E. coli* and a *Klebsiella* species, a *Neisseria* species, and a *Haemophilus* species, or associated with artificially made lipid droplets (e.g. liposomes).

*Streptococcus pneumoniae* growing on solid medium produce highly immunogenic MP, but the yield is low. After identifying pneumococcal MalX and PrsA as the two major protective MP antigens the inventors heterologously overexpressed these two proteins in *Lactococcus lactis*. This non-pathogenic Gram-positive organism is widely used in dairy industry and a natural member of the vaginal microbiota, making is suitable as a platform for large scale production of native membrane bound antigens for vaccine purposes.

Thus, in some cases, the membrane vesicles and the antigen(s) may be derived from different species. The antigen(s) may be recombinantly expressed in the host producing the membrane vesicle, the antigen(s) preferably being heterologous to the host.

The host cell is preferably of the genus *Lactococcus*. More preferably, the host cell is a *Lactococcus lactis*-cell.

The membrane vesicles are preferably artificial membrane particles (aMP) i.e., particles that are generated by treatment of the host cells, e.g., by mechanical disruption. The aMPs are preferably enriched, isolated or purified from other cell debris (i.e. cell components not part of the aMPs) derived from the disrupted host cells, e.g., by filtration, selective precipitation, gradient centrifugation, ultracentrifugation, combination thereof or similar techniques. By isolated in this context is meant that the relative amount of cell debris to aMPs is reduced by at least 50% in the final composition compared to the composition immediately after the aMPs were generated by treatment of the host cells. Preferably, the amount of cell debris is reduced by at least 70%, more preferably by at least 80%, even more preferably by at least 90%, still more preferably by at least 95%, most preferably by at least 99%.

The artificial membrane particles are to be understood to be distinct from membrane vesicles or membrane particles produced by cells through biological processes. Thus, the membrane vesicles preferably comprise disrupted bacterial cells, more preferably mechanically disrupted. Preferably, the membrane vesicles comprise membrane vesicles derived from mechanically disrupted bacterial cells. The membrane vesicles of the artificial type may be derived from *S. pneumoniae* or another suitable host such as *Lactococcus lactis* heterologously expressing the necessary pneumococcal antigens.

Non-Membrane Vesicle Compositions

The composition of the second or third aspects may comprise the MalX antigen and/or the PrsA antigen not associated with streptococcal (in particular *Streptococcus pneumoniae*) membrane vesicles.

The composition of the second or third aspects may comprise the MalX antigen and/or the PrsA antigen as isolated proteins, preferably recombinant proteins, or as peptides such synthetic peptides or truncated recombinant proteins, or as peptidomimetics.

Preferably, the MalX and/or the PrsA antigen of the second or third aspects are recombinant proteins with a post-translational modification of the terminal cysteine being bound to a lipid. More preferably, the terminal cysteine residue is N-palmitoyl cysteine or S-diacylglycerol cysteine. Preferably, the MalX and/or the PrsA antigen are recombinant proteins comprising the native signal peptide sequence.

Preferred Features of the Compositions

The compositions according to the first, second or third aspects may further comprise a nanoparticle carrier. Such nanoparticle carrier may comprise an ISCOM, an ISCOM matrix, a liposome, a polymeric nanoparticle, an inorganic nanoparticle, a non-degradable nanoparticle, an emulsion or a virus-like particle.

The compositions according to the first, second or third aspects may be devoid of whole streptococcal (in particular *Streptococcus pneumoniae*) cells.

The compositions according to the first, second or third aspects may further comprise capsular polysaccharides from a *Streptococcus* sp., preferably *Streptococcus pneumoniae*.

The compositions according to the first, second or third aspects may be formulated as a vaccine, preferably for intranasal, intramuscular or subcutaneous administration.

The compositions according to the first, second or third aspects may further comprise an adjuvant, preferably aluminium hydroxide, a lipid-based substance such as squalene, an immune-stimulating component or a proteins from a microbe such as diphtheria (preferably CRM), cholera (preferably choleratoxoid CTB or mmCT) or *Escherichia coli* (preferably non-toxic heat-labile toxin such as LTK63 or dmLT).

The compositions according to the first, second or third aspects may be capable of eliciting serotype independent antibodies against a *Streptococcus* sp, preferably *Streptococcus pneumoniae*, when administered to a mammalian host.

The compositions according to the first, second or third aspects may be capable of eliciting opsonophagocitic antibodies against a *Streptococcus* sp, preferably *Streptococcus pneumoniae*, when administered to a mammalian host.

The compositions according to the first, second or third aspects may be capable of eliciting antibodies against *Streptococcus pneumoniae* serotype 3, when administered to a mammalian host.

Prevention of Pneumococcal Disease

In a fourth aspect of the present invention, the compositions according to the first, second or third aspects may be for use as a medicament, preferably in a method for inducing protective immunity against a *Streptococcus* sp, preferably *Streptococcus pneumoniae*, in a subject.

The fourth aspect also encompasses a method for inducing protective immunity against a *Streptococcus* sp, preferably *Streptococcus pneumoniae*, in a subject in need thereof, comprising administering an effective amount of the composition according to the first, second or third aspects to the subject. The fourth aspect also encompasses the use of a composition according to the first, second or third aspects in the manufacture of a vaccine for immunization against a *Streptococcus* sp, preferably *Streptococcus pneumoniae.*

The protective immunity may be an immunity reducing the likelihood of a condition selected from pneumococcal sinusitis, pneumococcal otitis, pneumococcal pneumonia and invasive pneumococcal disease including but not limited to pneumococcal sepsis and pneumococcal meningitis, preferably invasive pneumococcal disease. Preferably, the subject to be immunized is a young child (e.g. less than 7 years of age) or an elderly person (e.g. over 65 years of age), but also other age groups could be targeted. Preferably, the protective immunity is at least partially serotype-independent, more preferably substantially serotype-independent, yet more preferably essentially serotype-independent, most preferably fully serotype-independent.

Preferably, the protective immunity encompasses protective immunity against serotype 3 pneumococci in addition to protective immunity against at least one other serotype, preferably serotype 1 and/or serotype 4.

For immunization, the composition may be administered to the subject in various manners known in the art, including but not limited to by way of injection (e.g. intramuscular, intracutaneous, subcutaneous, intravenous), buccal, oral and intranasal administration as well as inhalation.

Manufacturing a Composition with Artificial Membrane Particles

*Streptococcus pneumoniae* growing on solid medium produce highly immunogenic MP, but the yield is lower than desirable for many practical purposes such as large-scale vaccine production. Thus, it may be desirable to manufacture MVs as artificial membrane particles.

In a fifth aspect, the present invention provides method for manufacturing a composition according to first, second or third aspects, comprising:

a. expressing a streptococcal MalX antigen and/or a streptococcal PrsA antigen in a suitable host cell, preferably heterologously;
b. generating membrane vesicles by disrupting the host cell expressing said antigens; and
c. recovering the generated membrane vesicles to form an immunogenic composition comprising a streptococcal MalX antigen and/or a streptococcal PrsA antigen associated with membrane vesicles.

The host cells are preferably mechanically disrupted to generate the membrane vesicles, more preferably by shear forces, most preferably with a French press or a similar type of mechanical homogenization device.

The method may comprise isolating/purifying the artificial membrane particles by removing some or all of the cell debris derived from the disrupted host cells e.g., by filtration, gradient centrifugation, selective precipitation, ultracentrifugation, combination thereof or similar techniques.

By isolated in this context is meant that the relative amount of cell debris to aMPs is reduced by at least 50% in the final composition compared to the composition immediately after the aMPs were generated by treatment of the host cells. Preferably, the amount of cell debris is reduced by at least 70%, more preferably by at least 80%, even more preferably by at least 90%, still more preferably by at least 95%, most preferably by at least 99%.

The recovering step may comprise precipitation by ultracentrifugation followed by resuspension.

The host cells may be a *S. pneumoniae* strain expressing the appropriate antigens. The host cells may also be another suitable host such as a *Lactococcus* such as *Lactococcus lactis* heterologously expressing the necessary pneumococcal antigens by way of genetic engineering.

Discussion Relating to Present Disclosure

Figure 1:
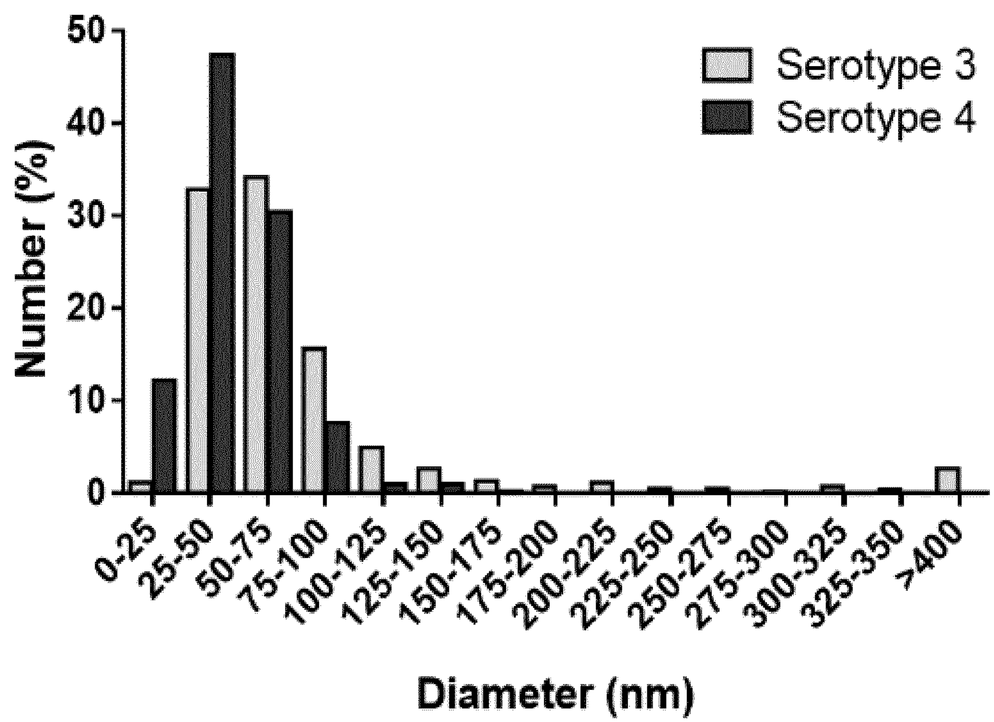
FIG. 1. Membrane particles (MP) produced by serotype 3 pneumococci are larger and contain more cytosolic proteins than MPs from serotype 4. (A) Size distribution of MPs from the serotype 3 strain BHN428 (n=523) and the serotype 4 strain T4 (n=378), as measured from electron micrographs. (B) Mass spectrometry identification of proteins present in MP isolated from the serotype 3 and 4 strains respectively. The number indicates proteins found based on their predicted subcellular localization, defined as cytosolic, transmembrane, membrane-associated (lipoproteins), cell wall associated and secreted.
Figure 6A:
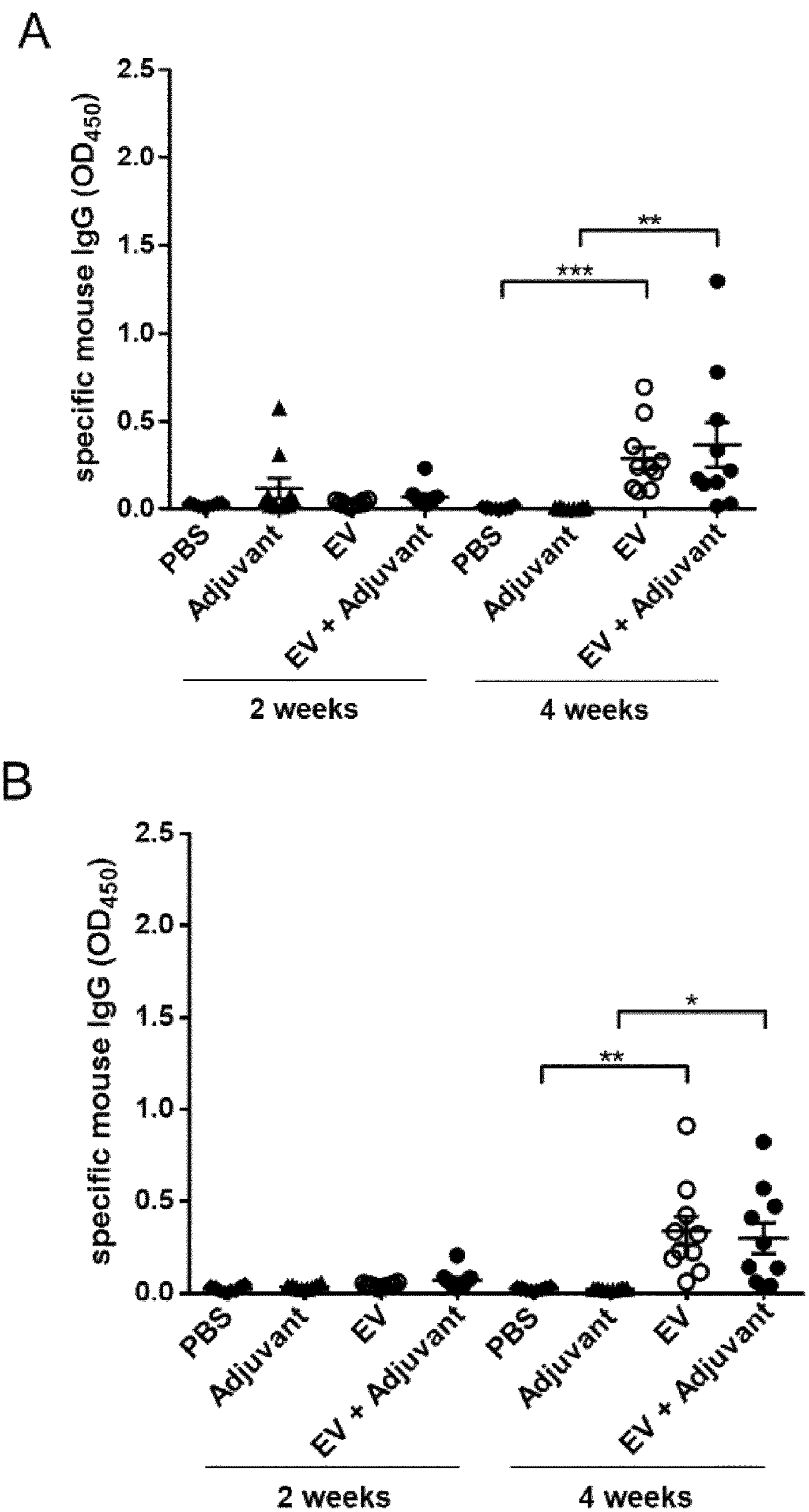
FIG. 6. Immunization with EVs, as compared to MPs (see above FIG. 3-5), from T4 confers lower cross-protection against intranasal infection with serotype 1. Intranasal immunization of C57BL/6 mice with extracellular vesicles (EVs) from strain T4 of serotype 4 led to a lower survival and lower production of pneumococcal specific IgG as compared to immunization with MPs. (A-B) Using ELISA analysis, specific IgG was detected two weeks after the first immunization with EV (prior to the second immunization) and four weeks after the first immunization (2 weeks after the booster, prior to infection), in wells coated with (A) wild type T4, and (B) T4R (isogenic mutant in the capsule of T4) bacteria. Each dot represents one mouse serum. (C) Intranasal immunization of C57BL/6 mice with EVs from strain T4 of serotype 4 and infection with the strain BHN733 of serotype 1 led to lower survival (40%) compared to mice immunized with MPs from the same strain (see FIG. 1). 20 mice per group. *=p<0.05, **=p<0.01. (D) Bacterial counts (CFU) detected in the lungs of immunized and infected mice from (C) after sacrifice. (E-F) CFU detected in the blood of mice immunized with (E) EVs only or (F) EVs+Adjuvant. Each dot represents one mouse.
Figure 6E:
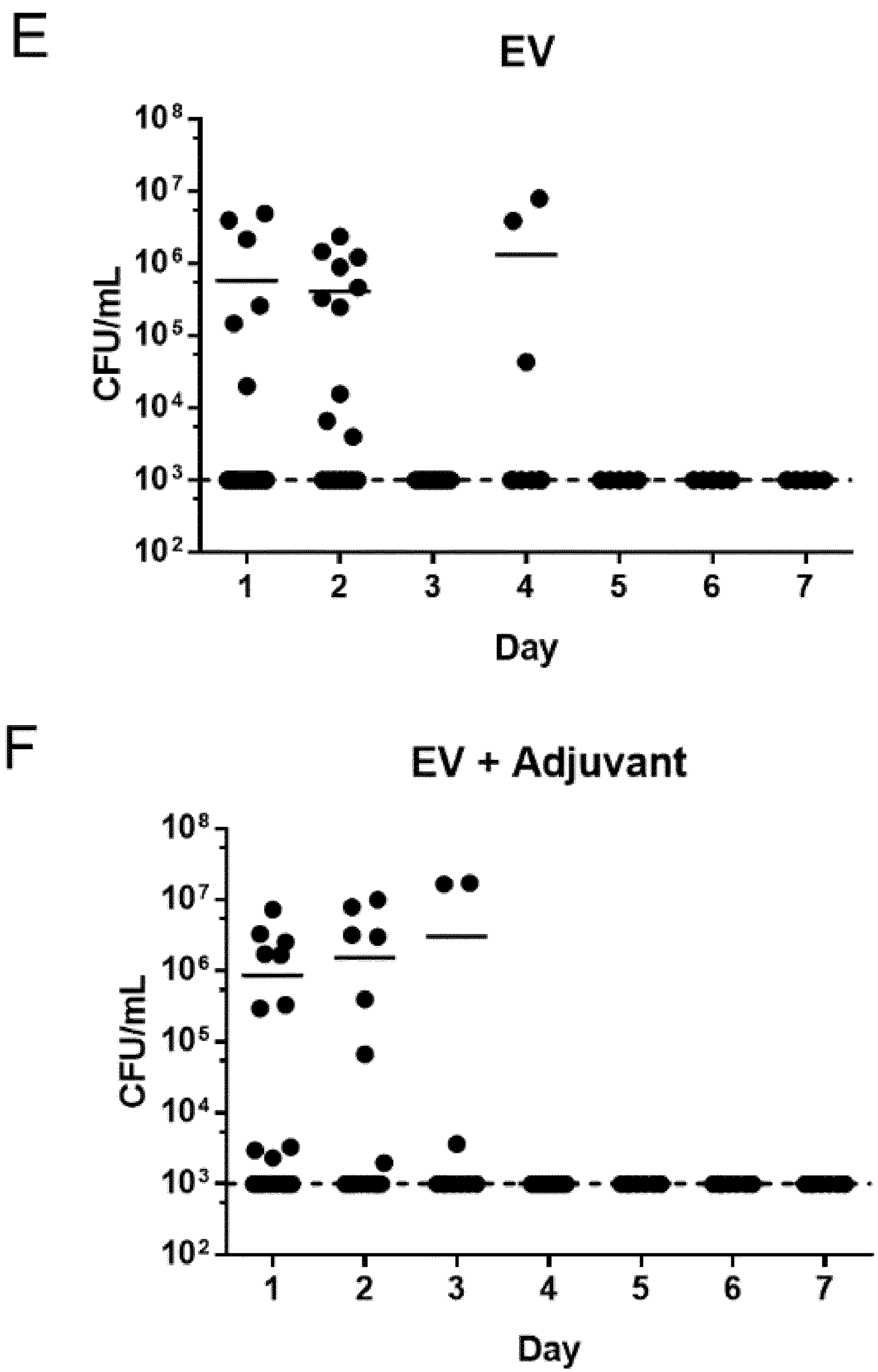

At any time point up to 30 to 60% of healthy preschool children are colonized by *Streptococcus pneumoniae* in the nasopharynx. It is believed that pneumococcal colonization is an immunization event, explaining why nasopharyngeal colonization decreases with age. Serum taken from healthy adults frequently contain antibodies directed against pneumococcal membrane proteins, many of which are highly conserved between pneumococcal strains. *Streptococcus pneumoniae* produces spontaneously, during growth on solid and liquid media, membrane protrusions across the cell wall that pinch off from the bacterial cell without observed lysis resulting in membrane vesicle of different sizes confined by the plasma membrane and enclosing a cytosolic cargo (FIG. 1)(Codemo M. et al. mBio. 2018 Apr. 10; 9(2) e00559-18). We suggest that such membrane protrusions are spontaneously produced during pneumococcal colonization. As membrane vesicle contain only low levels of capsular polysaccharide and cell wall material, their plasma membranes are readily targeted by complement C3 deposition facilitating uptake into antigen presenting cells (Codemo et al., supra). Membrane vesicles contain the entire set of known cytoplasmic membrane proteins including all known lipoproteins, hydrophilic proteins anchored to the outer leaflet of the plasma-membrane through their N-terminal lipid moiety attached to a conserved cysteine (FIG. 1) (Codemo et al., supra). In addition, many choline binding proteins are also found on membrane vesicle, probably associated to the choline residues decorating the membrane associated lipoteichoic acids. Many membrane bound proteins have specialized localizations, such as those involved in septum formation and cell division. We hypothesize that the superior immuno-protective effects found here of membrane particles isolated from solid agar plates (MPs) over extracellular vesicles (EVs), isolated from liquid growing cells (FIG. 6), could be that the former are enriched for membrane proteins localized to the septum region, whereas the latter are also the result of vesicle formation following bacterial autolysis.

There is an urgent need for a new pneumococcal vaccine approach especially for the elderly against IPD. It has been demonstrated that high age is the main risk factor for attracting IPD. The underlying mechanisms are not known but could be due to a waning immune memory from nasopharyngeal exposure events during childhood. In the post-PCV vaccination era the elderly are protected from IPD caused by pneumococcal strains expressing vaccine type capsules (VT), since VT strains have been eliminated from the nasopharynx of vaccinated children. However, PCV vaccination in children has resulted in replacement of VT with non-vaccine types (NVT) strains also in non-vaccinated age groups such as the elderly. An elderly vaccine should ideally be protective irrespective of serotype thereby including NVT-strains and strains producing a serotype 3 capsule. Even though serotype 3 is included in PCV13, it is still a major serotype causing IPD particularly among the elderly. Here, we show that intranasal immunization of mice with MP from serotype 4 protect against heterologous challenge with strains of serotype 1 and 3. Also, we find that this serotype-independent protection is antibody-dependent, but not dependent on the cytotoxin pneumolysin, since deletion of pneumolysin in the MP does not affect the protective effect. Moreover, we find that although the highly diverse choline binding protein PspA is a dominant immunogen in the MP, it only marginally contributes to the homologous serotype protection observed, and it is not required for cross-protection. In fact, the MP antigens from hosts with deleted PspA unexpectedly conferred better cross-protection than native MP antigens (FIG. 8 C-E).

Importantly, we identify two highly conserved pneumococcal membrane-anchored liproproteins, MalX and PrsA, as the major protective antigens in the MP, and they are both needed for protection. MalX is part of an ABC transporter complex and binds maltooligosaccharides of various sizes. MalX was in a signature mutagenesis screen identified as a protein required for lung-infection in an intranasal challenge model (Hava and Camilli, 2002, Mol Microbiol 45, 1389-1406), and serum antibodies directed against MalX have been detected in healthy adults (Giefing et al., 2008 J Exp Med 205, 117-131). PrsA is a conserved cis-trans prolyl isomerase that facilitate protein secretion by promoting extracellular folding of several secreted proteins. PrsA has been shown to contribute to nasopharyngeal colonization in a murine model, and also enhances bacterial resistance to phagocytosis. It was suggested that these effects by PrsA may by indirect by promoting proper folding of adhesins and other virulence associated surface proteins (Cron et al., 2009 Microbiology 155, 2401-2410). We suggest that intranasal immunization with membrane particles elicits neutralizing antibodies to the two natively folded MalX and PrsA that prevent bacterial proliferation in the respiratory tract. The antigenic epitopes generating protective antibodies to MalX and PrsA are not known, and remain to be studied. However, human antibodies have been demonstrated to recognize an epitope present in the signal peptide of MalX (Giefing et al., 2008, supra), an epitope only present in the nascently secreted polypeptide prior to its excision by the leader peptidase.

General Statements Relating to the Present Disclosure

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

The following examples are not to be regarded as limiting. For further information on the experimental details, the skilled reader is directed to a separate section titled Materials and Methods.

Figure 2:
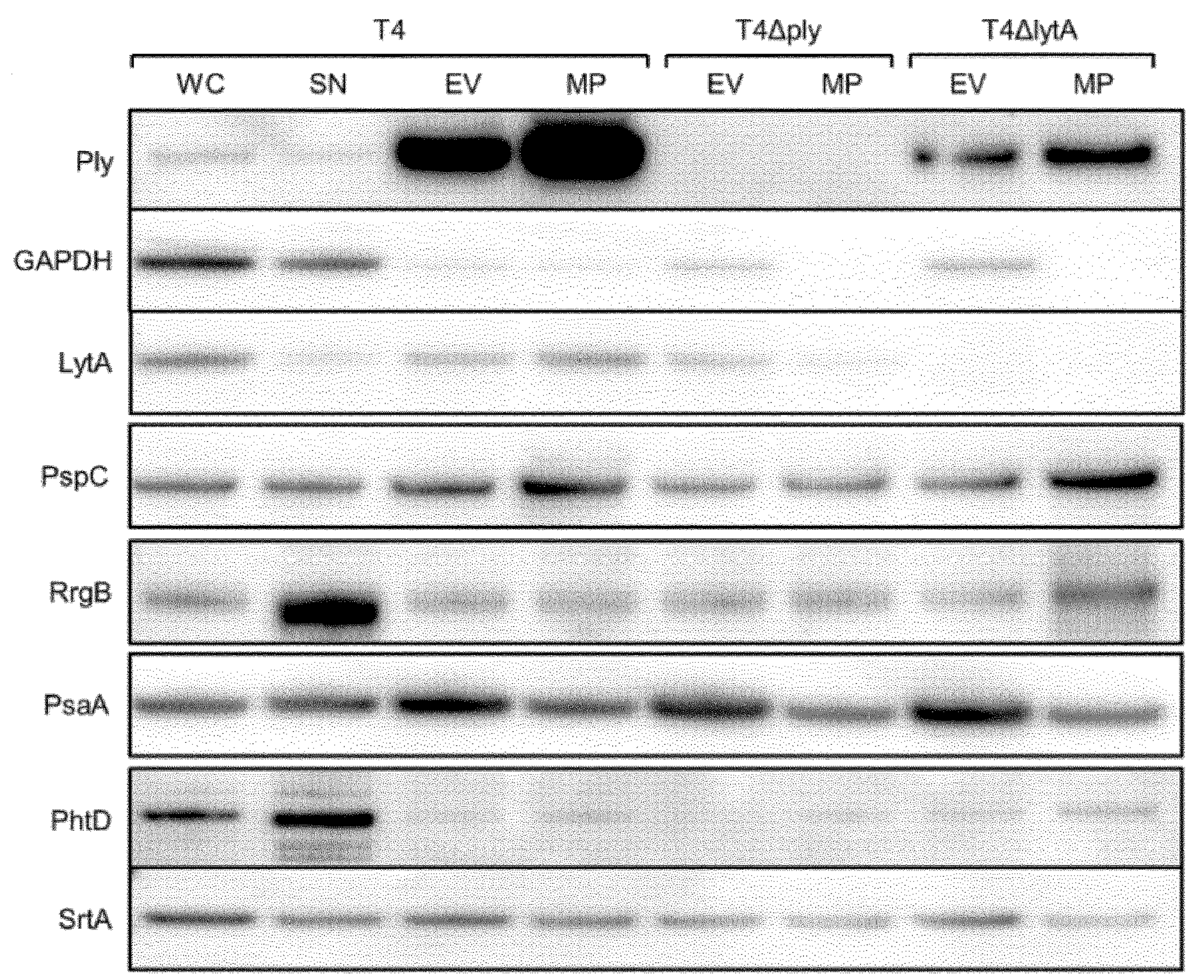
FIG. 2. Protein content of extracellular vesicles (EVs) and membrane particles (MPs). Immunoblot detection of pneumococcal proteins and virulence factors present in EVs and MPs isolated from wild-type strain S. pneumoniaeT4 (T4 WT), and its isogenic deficient mutants in pneumolysin (T4Δply) and LytA (T4ΔlytA).
Figure 7:
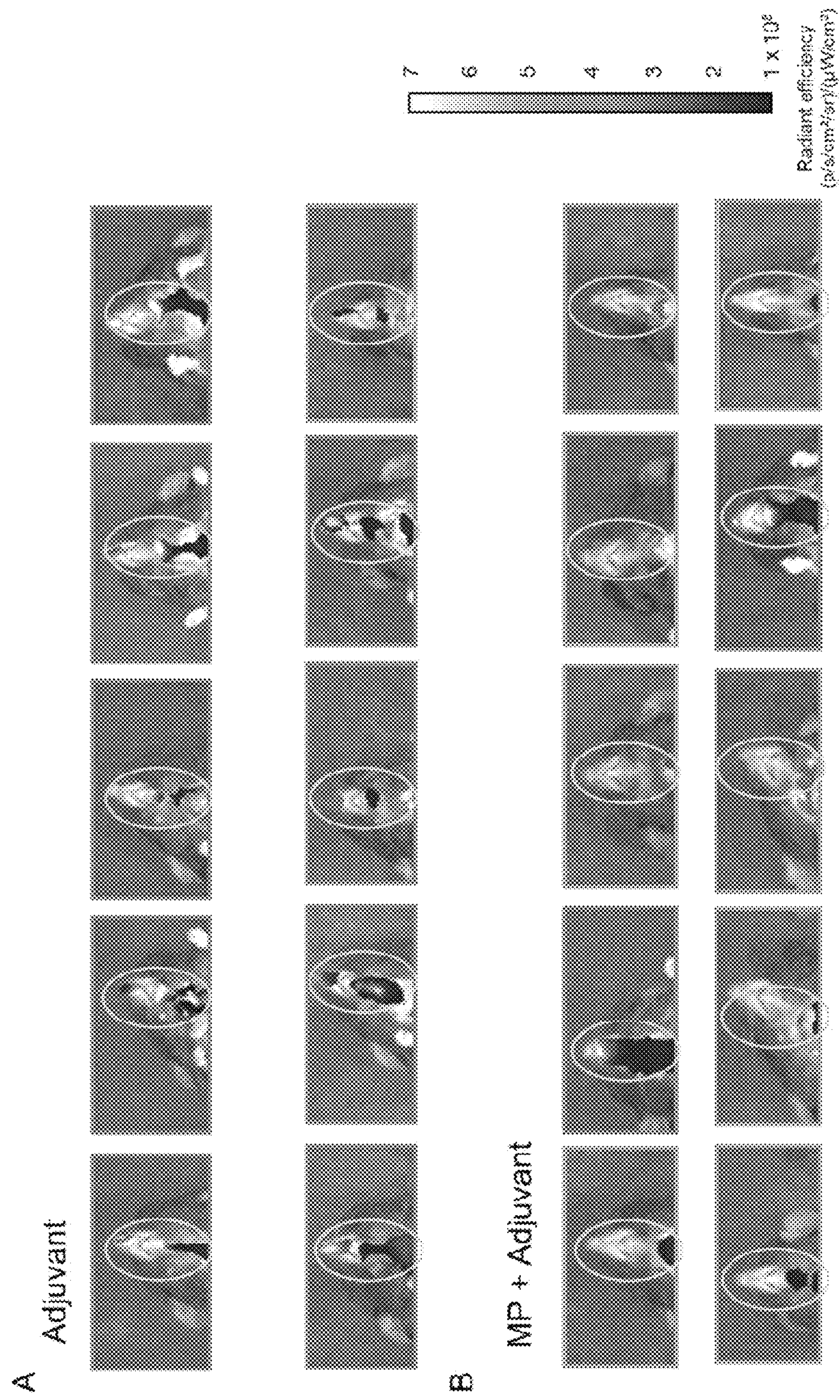
FIG. 7. Immunization with MP reduces pneumococcal colonization of the upper respiratory tract in vivo. IVIS imaging of the fluorescent signal generated by pneumococci present in the upper respiratory tract of mice immunized with (A) adjuvant only or with (B) MPs from strain T4+Adjuvant, and then challenged with a strain of serotype 1 (BHN733). ROIs (Regions of Interest) have been defined per each mouse (ROIs within orange ovals) focusing on the nasopharyngeal tract. Mice that did not survive are marked with red borders and mice that survived are marked with green borders. (C) Per each group ("Adjuvant" and "MPs+Adjuvant") average and standard deviation of the bacterial fluorescent intensity have been calculated based on the fluorescent intensity value of each mouse per group (ten mice per group). *=p<0.05.
Figure 7C:
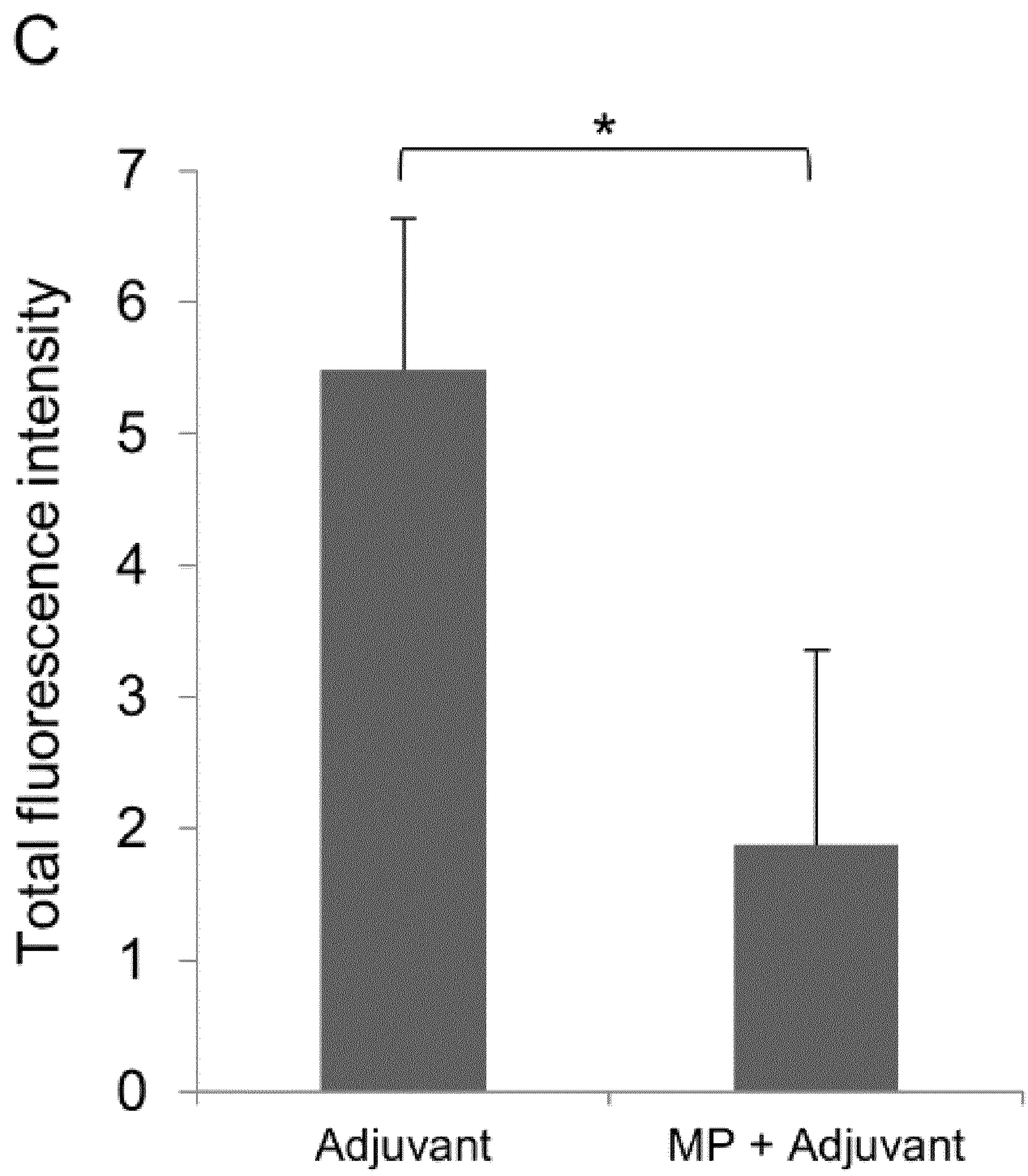

Example 1: Intranasal Immunization with MPs Confers Serotype-Independent Cross-Protection Against IPD The inventors isolated vesicles from plate-grown pneumococci as a proxy for biofilm growing pneumococci during nasopharyngeal carriage, and called them membrane particles (MP) (see FIGS. 1A,B and FIG. 2 for characteristics). Wild-type mice (C57BL/6) were immunized twice intranasally with MP isolated from the strain T4 (TIGR4), alone or combined with the adjuvant aluminium hydroxide, or with phosphate-buffered saline (PBS), or adjuvant alone for the control groups. After four weeks, mice were infected intranasally with $5\times10^6$ colony forming units (CFU) of the serotype 1 strain BHN733. Mice were followed for seven days and survival was recorded. Heterologous serotype challenge with immunization using MP+adjuvant from T4, and infection with serotype 1, conferred 80% survival. Also, in the absence of adjuvant the inventors observed a significant protection (65% survival) (FIG. 3A). Bacterial loads in the lungs were consistent with the survival data, with lower bacterial numbers in immunized mice as compared to control mice treated with adjuvant only (FIG. 3B). Bacterial CFU in the blood was monitored daily until sacrifice (FIG. 4A-D). For the PBS and adjuvant groups, only mice with no bacteraemia survived. Seven of the mice vaccinated with MP+adjuvant cleared the bacteria from the blood, suggesting that even though the immunization was intranasal, immune clearance occurred systemically. The following experiments were done using MP (and not EV isolated from liquid cultures) since intranasal immunization of mice with MPs from strain T4 gave higher protection, lower pneumococcal numbers in the upper respiratory tract, and higher antibody levels after immunization than what was observed using EV from the same strain (FIG. 3A-B, FIG. 4A-D, and FIG. 6). The effect of MP-immunization on colonization was studied using the IVIS imaging system to monitor mice after sacrifice. The inventors found that the bacterial density in the nasopharyngeal tract of mice immunized intranasally with MP+adjuvant was significantly lower than what was observed in mice immunized with adjuvant alone. Indeed, the eight surviving mice immunized with MP+adjuvant showed no fluorescent signal (FIG. 7). In summary, intranasal immunization with MP gives a serotype independent cross-protection against IPD, and also reduces the pneumococcal load in the upper airways.

Figure 5C:
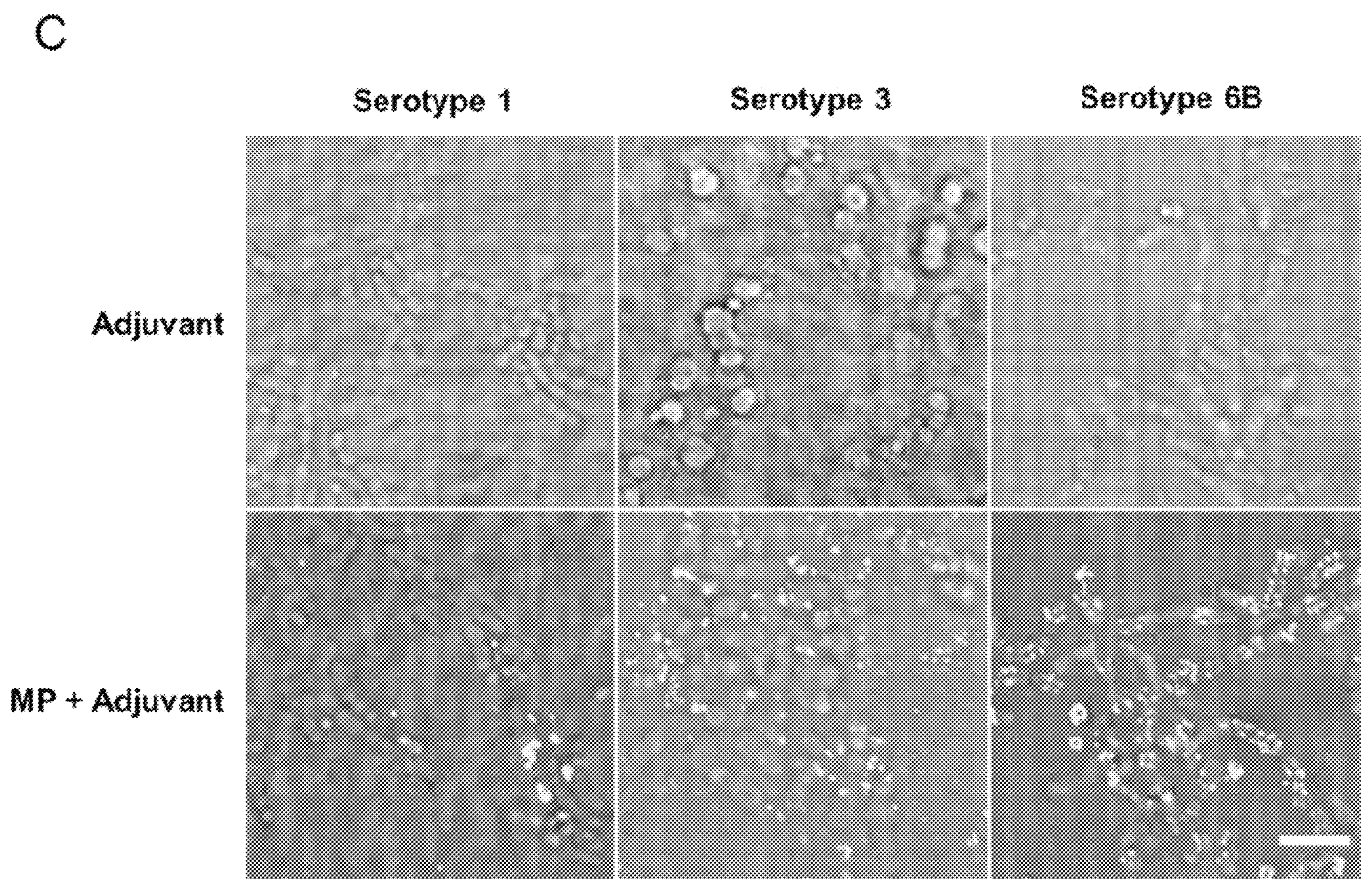
FIG. 5. Intranasal immunization with MPs elicits production of pneumococcal-specific IgG. Mice were immunized intranasally with MP from strain T4. Using ELISA, pneumococcal specific IgG were detected in wells coated with (A) wild type T4, or (B) T4R (isogenic mutant in the capsule of T4) bacteria. Each dot represents one mouse serum. The low responder mice in the MPs+Adjuvant and MP groups are those that did not survive after serotype 1 challenge. These mice are highlighted in the graphs within boxes with red borders. (C) Immunofluorescence microscopy of pneumococcal strains belonging to serotypes 1, 3 and 6B stained (green) using pooled sera from mice immunized with only Adjuvant or T4 MP+Adjuvant as primary antibodies. Scale bar: 5 μm. (D) RAW 264.7 macrophages were incubated with *S. pneumoniae* serotype 1 pre-treated with pooled sera from mice immunized with Adjuvant or MPs+Adjuvant, and bacterial adhesion to the cells was measured. (E) Effect on phagocytic killing by adding the sera in (E) was estimated by calculating bacterial survival inside the cells. Data are represented as means +/−SEM of three independent experiments. *=p<0.05.

Example 2: Immunization with MPs Leads to Production of Pneumococcal-Specific Antibodies with Opsonophagocytic Activity Next, the inventors analyzed the presence of pneumococcal-specific antibodies in sera of mice immunized intranasally with MP from T4. Using enzyme-linked immunosorbent assay (ELISA), they detected IgG specific for whole heat-inactivated T4 in sera from mice two and four weeks after immunization, and the IgG levels were higher in immunized mice than in the adjuvant and PBS control groups already two weeks after immunization, and significantly higher after four weeks (FIG. 5A). Furthermore, the inventors detected IgG with affinity for the non-encapsulated mutant strain T4R, thus indicating reactivity to non-capsular antigens (FIG. 5B). In order to further assess the presence of pneumococcal-specific antibodies, the inventors performed immunofluorescence staining of three pneumococcal strains, BHN733, BHN428, and BHN191, of serotypes 1, 3, and 6B respectively, using sera from mice immunized with T4 MP+adjuvant as the source of primary antibodies. For all the three pneumococcal serotypes, the inventors observed fluorescence signals on the bacterial surface (FIG. 5C), while no fluorescence signals were detected when sera from mice treated with adjuvant only was used (FIG. 5C). To investigate the opsonophagocytic activity of the cross-reactive antibodies, serotype 1 pneumococci were incubated with sera from mice immunized with T4 MP+adjuvant, and subsequently incubated with RAW mouse macrophages. The ratio of adhered bacteria was significantly higher when pneumococci were incubated with sera from mice immunized with MP+adjuvant, compared to adjuvant alone (FIG. 5D). Also, these pneumococci with better adherence were significantly less able to survive inside the cells compared to pneumococci incubated with control serum (FIG. 5E).

Example 3: MPs from Serotype 4 Confer Antibody-Dependent Protection Against Challenge with Serotype 3 Pneumococci Since there is an urgent need for a vaccine against serotype 3, the inventors purified and characterized MP from the serotype 3 strain BHN428. These MP were larger than those from T4 with diameters up to 850 nm, possessed more cytosolic proteins and less predicted cell wall associated, and secreted proteins (FIG. 1A). Mice were immunized intranasally with MP of serotype 3. In the seven-days-survival experiment, all mice immunized with MP of serotype 3+adjuvant survived, while the adjuvant treated control mice all died within four days (FIG. 3C). Immunized mice showed lower bacterial numbers in the lungs and blood as compared to adjuvant-treated mice (FIG. 3D, FIG. 4E-F). Immunization using MP from T4 and challenge with serotype 3 bacteria (BHN428), provided 50% cross-protection (FIG. 3C), and the bacterial load in the lungs of surviving mice tended to be lower than for the adjuvant control, and for those that succumbed to infection (FIG. 3D). The ten mice that showed lower lung counts had no detectable bacteria in the blood (FIG. 4G). These data show that MPs of type 3 show full protection against homologous challenge in mice. These data also indicate that T4 MP evoke cross-protection against genetically distant pneumococcal lineages, such as of serotype 3.

Example 4: Protection Conferred by MPs is Antibody-Dependent

To investigate whether the protection is antibody-dependent, the inventors immunized B cell-deficient mice (MuMt knock-out mice) with MP from serotype 3 and challenged intranasally with the same strain. In the seven-days survival experiment, none of the B cell-deficient mice survived, demonstrating that the protection is antibody-dependent (FIG. 3C). Bacterial numbers in the lungs and blood were high and similar to what was detected in wild-type mice given adjuvant only, and significantly higher than in wild-type mice immunized with the same MP (FIG. 3D, FIG. 4F-H). Thus, data indicates that intranasal immunization with MP provides an antibody-mediated protection.

Example 5: The Cytotoxin Pneumolysin is not Required for MPs to Confer Protection Against IPD The pneumococcal cytotoxin pneumolysin (Ply) has been discussed as a vaccine candidate since Ply-deficient strains are highly attenuated in mice infection models. The inventors investigated whether protection is Ply-dependent using MP isolated from an isogenic strain lacking Ply (T4Δply). Importantly, mice immunized with MP from T4Δply and challenged with T4 showed 100% protection (FIG. 3E). Also, these mice showed similar CFU in the lungs as mice immunized with MP from T4, and had no bacteria in the blood (FIG. 3F, FIG. 41-K). The inventors conclude that Ply is not crucial for the protection against IPD.

Example 6: PspA is a Major Protein in MPs, but the Cross-Protection is not Dependent on PspA To identify which pneumococcal proteins in MP are responsible for the protection, T4 was grown in liquid medium, and then washed with elevated concentrations of choline chloride to release choline binding proteins that non-covalently associate with the cell surface.

Figure 8A:
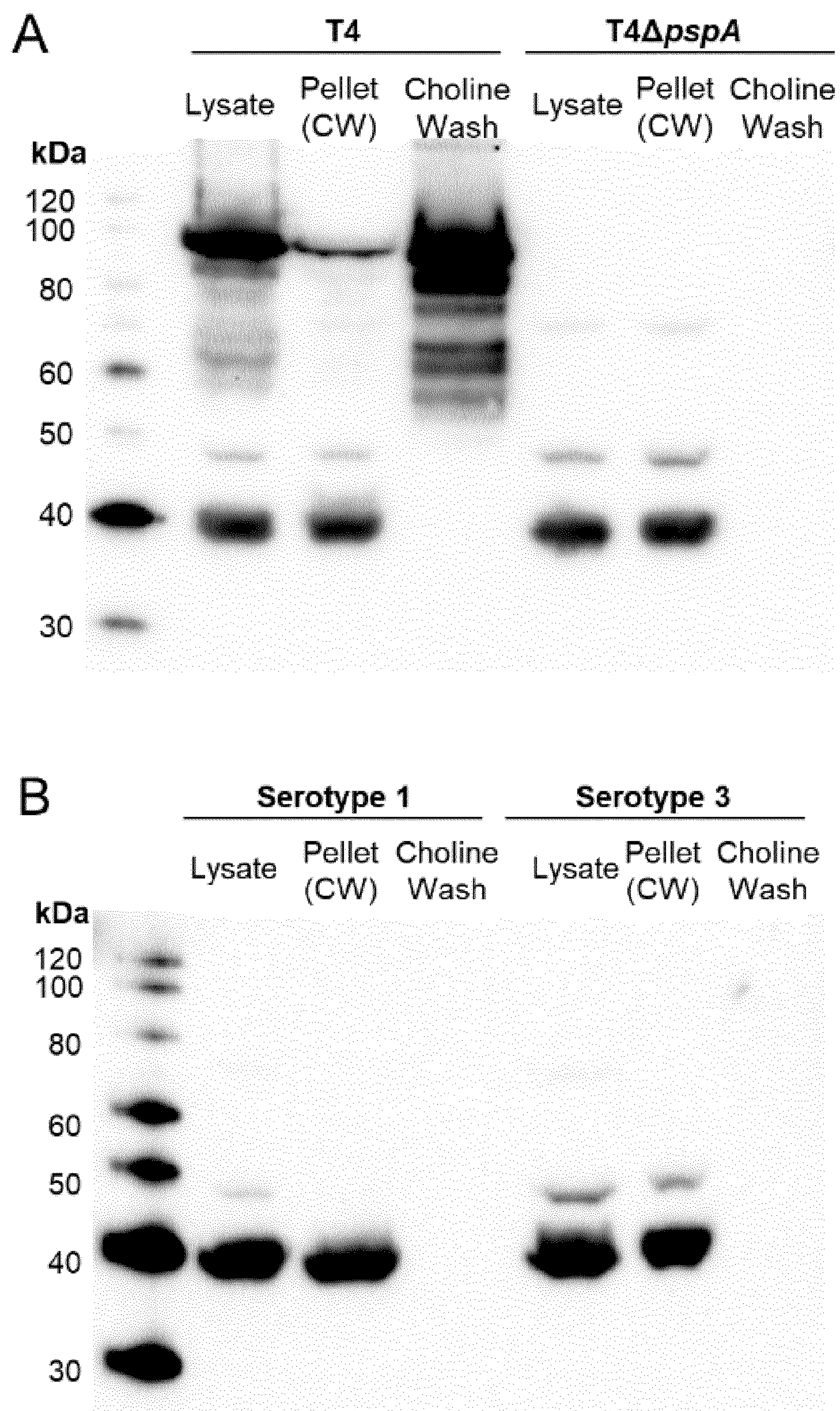
FIG. 8. Cross-protection against IPD is not dependent on PspA. (A, B) Western blot analysis of bacterial lysates, supernatant samples from choline washed (cells treated with 5% choline chloride to release choline binding proteins) and from lysates of corresponding choline washed cells (Pellet CW). Binding of sera from mice immunized with T4 MPs+Adjuvant (used as primary antibody) to (A) T4 and T4ΔpspA, (B) serotype 1 and serotype 3 cells were analyzed. Sera came from mice included in experiments represented in FIG. 1A-B. (C-E) Percentage of mice immunized with either T4 MP or T4ΔpspA MP that survived an intranasal infection with (C) T4, (D) serotype 3 (BHN428) or (E) serotype 1 (BHN733) bacteria. 10 mice per group (the group immunized with T4ΔpspA MP and infected with serotype 1 had 9 mice), 5 mice/pneumococcal strain immunized with adjuvant as control. (F-H) Number of bacteria (CFU) in the lungs of mice infected with (F) T4, (G) serotype 1 (BHN733) or (H) serotype 3 (BHN428) bacteria at sacrifice, each dot represents one mouse, *=p<0.05, =p<0.01, *=p<0.001, n.s.—not significant.

Western blot analyses of the cell pellets and supernatants of choline washed (cw) cells were performed using sera from immunized mice (with T4 MP) as the source of primary antibodies. A major band of approximately 80 kDa was observed mainly in the supernant fraction, that was absent in a T4ΔpspA mutant, thus identifying it as the highly immunogenic choline binding pneumococcal surface protein PspA (FIG. 8A). PspA has been described as a putative vaccine candidate against IPD and colonization, but its sequence is highly variable among clinical strains, which likely explains why no PspA bands were observed in choline washed samples from BHN733 (serotype 1) and BHN428 (serotype 3) (FIG. 8B). However, two additional protein bands of slightly less than 40 and 50 kDa respectively were observed in the lysates and pellet fractions of choline-washed cells of T4, T4ΔpspA, and of the serotype 1 and 3 strains (FIGS. 8A and B).

Figure 9A:
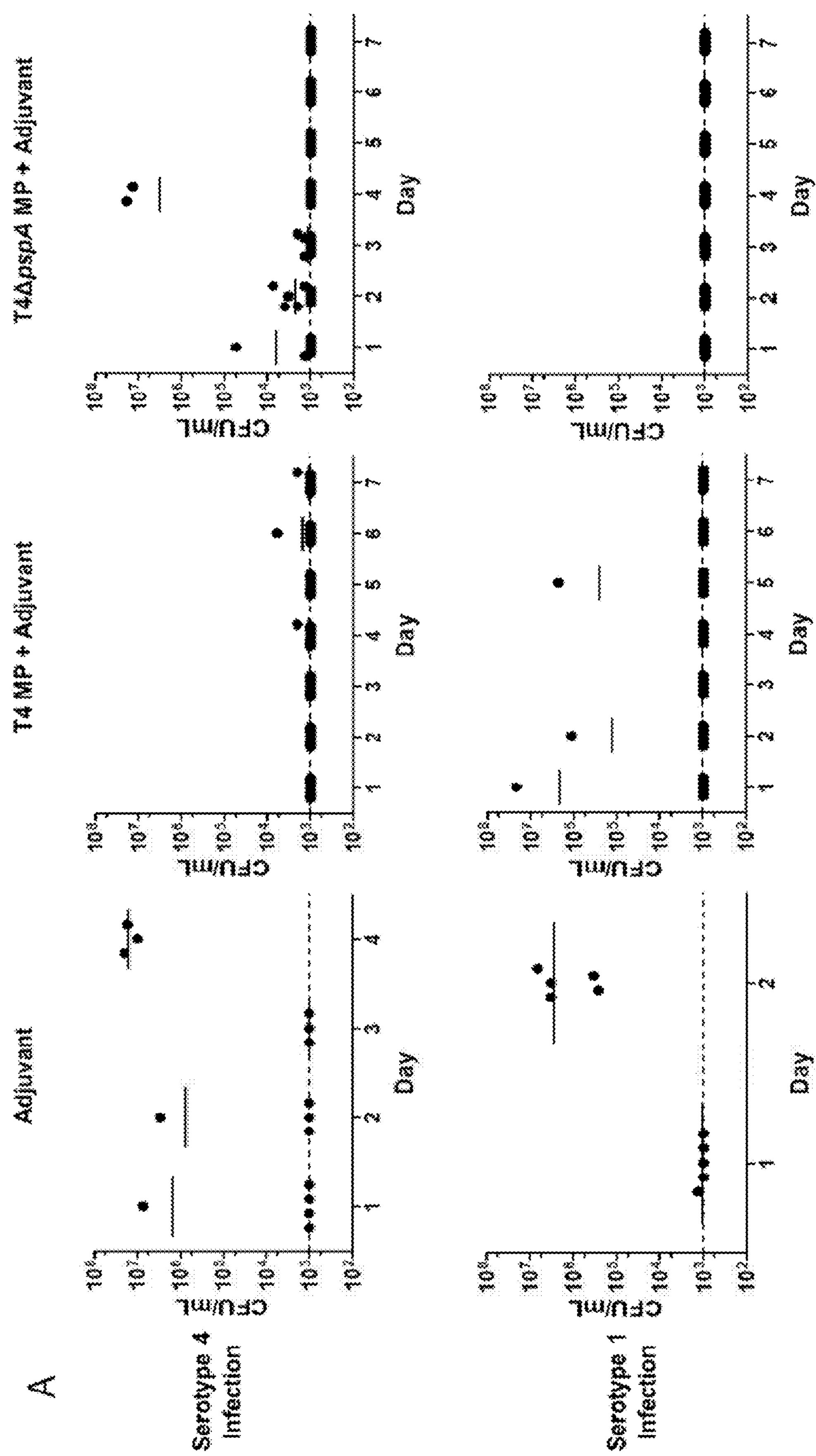
FIG. 9. Intranasal immunization with MP from T4ΔpspA elicits the same or even higher cross-protection against intranasal challenge with strains of serotype 1 and serotype 3. Intranasal immunization with MP of T4 or its isogenic mutant in PspA, T4ΔpspA, subsequently followed by bacterial challenge with strains T4, serotype 1 (BHN733) or serotype 3 (BHN428), in a 7-day survival experiment. (A) Number of bacteria (CFU) in the blood of mice, each dot represents one mouse. (B) Using ELISA assays, pneumococcal specific IgG was detected in wells coated with T4, serotype 1 or serotype 3 pneumococci. Each dot represents one mouse serum collected from mice used in the survival in vivo experiment showed in FIG. 3C-E. *=p<0.05; **=p<0.01; n.s.—not significant.
Figure 9A:
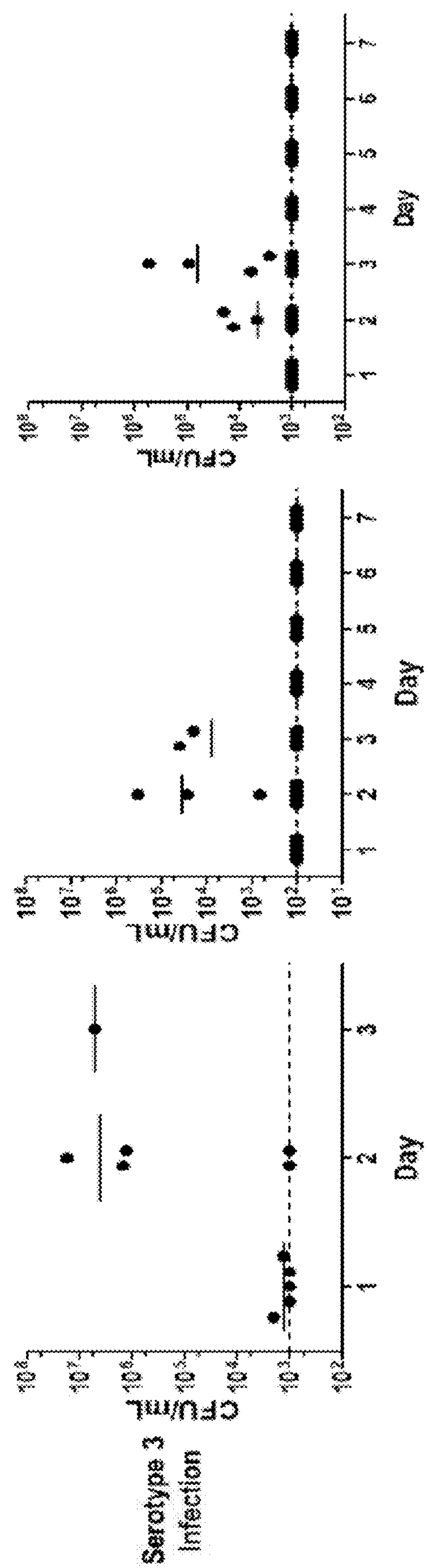
Figure 9B:
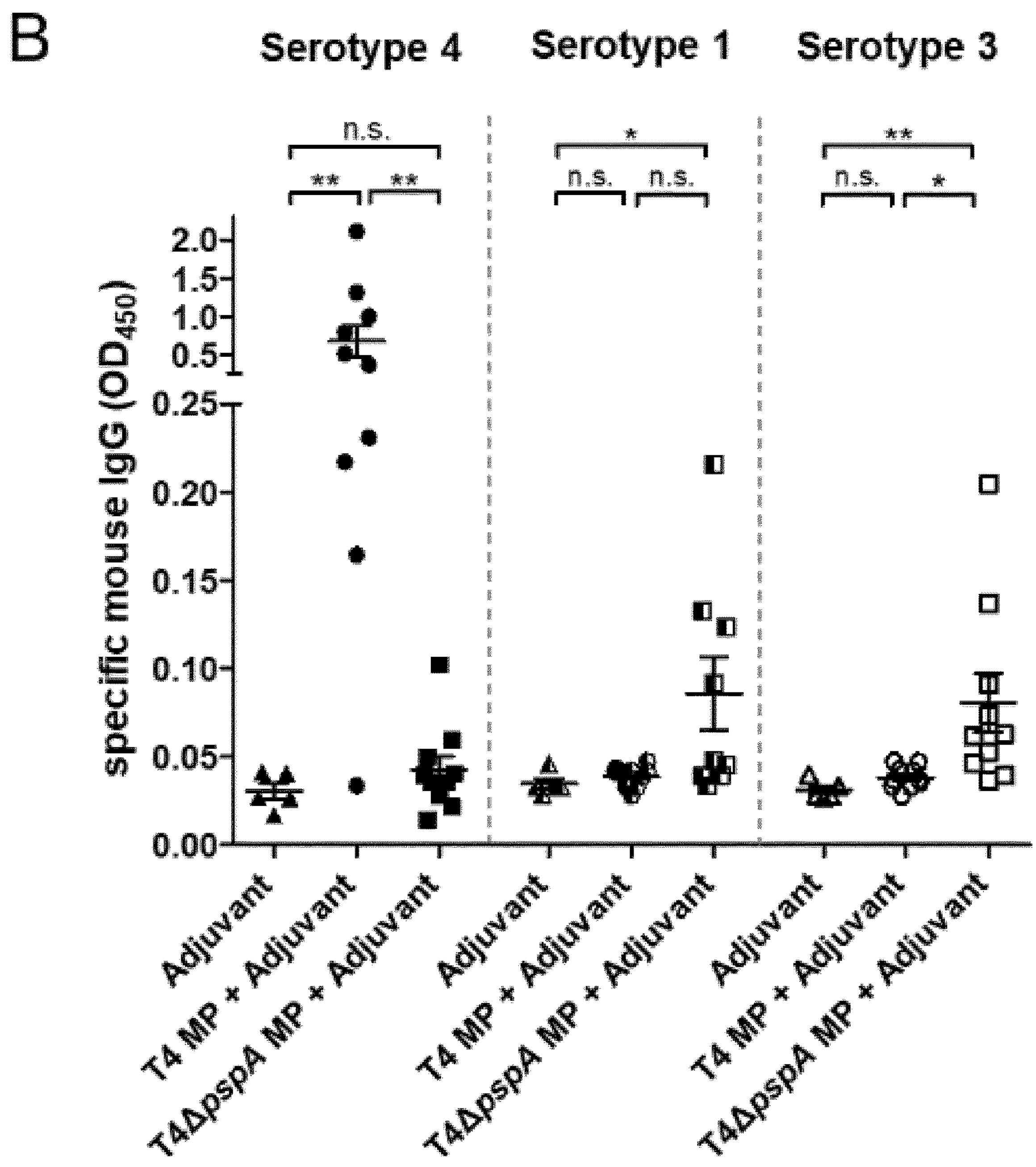

To study the role played by PspA for protection by MP, the inventors immunized mice with MP from the mutant strain, T4ΔpspA, and challenged with T4. Immunized mice showed 80% protection (FIG. 8C), suggesting that antigens other than PspA provide protection. Indeed, when mice immunized with T4ΔpspA MP were challenged with the serotype 1 strain BHN733, a 100% cross-protection was observed, reinforcing that the protective antigens in MP were neither PspA, nor the capsular polysaccharide (FIG. 8D). Similar results were obtained when mice were challenged with serotype 3 pneumococci (BHN428). Here, a 60% protection was observed with T4ΔpspA MP which was in the same range as for T4 MP (FIG. 8E). For all three infection experiments, the bacterial loads in the lungs (FIG. 8F-H) and blood (FIG. 9A) were low in surviving mice. ELISA assays, and coating with serotype 1, 3 and 4 pneumococci respectively, showed higher IgG titers in mice immunized with MP from T4ΔpspA compared to T4 MP (FIG. 9B). Unexpectedly, the T4ΔpspA MPs were better in conferring protection against Serotype 1 infection than wild-type T4 MPs (FIG. 8D, G), while being indistinguishable in efficacy against Serotype 3 or 4 infection (FIG. 8CF, 8EH)

Figure 10A:
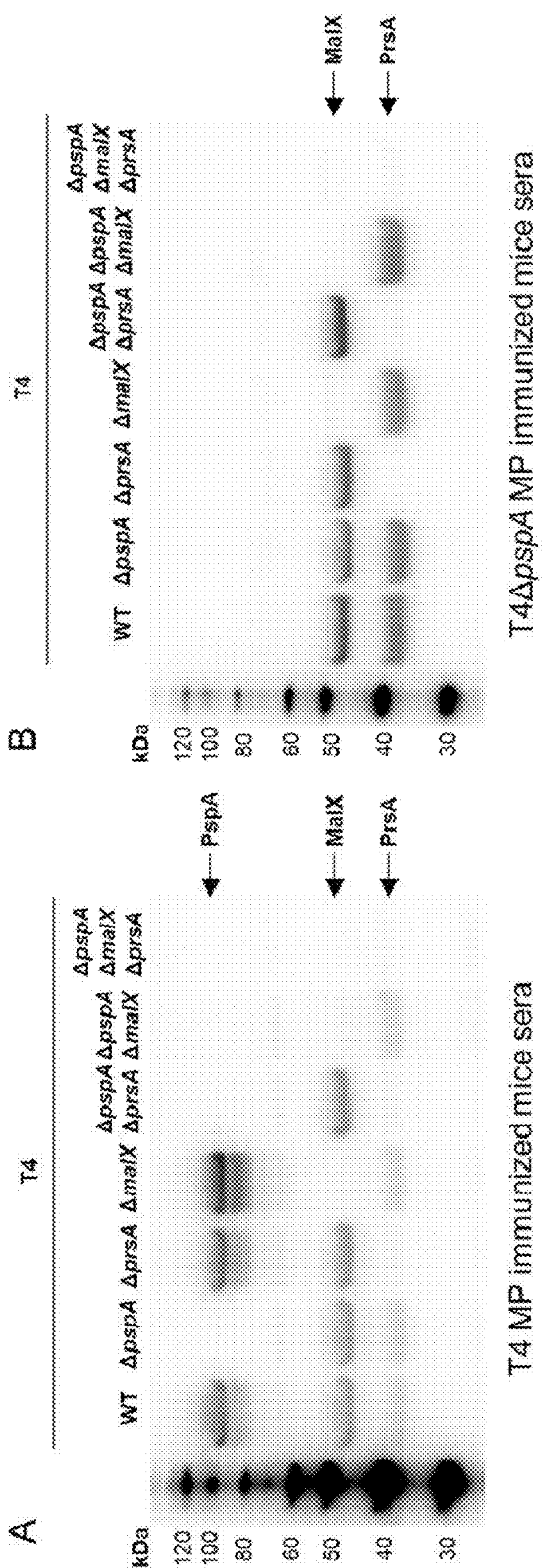
FIG. 10. Cross-protection against IPD is mediated by the lipoproteins PrsA and MalX. (A, B) Validation of results from the IP experiment and MS analysis confirming the identity of the major immunoreactive proteins. Lysates from T4 wildtype (WT), single mutants T4ΔpspA, T4ΔprsA, T4ΔmalX, double mutants T4ΔpspAΔprsA, T4ΔpspAΔmalX, and triple mutant T4ΔpspAΔmalXΔprsA as indicated, were subjected to Western blot analysis. PVDF-membranes were incubated with immune sera from mice immunized with (A) T4 MPs+Adjuvant or (B) T4ΔpspA MPs+Adjuvant. Sera came from mice included in experiments represented in FIG. 3C-E. A second incubation with sheep anti-mouse IgG-HRP conjugated facilitated chemiluminescent detection. (C-E) Percentage of mice immunized with either T4 MPs or T4ΔpspAΔmalXΔprsA MP that survived an intranasal infection with (C) T4, (D) serotype 1 (BHN733) or (E) serotype 3 (BHN428) bacteria. 10 mice per group (the group immunized with T4ΔpspAΔmalXΔprsA MP and infected with T4 included 9 mice). 5 mice/pneumococcal strain were immunized with adjuvant as control. (F-H) CFU in the lungs of mice infected with (F) T4, (G) serotype 1 (BHN733) or (H) serotype 3 (BHN428) bacteria at sacrifice, each dot represents one mouse, *=p<0.05, **=p<0.01, n.s.—not significant.
Figure 11A:
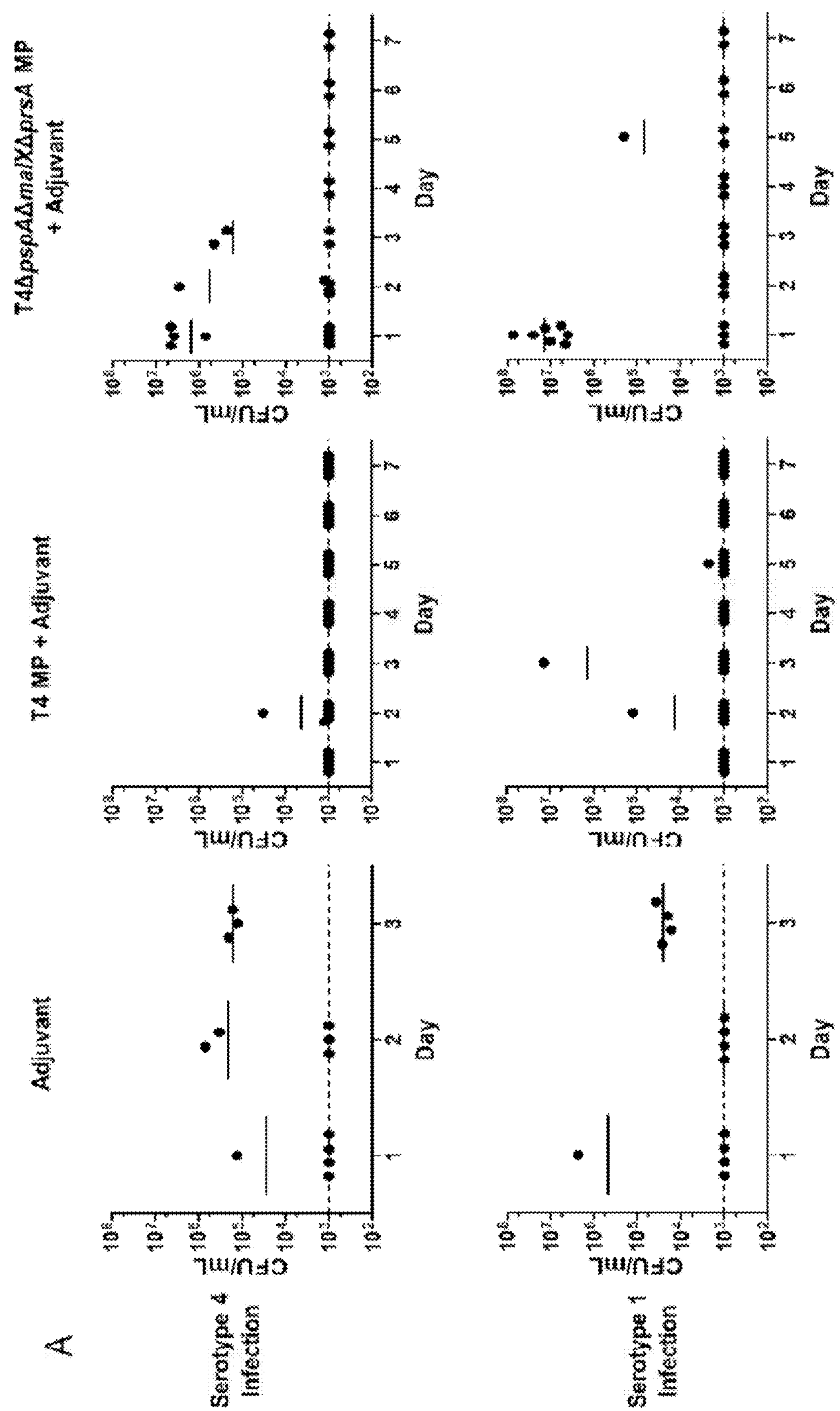
FIG. 11. Mice immunized with MP from T4ΔpspAΔmalXΔprsA are not protected against intranasal challenge with the pneumococcal strains T4, serotype 1 or serotype 3. Intranasal immunization with MPs from T4, T4ΔpspA or T4ΔpspAΔmalXΔprsA, subsequently followed by bacterial challenge with strains T4, serotype 1 (BHN733) or 3 (BHN428), in a 7-day survival experiment, as shown in FIG. 4C-E. (A) Number of bacteria (CFU) in the blood of mice, each dot represents one mouse. (B) Using ELISA analysis, pneumococcal specific IgG was detected in wells coated with T4, serotype 1 and serotype 3 pneumococci respectively. Each dot represents one mouse serum collected from mice used in the survival in vivo experiment showed in FIG. 4C-E. *=p<0.05; =p<0.01; *=p<0.001; n.s.—not significant.
Figure 11A:
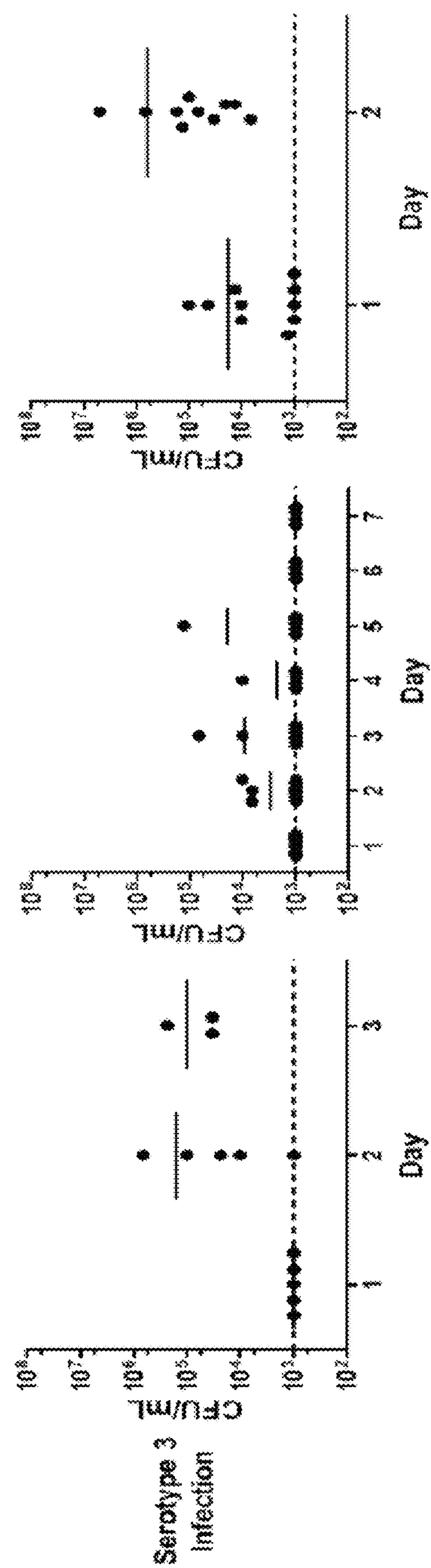
Figure 11B:
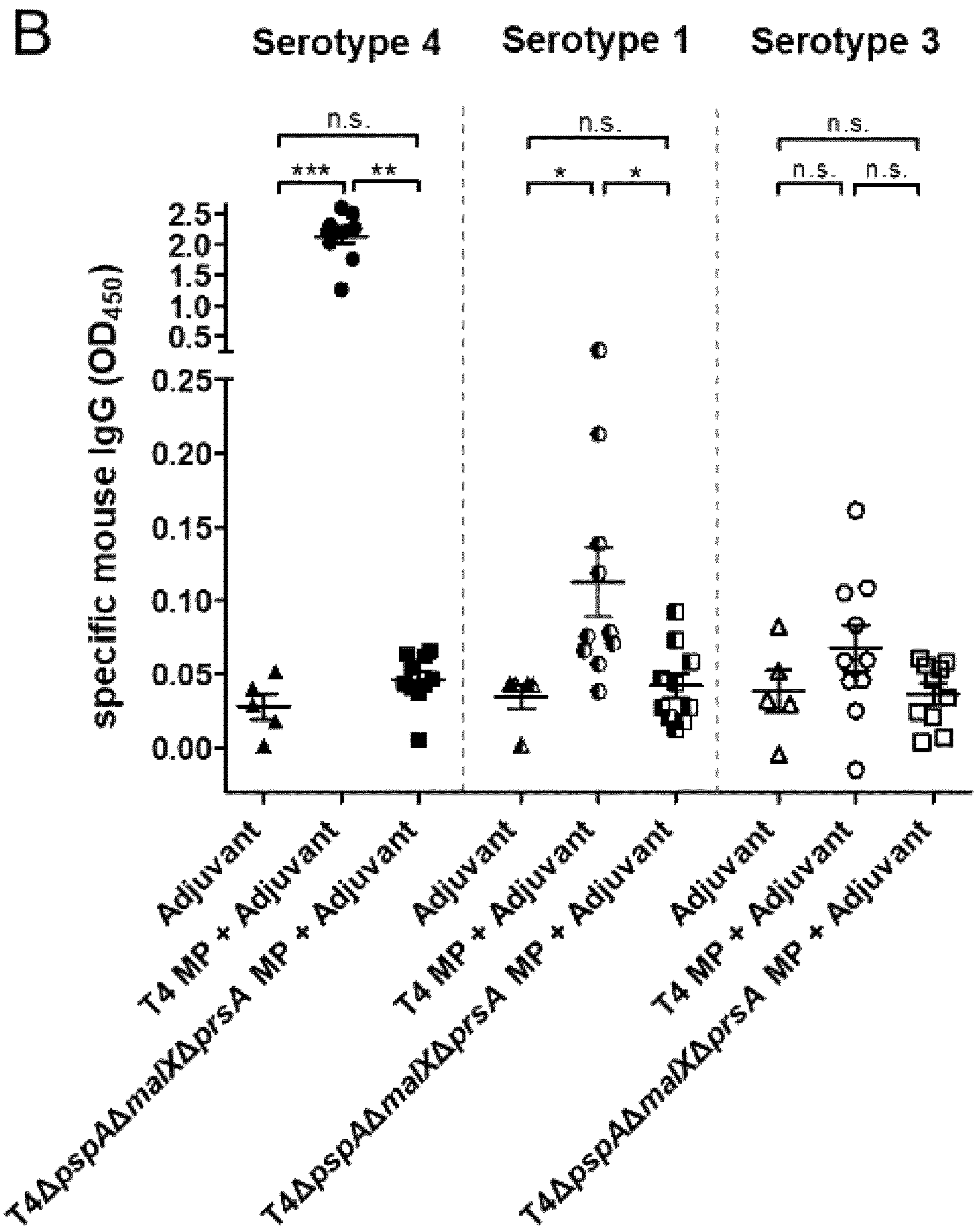

Example 7: Cross-Protection Mediated by Membrane Vesicles Against Invasive Pneumococcal Disease is Dependent on the Lipoproteins PrsA and MalX Since the inventors found that PspA in MP was not important for heterologous serotype protection, the inventors next performed a series of immunoprecipitation (IP) experiments to capture additional putative antigens using sera from mice immunized with MPs from T4 and T4ΔpspA, or from adjuvant treated mice as a control. Antibody-enriched proteins in lysates of T4 were subjected to mass spectrometry analysis for protein identification. Importantly, the hits with the highest scores from IP using sera from T4ΔpspA MP-immunized mice were two lipoproteins, PrsA and MalX. These proteins were not detected in IP with sera from the adjuvant control. As expected, PspA was identified as one of the top hits in the IP with sera from T4 MP, but MalX was also enriched with this sera, albeit with a lower score (Tables A-C). Additionally, the masses of MalX and PrsA corresponded to the immunoreactive bands of ~40 and ~50 kDa that the inventors observed in the lysates and cell pellet fractions by Western blot analysis, see above (FIGS. 8A and 8B). To further validate that PspA, PrsA and MalX were the major reactive proteins from the immune sera, the inventors complemented the IP experiment with a Western blot analysis where blotted lysates from wt T4, and mutants in pspA, prsA and malX were incubated with sera from mice immunized with MP from T4 or T4ΔpspA (FIG. 10A-B). Indeed, sera from T4 MP-immunized mice reacted with three major proteins, and absence of these protein bands in the corresponding mutant background confirmed these proteins to be PspA, PrsA and MalX (FIG. 10A). Thus, although PrsA was not enriched in IP with the T4 MP immune sera, the Western blot analysis clearly showed that this sera still reacted to this protein. Likewise, using sera from mice immunized with T4ΔpspA MPs revealed two major bands of slightly less than 40 and 50 kDa, absent in mutants having a prsA or a malX deletion, thus confirming the identity of these proteins (FIG. 10B).

To further investigate if the identified PrsA and MalX proteins were responsible for the cross-protection, the inventors first isolated MP from a mutant lacking both prsA and malX in the T4ΔpspA background, T4ΔpspAΔprsAΔmalX. Mice were immunized with either MP from T4 or from the triple mutant, and then infected intranasally with either T4, BHN733 (serotype 1) or BHN428 (serotype 3). Immunization with T4 MP showed again 100%, 80%, and 60% protection against these strains respectively, confirming the previous results (FIG. 8C-E). However, when MP from T4ΔpspAΔprsAΔmalX were used for immunization, mice showed only 20% protection towards T4 and type 1 (BHN733), and no protection towards type 3 (BHN428) (FIG. 10C-E). Lung and blood CFU were in accordance with these findings, as were IgG titers (FIG. 10F-H, FIG. 9A-B).

Figure 12:
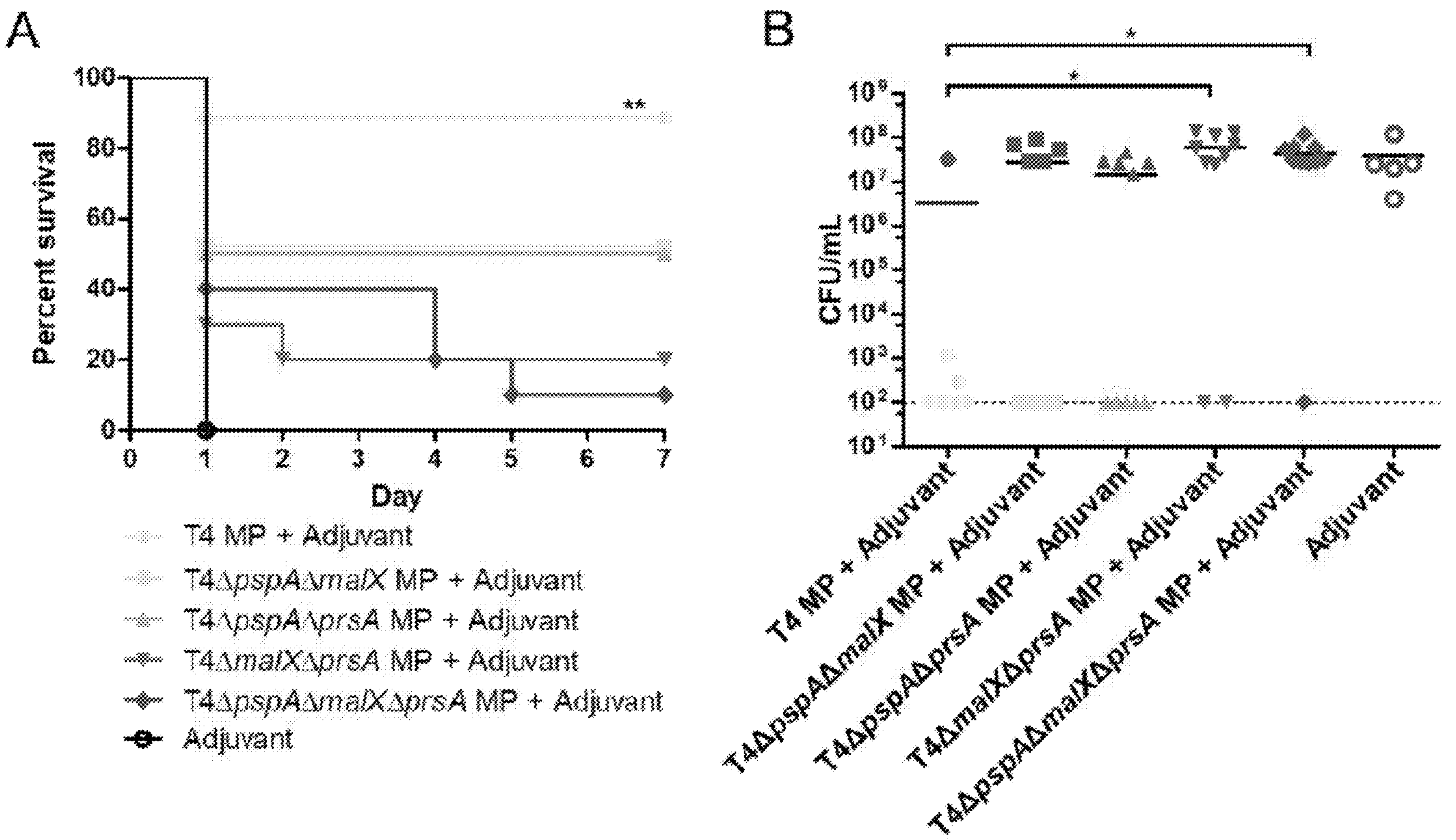
FIG. 12. Lipoproteins PrsA and MalX in MPs from pneumococci are both required for cross protection against serotype 1 infection (A, B) Mice were immunized with MPs purified from different serotype 4 mutants, lacking the antigens PspA, MalX and PrsA in different combinations and challenged with serotype 1 pneumococci. (A) Percentage of mice immunized with either T4 MPs+Adjuvant, T4ΔpspAΔmalX MPs+adjuvant, T4ΔpspAΔprsA MPs+adjuvant, T4ΔmalXΔprsA MPs+adjuvant or T4ΔpspAΔmalXΔprsA MPs+Adjuvant or Adjuvant only that survived an intranasal infection with serotype 1 (BHN733) bacteria. (B) CFU in the lungs of mice upon sacrifice. Each dot represents one mouse. Red-colored dots symbolize mice sacrificed before the end of the experiment. 10 mice per group (the group immunized with T4 MP included 9 mice). 5 mice/pneumococcal strain were immunized with adjuvant as control. *=p<0.05, **=p<0.01.
Figure 13:
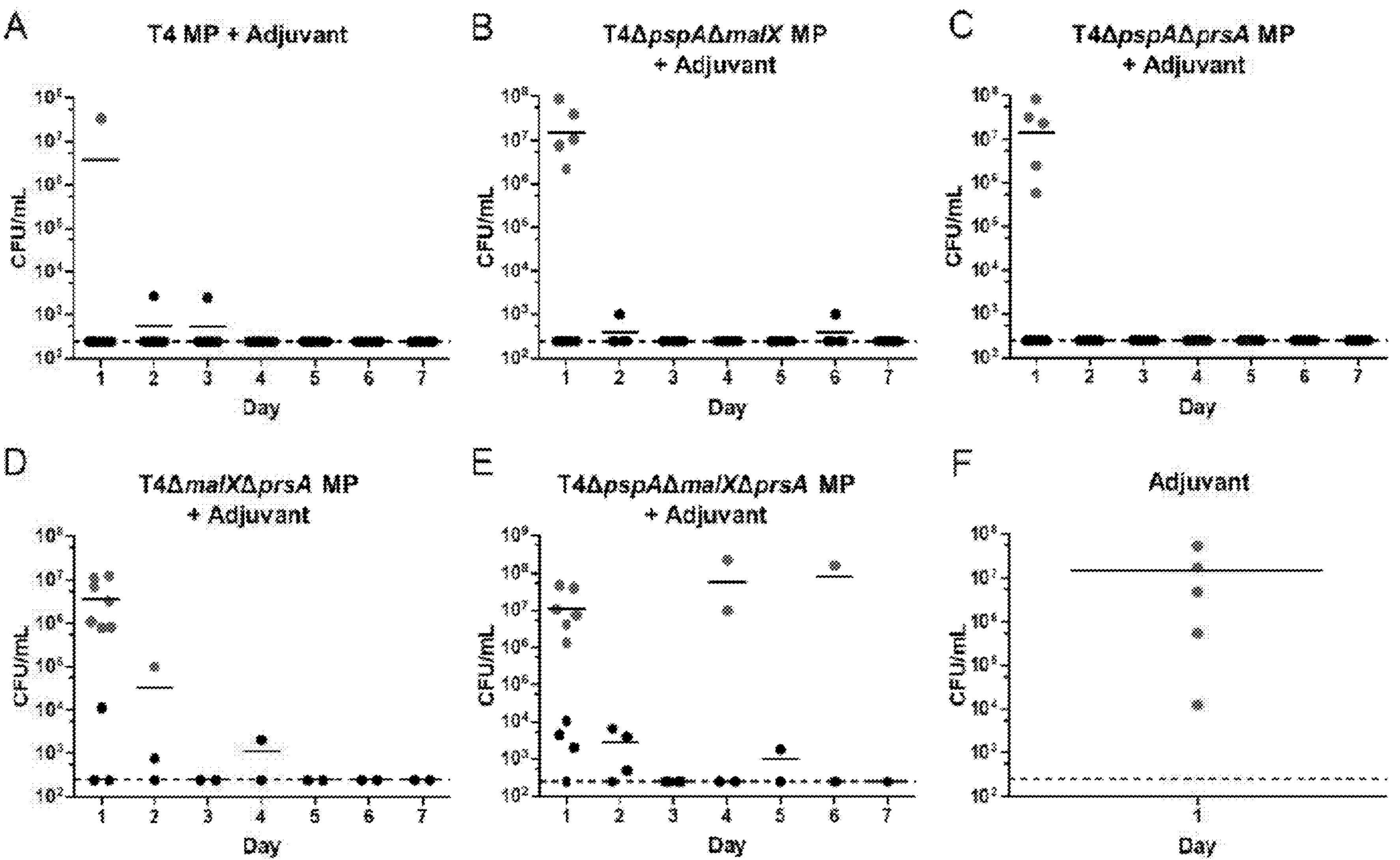
FIG. 13. MalX and PrsA are both required for protection against invasive pneumococcal disease by serotype 1

To further study whether the cross protection depends on both lipoproteins, three new mutant strains were created in the strain T4 where pspA and malx, or pspA and prsA or malX and prsA were deleted (FIG. 12A-B, FIG. 13A-F). MPs from the three strains were used to immunize mice and then the mice were challenged with a serotype 1 strain. The data suggest that both MalX and PrsA are needed for cross-protection since mice immunized with MPs from either of the mutant strains showed a lower survival than mice immunized with MPs from the wild type strain (FIG. 12A). Also, the bacterial numbers in the lungs and blood were consistent with the survival data (FIG. 12B, FIG. 13A-F). The inventors concluded that both MalX and PrsA are needed in MPs for cross-protection against a pneumococcal infection.

Example 8: MalX and PrsA are Conserved Lipoproteins in *S. pneumoniae*

To investigate the conservation of prsA and malX, the inventors blasted the nucleotide sequences of these genes against the annotated PubMLST database containing 8351 pneumococcal genomes belonging to several serotypes and sequence types. For prsA, encoding a membrane bound lipoprotein acting as a cis-trans prolyl-isomerase, 99.5% of the pneumococcal genomes (8325/8351 genomes) had a prsA sequence more than 98% identical to the T4 sequence. Similarly, for malX, encoding a lipoprotein acting as an ABC maltose transporter, 98.5% of the genomes (8318/8351) had a malX sequence more than 98% identical to the T4 sequence. This indicates a very high sequence conservation of these two genes across different strains and serotypes of pneumococci. However, single nucleotide polymorphisms, leading to amino-acid replacements, were found.

TABLE A

Proteins identified with LC-MS/MS after immunoprecipitation with immune sera from T4 MPs immunized mice.

| Accession | Protein | Gene number | Annotation | Score | Coverage | # Unique Peptides | # Peptides | MW [kDa] | pI |
|---|---|---|---|---|---|---|---|---|---|
| P95829 | Dnak | SP_0517 | Chaperone protein | 42.90 | 33.94 | 12 | 12 | 64.8 | 4.77 |
| A0A0H2UMZ8 | PspA | SP_0117 | Pneumococcal surface protein A | 23.97 | 16.40 | 7 | 7 | 82.7 | 4.91 |
| A0A0H2UNM7 | RrgB | SP_0463 | Cell wall surface anchor family protein | 9.68 | 10.08 | 4 | 4 | 71.3 | 5.15 |
| Q97SV2 | RplB | SP_0212 | 50S ribosomal protein L2 | 9.13 | 31.77 | 5 | 5 | 29.9 | 10.68 |
| P61182 | RplV | SP_0214 | 50S ribosomal protein L22 | 8.67 | 42.98 | 3 | 3 | 12.2 | 10.76 |
| P06653 | LytA | SP_1937 | Autolysin | 6.54 | 11.95 | 3 | 3 | 36.5 | 5.34 |
| P59213 | MalX | SP_2108 | Maltose/maltodextrin-binding protein | 6.33 | 8.51 | 3 | 3 | 45.3 | 5.22 |
| Q97SU6 | RplR | SP_0226 | 50S ribosomal protein L18 | 5.83 | 29.66 | 2 | 2 | 12.9 | 10.40 |
| P66359 | RpsK | SP_0235 | 30S ribosomal protein S11 | 3.74 | 22.05 | 2 | 2 | 13.4 | 11.43 |

TABLE B

Proteins identified with LC-MS/MS after immunoprecipitation with immune sera from T4ΔpspA MPs immunized mice.

| Accession | Protein | Gene number | Annotation | Score | Coverage | # Unique Peptides | # Peptides | MW [kDa] | pI |
|---|---|---|---|---|---|---|---|---|---|
| Q97R51 | PrsA | SP_0981 | Foldase protein | 81.08 | 53.99 | 21 | 21 | 34.4 | 5.12 |
| P59213 | MalX | SP_2108 | Maltose/maltodextrin-binding protein | 77.02 | 63.36 | 22 | 22 | 45.3 | 5.22 |
| P95829 | Dnak | SP_0517 | Chaperone protein | 42.96 | 37.40 | 16 | 16 | 64.8 | 4.77 |
| Q97SV2 | RplB | SP_0212 | 50S ribosomal protein L2 | 25.95 | 40.79 | 8 | 8 | 29.9 | 10.68 |

TABLE B-continued

Proteins identified with LC-MS/MS after immunoprecipitation with immune sera from T4ΔpspA MPs immunized mice.

| Accession | Protein | Gene number | Annotation | Score | Coverage | # Unique Peptides | # Peptides | MW [kDa] | pI |
|---|---|---|---|---|---|---|---|---|---|
| P61182 | RplV | SP__0214 | 50S ribosomal protein L22 | 24.40 | 58.77 | 5 | 5 | 12.2 | 10.76 |
| A0A0H2UMZ8 | PspA | SP__0117 | Pneumococcal surface protein A | 22.64 | 20.70 | 8 | 8 | 82.7 | 4.91 |
| A0A0H2UNM7 | RrgB | SP__0463 | Cell wall surface anchor family protein | 17.81 | 15.04 | 6 | 6 | 71.3 | 5.15 |
| P66112 | RplT | SP__0961 | 50S ribosomal protein L20 | 12.36 | 41.18 | 4 | 4 | 13.7 | 10.83 |
| P66524 | RpsU | SP__1414 | 30S ribosomal protein S21 | 10.67 | 34.48 | 4 | 4 | 7.0 | 11.30 |
| Q97SQ4 | RpsG | SP__0272 | 30S ribosomal protein S7 | 10.51 | 23.72 | 4 | 4 | 17.7 | 10.51 |
| P06653 | LytA | SP__1937 | Autolysin | 9.28 | 27.36 | 7 | 7 | 36.5 | 5.34 |
| A0A0H2URD1 | | SP__1683 | Sugar ABC transporter | 7.06 | 12.67 | 4 | 4 | 48.3 | 5.44 |
| Q2MGH6 | | SP__0368 | Endo-alpha-N-acetylgalactosaminidase | 6.97 | 4.47 | 7 | 7 | 195.9 | 6.07 |
| P18791 | AmiA | SP__1891 | Oligopeptide-binding protein | 6.62 | 6.37 | 3 | 3 | 72.4 | 5.06 |
| P66581 | RpsE | SP__0227 | 30S ribosomal protein S5 | 6.58 | 24.39 | 3 | 3 | 17.0 | 9.52 |
| P65144 | InfC | SP__0959 | Translation initiation factor IF-3 | 5.40 | 16.22 | 2 | 2 | 21.2 | 9.85 |
| Q97SU6 | RplR | SP__0226 | 50S ribosomal protein L18 | 4.91 | 29.66 | 2 | 2 | 12.9 | 10.40 |
| Q97Q52 | Eno | SP__1128 | Enolase | 4.87 | 11.29 | 3 | 3 | 47.1 | 4.81 |
| A0A0H2UQS8 | MltG | SP__1518 | Endolytic murein transglycosylase | 4.70 | 10.89 | 5 | 5 | 60.8 | 5.16 |
| Q97SN4 | RpsI | SP__0295 | 30S ribosomal protein S9 | 4.68 | 16.92 | 2 | 2 | 14.2 | 10.86 |
| P64030 | EF-Tu | SP__1489 | Elongation factor Tu | 4.49 | 13.07 | 4 | 4 | 43.9 | 4.97 |
| Q9L7Q2 | ZmpB | SP__0664 | Zinc metalloprotease | 4.41 | 4.25 | 5 | 5 | 213.4 | 5.25 |
| A0A0H2UPZ3 | Hup | SP__1113 | DNA-binding protein HU | 4.40 | 35.16 | 2 | 2 | 9.6 | 9.48 |
| P0A4C3 | RpsC | SP__0215 | 30S ribosomal protein S3 | 4.06 | 12.44 | 2 | 2 | 24.0 | 9.70 |
| P66359 | RpsK | SP__0235 | 30S ribosomal protein S11 | 3.85 | 21.26 | 2 | 21 | 13.4 | 11.43 |
| A0A0H2UNF0 | RplM | SP__0294 | 50S ribosomal protein L13 | 3.72 | 14.19 | 2 | 2 | 16.1 | 9.95 |
| A0A0H2XFA2 | LytC | SP__1573 | Lysozyme | 3.16 | 4.69 | 2 | 2 | 57.3 | 6.93 |
| A0A0H2US50 | CbpA | SP__2190 | Choline binding protein A | 2.90 | 9.96 | 3 | 3 | 77.7 | 5.81 |
| P66565 | RpsD | SP__0085 | 30S ribosomal protein S4 | 2.59 | 11.33 | 2 | 21 | 23.0 | 10.15 |
| P0A4A7 | RpsL | SP__0271 | 30S ribosomal protein S12 | 2.21 | 15.33 | 2 | 2 | 15.1 | 11.53 |
| Q97T80 | ZmpC | SP__0071 | Zinc metalloprotease | 1.95 | 6.52 | 8 | 8 | 206.6 | 5.57 |
| Q04707 | PBP-1A | SP__0369 | Penicillin-binding protein 1A | 1.93 | 5.29 | 3 | 3 | 79.7 | 5.60 |

TABLE C

Proteins identified with LC-MS/MS after immunoprecipitation with sera from adjuvant challenged mice

| Accession | Protein | Gene number | Annotation | Score | Coverage | # Unique Peptides | # Peptides | MW [kDa] | pI |
|---|---|---|---|---|---|---|---|---|---|
| P95829 | Dnak | SP__0517 | Chaperone protein | 64.30 | 51.24 | 23 | 23 | 64.8 | 4.77 |
| A0A0H2UNM7 | RrgB | SP__0463 | Cell wall surface anchor family protein | 18.23 | 28.42 | 13 | 13 | 71.3 | 5.15 |
| Q97SV2 | RplB | SP__0212 | 50S ribosomal protein L2 | 16.80 | 32.13 | 6 | 6 | 29.9 | 10.68 |
| P61182 | RplV | SP__0214 | 50S ribosomal protein L22 | 14.97 | 52.63 | 4 | 4 | 12.2 | 10.76 |

TABLE C-continued

Proteins identified with LC-MS/MS after immunoprecipitation with sera from adjuvant challenged mice

| Accession | Protein | Gene number | Annotation | Score | Coverage | # Unique Peptides | # Peptides | MW [kDa] | pI |
|---|---|---|---|---|---|---|---|---|---|
| A0A0H2UMZ8 | PspA | SP_0117 | Pneumococcal surface protein A | 14.78 | 14.11 | 5 | 5 | 82.7 | 4.91 |
| Q97SQ4 | RpsG | SP_0272 | 30S ribosomal protein S7 | 8.81 | 19.23 | 2 | 2 | 17.7 | 10.51 |
| P64030 | EF-Tu | SP_1489 | Elongation factor Tu | 6.97 | 10.80 | 3 | 3 | 43.9 | 4.97 |
| P06653 | LytA | SP_1937 | Autolysin | 6.82 | 26.10 | 7 | 7 | 36.5 | 5.34 |
| Q97SU6 | RplR | SP_0226 | 50S ribosomal protein L18 | 6.42 | 37.29 | 3 | 3 | 12.9 | 10.40 |
| Q97PI9 | RpsO | SP_1626 | 30S ribosomal protein S15 | 5.70 | 21.35 | 3 | 3 | 10.5 | 10.18 |
| P66359 | RpsK | SP_0235 | 30S ribosomal protein S11 | 5.43 | 33.07 | 3 | 3 | 13.4 | 11.43 |
| P65144 | InfC | SP_0959 | Translation initiation factor IF-3 | 5.40 | 16.22 | 2 | 2 | 21.2 | 9.85 |
| P0A4C3 | RpsC | SP_0215 | 30S ribosomal protein S3 | 5.19 | 19.35 | 3 | 3 | 24.0 | 9.70 |
| Q2MGH6 | | SP_0368 | Endo-alpha-N-acetylgalactosaminidase | 3.91 | 1.70 | 3 | 3 | 195.9 | 6.07 |
| A0A0H2XFA2 | LytC | SP_1573 | Lysozyme | 2.85 | 4.69 | 2 | 2 | 57.3 | 6.93 |
| P66565 | RpsD | SP_0085 | 30S ribosomal protein S4 | 2.69 | 10.34 | 2 | 2 | 23.0 | 10.15 |
| P18791 | AmiA | SP_1891 | Oligopeptide-binding protein | 2.52 | 5.16 | 3 | 3 | 72.4 | 5.06 |
| P66524 | RpsU | SP_1414 | 30S ribosomal protein S21 | 2.49 | 34.48 | 4 | 4 | 7.0 | 11.30 |
| A0A0H2UNF0 | RplM | SP _0294 | 50S ribosomal protein L13 | 2.44 | 14.19 | 2 | 2 | 16.1 | 9.95 |
| P66112 | RplT | SP_0961 | 50S ribosomal protein L20 | 2.29 | 29.41 | 2 | 2 | 13.7 | 10.83 |
| P66581 | RpsE | SP_0227 | 30S ribosomal protein S5 | 2.16 | 18.90 | 2 | 2 | 17.0 | 9.52 |
| A0A0H2US50 | CbpA | SP_2190 | Choline binding protein A | 2.12 | 4.91 | 2 | 2 | 77.7 | 5.81 |
| Q9L7Q2 | ZmpB | SP_0664 | Zinc metalloprotease | 2.01 | 2.47 | 3 | 3 | 213.4 | 5.25 |
| P0A4A7 | RpsL | SP_0271 | 30S ribosomal protein S12 | 2.00 | 15.33 | 2 | 2 | 15.1 | 11.53 |
| Q97QP7 | ZmpA | SP_1154 | Immunoglobulin A1 protease | 1.69 | 1.25 | 2 | 2 | 223.8 | 5.38 |

Example 9: Antibodies Raised Against MPs Containing MalX and/or PrsA Recognize the Respective Native Lipoproteins in MPs Considerably Better than to Recombinant PrsA, and MalX Sera from mice immunized with MPs isolated from T4 ΔpspA were used in Western blots on after SDS-PAGE separation of MP-proteins and recombinant PrsA and MalX respectively (FIG. 14). More PrsA and MalX specific antibodies bound the native proteins present in MPs as compared to the respective recombinant protein, despite the much lower content of the antigen present in MPs as compared to the recombinant form. The recombinant form of the protein lacks the amino-terminal sequence corresponding to the signal peptide, and also lacks lipid modification of the terminal cysteine residue required for the formation of membrane bound lipoproteins. These observations indicate that both MalX and PrsA need to be post-translationally modified into lipoproteins (which natively occurs in the N-terminal cysteine of the mature polypeptide) in order to elicit a protective immune response and/or that the dominant antigenic epitopes are not localized in the mature part of the protein but rather on the signal peptide.

Example 10: Artificial Membrane Particles (aMP), Prepared from High Pressure Lysates of *Lactococcus lactis*, Containing Pneumococcal MalX and PrsA Antigens To find a potential platform for vaccine production, the inventors next constructed a *Lactococcus lactis* strain carrying both pneumococcal malX and prsA using an expression vector. *L. lactis* also expresses homologues to pneumococcal MalX and PrsA, but their amino-acid sequences are sufficiently different to not cross-react antigenically. *L. lactis* is not known to spontaneously produce membrane particles during growth like pneumococci, so the inventors purified aMP from high pressure ruptured *L. lactis* cells.

Antisera from mice immunized with T4pspA MPs reacted strongly with the aMPs (FIG. 15), indicating that immune reactive MalX and PrsA antigens were present in the aMPs. Notably, the aMPs did not contain pneumococcal PspA antigen. In conclusion, the aMPs may be used in place of native streptococcal MPs as vaccine antigens, immunogenic compositions and other purposes.

Example 11: Artificial Membrane Particles (aMP), Prepared from High Pressure Lysates of *S. pneumoniae*, Containing Pneumococcal MalX and PrsA Antigens As an additional alternative source of MalX and PrsA antigens, similar aMPs as described in Example 10 and using similar protocol will be made using cultured *S. pneumoniae* cells expressing MalX and PrsA, but deficient in PspA (see Table D strain BHN2258). Similar to Example 10, the isolated aMPs will contain antigenic MalX and PrsA antigens and can be used in lieu of native streptococcal MPs as vaccine antigens, immunogenic compositions and other purposes.

Materials and Methods

Pneumococcal Strains

Strains of *S. pneumoniae* that were used: T4 (TIGR4 of serotype 4) (Tettelin et al., 2001 Science 293, 498-506), its isogenic mutant expressing bioluminescence for IVIS tracking (TIGR4lux), isogenic mutants lacking pneumolysin (T4Δply) (Littmann et al., 2009 EMBO Mol Med 1, 211-222), or the capsule (T4R) (Fernebro et al., 2004 J Infect Dis 189, 328-338), or pspA, prsA, and malX (Table D), BHN733 of serotype 1, BHN428 of serotype 3, and BHN191 of serotype 6B (Iovino et al., 2016a J Clin Invest 126, 2821-2826; Pathak et al., 2018 Nat Commun 9, 3398). T4, BHN733, BHN428 and BHN191 were grown in C+Y-medium, pH 7.9-8.0, at 37° C. Growth was followed by measuring optical density (OD) at 600 nm with a spectrophotometer (Genesys 20, Thermo Spectronic).

type mice 5 weeks old were used. Before immunization, mice were anesthetized by isofluorane (Abbott) inhalation and then challenged intranasally with 50 μl/mouse (10 μg of total protein content/mouse in 50 μl) of EV or MP preparation, either alone or in combination with the adjuvant aluminium hydroxide (Sigma Aldrich, 10 mg/ml in PBS) or PBS or the adjuvant alone for the control groups. Immunization was repeated after two weeks from the first immunization following the same procedure as described above. After four weeks of immunization, mice were infected intranasally (50 μl/mouse) with $5\times10^6$ colony forming units (CFUs) for T4 and type 1, or $1\times10^6$ CFUs for type 3. Mice were anesthetized by isofluorane inhalation prior to bacterial challenge. After the infection, clinical symptoms of the mice were monitored multiple times daily (in accordance with the ethical permit). Blood samples (5 al/mouse) were taken every infection day and bacteremia levels were assessed by plating serial dilutions of blood samples onto blood-agar plates. Mice that reached humane end-points were sacrificed according to ethical regulations. For IVIS imaging, mice were anesthetized by isofluorane inhalation and treated intranasally (50 μl/mouse) with Bacterisense 645 (Perkin Elmer) approximately 30 minutes prior to imaging, which was performed after sacrifice. Lungs and spleens were

TABLE D

*S. pneumoniae* strains used in the study.

| Strain | Identifier | Comment |
|---|---|---|
| T4 (TIGR4) | BHN38 | Wild-type TIGR4 serotype 4 |
| Serotype 1 | BHN733 | Wild-type serotype 1 |
| Serotype 3 | BHN428 | Wild-type serotype 3 |
| Serotype 6B | BHN191 | Invasive meningitis clinical isolate serotype 6B |
| T4ΔpspA | BHN2258 | pspA (SP0117) replaced with an ermB cassette (promoter plus Orf) |
| T4ΔmalX::kanR | BHN1696 | malX (SP2108) Orf replaced with a kanR Orf |
| T4ΔprsA::tetM | BHN1697 | prsA (SP0981) Orf replaced with a tetM Orf |
| T4ΔpspA::ermBΔmalX::kanR | BHN1698 | pspA (SP0117) replaced with an ermB cassette (promoter plus Orf); malX (SP2108) Orf replaced with a kanR Orf |
| T4ΔpspA::ermBΔprsA::tetM | BHN1699 | pspA (SP0117) replaced with an ermB cassette (promoter plus Orf); prsA (SP0981) Orf replaced with a tetM Orf |
| T4ΔpspA::ermBΔprsA::tetMΔmalX::kanR | BHN1700 | pspA (SP0117) replaced with an ermB cassette (promoter plus Orf); prsA (SP0981) Orf replaced with a tetM Orf; malX (SP2108) Orf replaced with a kanR Orf |

Preparation of EVs and MPs

EV were isolated from liquid cultures as described before (Codemo et al, 2018 MBio 9). Briefly, bacteria were grown in C+Y medium until $OD_{600nm}$=0.9, and removed by centrifugation, the supernatant filtered and centrifuged. Vesicles were washed twice and resuspended in PBS. MPs were isolated from plate-grown bacteria. Briefly, bacteria were grown overnight on blood agar plates at 37° C. with 5% $CO_2$, scraped off from the plates, resuspended in PBS and removed by centrifugation (17000 rcf, 30 min). The supernatant was passed through a 0.2 μm filtering device (Filtropur S 0.2, Sarstedt) (except for type 3), and ultracentrifuged (170000 rcf, 12 hours). Pelleted vesicles were resuspended in PBS. Both EV and MP were further purified using Optiprep™ Density Gradient Medium (Sigma). After being resuspended in PBS, EV and MP protein concentrations were assessed by Pierce BCA Protein Assay Kit (Thermo Scientific) and preparations were stored at −80° C.

Animal Experiments

All animal experiments were approved by the local ethical committee (Stockholms Norra djurförsöksetiska nämnd). For each immunization experiment, male C57BL/6 wild-collected for further analyses. Bacterial CFUs were calculated after plating serial dilutions of lung homogenates onto blood-agar plates. To define the ROIs for each mouse with the IVIS system, the fluorescent signal intensity was quantified using the imaging software Living Image 4.5 (Perkin Elmer). MuMt knock-out mice in the C57BL/6 background (Jackson Laboratories) were used as the B cell deficient model.

SDS-PAGE and Western Blotting

Detection of pneumococcal proteins in EV and MP was performed as previously described (Codemo M. et al. mBio. 2018 Apr. 10; 9(2) e00559-18; Mellroth et al. J Biol Chem. 2012; 287(14):11018-29). Briefly, Pierce™ BCA Protein Assay Kit (Life Technologies) was used to determine the total protein quantity in EV or MP. Samples were resolved by SDS-PAGE using NuPAGE 4-12% Bis-Tris protein gels (Invitrogen) and electroblotted onto PVDF membranes. Membranes were blocked with 5% skim milk in PBS containing 0.1% Tween-20 and incubated with sera from immunized mice (as primary antibodies, 1:5000) and horseradish peroxidase (HRP)-conjugated secondary antibodies. Membranes were developed with Amersham™ ECL Plus Western blotting detection system (GE Healthcare Life Sciences), using a ChemiDoc™ XRS+(Bio-Rad Laboratories). For Western blot detection using bacterial lysates, T4, T4ΔpspA, T4ΔprsA, T4ΔmalX, T4ΔpspAΔprsA, T4ΔpspAΔmalX, and T4ΔpspAΔprsAΔmalX were grown overnight on blood agar plates and inoculated in C+Y medium at 37° C. These pre-cultures were grown to mid-log phase and used to start new cultures in C+Y media at $OD_{620}$=0.05. When the cultures reached $OD_{620}$=0.5 (0.5 mL), each strain was centrifugated (10000 rpm, 5 min) and the cell pellet washed with 1 ml PBS, centrifugated (10000 rpm, 5 min), dissolved in 250 μL of 1x SDS-PAGE loading buffer including 25 mM 1,4-dithiothreitol (DTT) and then boiled for 5 min. For assessment of sera binding to pneumococcal choline binding proteins (CBPs), cells were after growth incubated with 5% choline chloride for 10 minutes at 37 2C, centrifuged and the supernatant collected. The pellet was washed with 5% choline chloride to remove CBPs. Pellets and supernatant fractions were mixed with loading buffer and Western Blot analysis was performed as described above.

Immunoprecipitation

A column-based immunoprecipitation protocol was set up using the Protein G HP SpinTrap/Ab Spin Trap kit (GE Healthcare). The resin from the Protein G sepharose kit columns were washed three times with PBS and then removed from the columns and transferred to Eppendorf tubes in a 300 μL slurry in PBS. Samples (100 μL) of ten-fold diluted immune sera from mice immunized with MPs from T4 and T4ΔpspA and of sera from adjuvant challenged mice were added to the resin in separate tubes and incubated for 30 min in room temperature. Following incubation, the resins were washed twice with 400 μL PBS using centrifugation (100 rfc, 1 min). The pelleted resin fractions, containing IgG molecules from the immune sera, were resuspended in 400 μL of a pneumococcal cell lysate from T4 generated from mid-log phase cultures grown in C+Y media at 37° C., and transferred to Eppendorf tubes (500 μL per tube) and treated with 5 μL 10% Triton X100 (0.1% end concentration) for 30 min to induce prominent autolysin-mediated lysis of the cultures. These lysates were centrifugated (14000 rpm, 5 min) to remove cell wall debris and 400 μL of the supernatant was used per sample. The lysate/antisera-Protein G sepharose mixtures were incubated for 30 min in room temperature after which the samples were transferred back to the spin columns, fitted into collection tubes and centrifugated (100 rfc, 1 min) to remove unbound proteins. The columns were successively washed five times with 400 μL PBS (with centrifugation (100 rfc, 1 min)) and elution was done with 400 μL 100 mM sodium citrate buffer, pH 2.5, with centrifugation (100 rfc, 1 min) and the samples were collected into tubes containing 40 μL 1 M Tris buffer pH 8.0 to neutralize the pH. Samples were concentrated using SpedVac (Thermo Fisher) to 100 μL, frozen, and sent for mass spectrometry analysis.

Mass Spectrometry

Analysis of EVs and MP was performed as described previously (Codemo M. et al. mBio. 2018 Apr. 10; 9(2) e00559-18). Briefly, a urea-containing buffer was used to lyse EV and MP. Proteins were reduced, alkylated, and digested in-solution by trypsin. A Pierce C18 Spin Column (Thermo Scientific) was used to purify the sample that was dried and resolved in 0.1% formic acid. Peptides were separated in reversed-phase on a C18-column and electrosprayed on-line to a Q Exactive Plus mass spectrometer (Thermo Finnigan). Tandem mass spectrometry was performed applying HCD. The Sequest algorithm in Proteome Discoverer 1.4 (Thermo Scientific™) was used to search databases towards a FASTA database of TIGR4 (for serotype 4) or SP3-BS71 (for serotype 3) proteins from UniProtKB. Criteria for protein identification were at least two matching peptides of 95% confidence level. In order to avoid false positives, only proteins with a score of 20 or above were included in the analysis. Subcellular localizations of proteins were predicted as before (Codemo M. et al. mBio. 2018 Apr. 10; 9(2) e00559-18).

For analysis of the immunoprecipitation samples, the following mass spectrometry setup was used. Chemicals and reagents. Acetonitrile (ACN), formic acid (FA), and ammonium bicarbonate ($NH_4HCO_3$) were obtained from Merck. Protease inhibitor cocktail and trifluoroacetic acid (TFA) were purchased from Sigma-Aldrich. For tryptic digestion, iodoacetamide (IAA), urea, and dithiothreitol (DTT) were obtained from Sigma-Aldrich and grade modified trypsin (V5073) was from Promega. Ultrapure water was prepared by Milli-Q water purification system (Millipore). In-solution tryptic digestion of proteins. The whole volume of the samples (100 μL) was used for in-solution digestion. A volume of 10 μL of 45 mM DTT was added and the mixtures were incubated at 50° C. for 15 min and then cooled to ambient temperature. Then 10 μl 100 mM IAA was added, and the mixtures were incubated for 15 minutes at room temperature in darkness. Finally, trypsin solution was added to yield a final trypsin/protein concentration of 5% (w/w). The tryptic digestion was performed at 37° C. overnight in darkness. Thereafter the samples were desalted using the SPE Pierce C18 Spin Columns (Thermo Scientific). These columns were activated by 2×200 μL 50% ACN and equilibrated with 2×200 μL 0.5% TFA. The tryptic peptides were adsorbed to the media using two repeated cycles of 40 μL sample loading and the column was washed using 3×200 μL 0.5% TFA. Finally, the peptides were eluted in 3×50 μL 70% ACN and dried. Dried peptides were resolved in 30 μL 0.1% FA prior to nano-LC-MS/MS. LC-MS/MS analysis. The nanoLC-MS/MS experiments were performed using Q Exactive Orbitrap mass spectrometer (ThermoFisher Scientific, Bremen, Germany) equipped with a nano electrospray ion source. The peptides were separated by C18 reversed phase liquid chromatography using an EASY-nLC 1000 system (Thermo Fisher Scientific). A set-up of pre-column and analytical column was used. The precolumn was 2 cm EASYcolumn (ID 100 μm, 5 μm particles) (Thermo Fisher Scientific) while the analytical column was 10 cm EASY-column (ID 75 μm, 3 μm particles, Thermo Fisher Scientific). Peptides were eluted with a 90 min linear gradient from 4% to 100% acetonitrile at 250 nL min-1. The mass spectrometer was operated in positive ion mode acquiring a survey mass spectrum with resolving power 70,000 (full width half maximum), m/z 400-1750 using an automatic gain control (AGC) target of $3\times10^6$. The 10 most intense ions were selected for higher-energy collisional dissociation (HCD) fragmentation (25% normalized collision energy) and MS/MS spectra were generated with an AGC target of 5×105 at a resolution of 17,500. The mass spectrometer worked in data-dependent mode. Data analysis. The acquired data (.RAW-files) were processed by Proteome Discoverer software (Thermo Scientific, version [nr 1.4.1.14]) using the Sequest algorithm towards a combined database containing protein sequences from the strain TIGR4 proteome (2178 entries) downloaded from Uniprot 2019-10. The following parameters were used for data processing: maximum 10 ppm and 0.02 13 Da error tolerances for the survey scan and MS/MS analysis, respectively, trypsin as digesting enzyme, carbamidomethylation of cysteins as fixed modification, oxidation of methionine as variable modification, maximum of two miss cleavages sites. The target decoy PSM validator was used to calculate false discovery rate (FDR). An FDR of maximum 5% for peptide identification was accepted and the search criteria for protein identification were set to at least two matching peptides per protein.

Quantification of Fluorescence Signal In Vivo

Mice treated with Bacterisense 645 were imaged at the IVIS Spectrum Imaging System focusing on the upper respiratory tract. To define the ROIs for each mouse, the fluorescent signal intensity was quantified using the imaging software Living Image 4.5 (Perkin Elmer).

Mouse IgG ELISA Assay

To detect EV- or MP-specific mouse IgG in sera of immunized mice, 96 well optical plates (Sarstedt) were coated with 1 μg/ml of EV or MP in 0.1 M Sodium Carbonate buffer pH 9.5, overnight at 4° C. Wells were washed three times with PBS containing 0.05% Tween-20 and incubated with 200 μl PBS with 10% FBS for 1 hour at room temperature. After three washes, wells were incubated with 100 μl mice sera diluted 1:500 in PBS with 10% FBS for 2 hours, and then washed three times and incubated with 100 μl anti-mouse IgG-HRP (GE Healthcare) diluted 1:500 in PBS 10% FBS for 2 hours, at room temperature. After three washes, wells were incubated with TMB substrate (BD Bioscience) for 10 minutes and the reaction was stopped with 1 M $H_3PO_4$. Absorbance at 450 nm was measured with a plate reader.

To detect T4 and T4R-specific mouse IgG in sera of T4 EV, T4 MP and T4R MP immunized mice, bacteria were grown on blood agar plates overnight at 37° C., resuspended in PBS and heat-inactivated for 2 hours at 60° C. After diluting the bacteria to $OD_{600}$ 0.6, optical plates were coated with 100 μl bacteria in 0.1 M Sodium Carbonate buffer pH 9.5 overnight at 4° C. Wells were washed three times and incubated with 200 μl PBS with 2.5% skim milk for 2 hours, and after three washes incubated with 100 μl mice sera diluted 1:500 in PBS for one hour, at room temperature. Wells were washed three times and incubated with 100 μl anti-mouse IgG-HRP diluted 1:500 in PBS for one hour at room temperature, and the procedure was continued as described above.

To detect T4, serotype 1 (BHN733) and serotype 3 (BHN428)-specific mouse IgG in sera of mice immunized with T4 MP and T4ΔpspA MP, bacteria were grown on blood agar plates overnight at 37° C., resuspended in PBS and heat-inactivated for 2 hours at 60° C. After diluting the bacteria to $OD_{600}$ 0.6, optical plates were coated with 100 μl bacteria in PBS with complete Protease Inhibitor Cocktail (Roche) overnight at 4° C. Wells were washed three times and incubated with 200 μl PBS with 2.5% skim milk for 2 hours, and after three washes incubated with 100 μl mice sera diluted 1:1000 in PBS with 1% BSA, for one hour in room temperature. Wells were washed three times and incubated with 100 μl anti-mouse IgG-HRP diluted 1:1000 in PBS with 1% BSA for one hour at room temperature, and the procedure was continued as described above.

Construction of Pneumococcal Mutant Strains

For generation of pneumococcal mutants using transformation, a general procedure was employed as previously described (Balaban et al., 2014 Proc Natl Acad Sci USA 111, E758-765). To generate double and triple mutants, the same procedure was iterated using sequenced mutants that had acquired the corresponding mutations. Confirmation of mutants were done with Sanger sequencing of PCR amplicons covering the cognate loci (Tables D, E).

Pneumococcal mutants were created in which the open reading frames (Orfs) of pspA (SP0117), prsA (SP0981) and malX (SP2108), (gene numbers in parenthesis), were deleted and replaced with antibiotic resistance Orfs (prsA and malX) or a cassette consisting of a promoter and Orf (pspA) as indicated in Extended Data Table 4. Transformation constructs were made with sequential extension overlap PCR were the ~700 bp upstream and ~700 bp downstream regions flanking the target genes were PCR amplified from genomic DNA isolated from T4 with primers given in Table E. These primers contained non-annealing overhang sequences complementary to the 5' and 3' ends of the antibiotic Orfs or cassette to be fused. In a second PCR ~700 bp up- and down-stream regions were fused to the corresponding antibiotic cassette (or Orf) through thermal annealing followed by overlap extension PCR. The final PCR products that contained the joined (700 bp upstream region plus the antibiotic resistance Orf or cassette plus the 700 bp downstream region) were purified (PCR clean up kit (Qiagen)) and used to transform the T4 strain.

TABLE E

Primers used in the study

| SED ID NO | Primer | Sequence[1] | Comment |
|---|---|---|---|
| 1 | pspA-UpFr-800 | ggagtttgtcgttgaaattac | Anneals ~800 bp upstream of pspA Start codon |
| 2 | pspA-UpFr-700 | gtatttagagattttcaaagtg | Anneals ~700 bp upstream of pspA Start codon |
| 3 | pspA-UpRe-ErmCass-OH | TGCAAGTCACACGAACACGAAc taaatttacctcttttctgata g | Anneals directly upstream of pspA start codon with an overhang seq. complementary to the ermB cassette |
| 4 | pspA-DoFr-ErmCass-OH | CTATTATTTAACGGGAGGAAAT AAgccgattaaattaaatcatg | Anneals directly downstream of pspA stop codon with an overhang seq. complementary to the ermB cassette |
| 5 | pspA-DoRe-700 bp | acgtccggatttggcgtgc | Anneals ~700 bp downstream of pspA Stop codon |
| 6 | pspA-DoRe-800 bp | ccactcgagcataatgcc | Anneals ~800 bp downstream of pspA Stop codon |

TABLE E-continued

Primers used in the study

| SED ID NO | Primer | Sequence[1] | Comment |
|---|---|---|---|
| 7 | Erm-cass-frw | ttcgtgttcgtgtgacttgca | |
| 8 | Erm-cass-rev | ttatttcctcccgttaaataatag | |
| 9 | prsA-UpFr-800 | aggattggcataaaatggttg | Anneals ~800 bp upstream of prsA Start codon |
| 10 | prsA-UpFr-700 | ggtttcttgaaagaattgga | Anneals ~700 bp upstream of prsA Start codon |
| 11 | prsA-UpRe-TetOH | TAATTTTCATGTGATTTTCCTCCATgtctactcctttgagataagtg | Anneals directly upstream of prsA start codon with an overhang seq. complementary to the beginning of the tetM Orf |
| 12 | prsA-DoFr-TetOH | ATATATGTTCAATAAAATAACTTAGtccaaatcaatgagtcaggga | Anneals directly upstream of prsA stop codon with an overhang seq. complementary to the end of the tetR Orf |
| 13 | prsA-DoRe-800 | aacgcatcatatcaggtgtac | Anneals ~800 bp downstream of prsA Stop codon |
| 14 | prsA-DoRe-700 | aacgcatcatatcaggtgtac | Anneals ~700 bp downstream of prsA Stop codon |
| 15 | TetOrf-frw | atggaggaaaatcacatgaaaatta | |
| 16 | TetOrf-rev | ctaagttattttattgaacatatat | |
| 17 | malX-UpFr-800 | gcttccaacaaaccttgctc | Anneals ~800 bp upstream of malX Start codon |
| 18 | malX-UpFr-700 | gctcctaatggaaggatttg | Anneals ~700 bp upstream of malX Start codon |
| 19 | malX-UpRe-KanOH | ctattctttaggaggaatacactATGGCTAAAATGAGAATATCA | Anneals directly upstream of malX start codon with an overhang seq. complementary to the beginning of the kanR Orf |
| 20 | malX-DoFr-KanOH | acccccttgaacaaatttttCTAAAACAATTCATCCAGTAAA | Anneals directly upstream of malX stop codon with an overhang seq. complementary to the end of the kanR Orf |
| 21 | malX-DoRe-800 | gaaaataacaccaaagatacgt | Anneals ~800 bp downstream of malX Stop codon |
| 22 | malX-DoRe-700 | agcccaaatgatagtccaag | Anneals ~700 bp downstream of malX Stop codon |
| 23 | KanOrf-frw | atggctaaaatgagaatatca | |
| 24 | KanOrf-rev | ctaaaacaattcatccagtaaa | |

Notes:

[1]annealing sequences in lower case and non-annealing overhang sequences in upper case letters Pneumococcal Transformation For pneumococcal transformation, a general procedure was employed as previously described (Mellroth P. et al. J. Biol. Chem. 2012 30; 287(14):11018-29). To generate double and triple mutants the same procedure was iterated using sequenced mutant isolates that had acquired the corresponding mutations. Confirmation of mutants were done with Sanger sequencing of PCR amplicons from genomic DNA of isolated mutants using primers that annealed ~800 bp of the cognate loci (thus outside the constructs used for transformation) (primer sequences in Table E). Strains produced are listed in Table D.

Immunofluorescence Microscopy

After growth, pneumococci (serotypes 1, 3 and 6B) were stained using sera from immunized mice as primary antibody (dilution 1:100 in PBS 1% BSA) followed by incubation with the secondary antibody Alexa Fluor 488 goat anti mouse (dilution 1:500 in PBS 1% BSA). Imaging was performed using a DV Elite microscope (Applied Precision) and a scientific complementary metal-oxide-semiconductor (sCMOS) camera. Images were acquired with FITC Laser intensity 50% and exposure time 200 ms using Softworx (Applied Precision).

Quantification of the Signal Detected on the Bacteria after Immunofluorescence Staining Using the functions Image>Adjust>Threshold and Analyze>Measure of ImageJ, the area covered by the bacteria and the area covered by the signal detected on the bacteria after staining with sera were selected, defined and measured. The final signal ratio was calculated by dividing the area of the signal (detected using the sera) by the total area of the bacteria.

Opsonophagocytosis Assay with RAW Cells

RAW 264.7 murine macrophages were grown and maintained at 37° C., 5% $CO_2$ in RPMI medium (Gibco) supplemented with 10% (v/v) Fetal bovine serum (FBS) (HyClone). To assess the opsonophagocytic activity of antibodies in immunized mice sera, $2\times10^5$ RAW 264.7 cells were seeded in 24-well plates and incubated overnight at 37° C. Serotype 1 bacteria were incubated for 30 minutes at 37° C. with 5% $CO_2$ with 20% serum from mice. RAW cells were then washed with PBS and incubated for 1.5 hours with $2.5\times10^7$/well of pre-treated bacteria. Cells were washed three times with PBS to remove unattached bacteria. To measure total uptake of bacteria, cells were incubated with a 50/50 solution of 2% saponin (Sigma) and trypsin-EDTA (Gibco) for 15 minutes at 37° C., to lyse eukaryotic cells, and total bacteria were plated for enumeration. To evaluate phagocytosis, 300 μg/ml of Gentamicin (Sigma) and 0.12 mg/ml of Penicillin G (Sigma) were added to separate wells and incubated 15 minutes at 37° C. to kill extracellular bacteria. Cells were washed three times with PBS and incubated with a 50/50 solution of 2% saponin and trypsin-EDTA for 15 minutes at 37° C. to lyse eukaryotic cells. To evaluate bacterial killing inside macrophages, separate wells were treated with antibiotics (as for phagocytosis), washed three times with PBS and incubated for one hour at 37° C. with medium. Cells were washed three times with PBS and incubated with a 50/50 solution of 2% saponin and trypsin-EDTA for 15 minutes at 37° C. to lyse eukaryotic cells.

Preparation of *L. lactis* Artificial Membrane Particles (aMP) Containing Pneumococcal MalX and PrsA DNA Techniques and Primer Sequences Primers were designed based on the genomes of *S. pneumoniae* TIGR4 and *L. lactis* subsp. *cremoris* MG1363. All PCRs were conducted with Phusion Master Mix HF (Thermo Scientific). Obtained plasmids were confirmed by PCR and sequencing. All primers used are listed in Table E.

Cloning of P23, prsA and malX into pORI

The strong *L. lactis* promotor P23 was cloned in plasmid pORI (provided by Ulrich von Pawel-Rammingen, Umeå University, Sweden; Que et al. 2020 Infection and Immunity Vol. 68, No. 6) by FastCloning (Li et al., 2011 BMC Biotechnol 11, 92) resulting in plasmid pORI-P23 (SEQ ID NO: 64). The plasmid backbone was amplified with primers CS-pORI-new-r (GACTAGCAAATACTAACAACAAG) and CS-pORI-new-f (GGATCCGTCGACCTGCAG), and the insert was amplified from genomic DNA from *L. lactis* subsp. *cremoris* MG1363 (provided by Harold Marcotte, Karolinska Institutet, Sweden) with primers CS-P23-f2 (CTTGTTGTTAGTATTTGCTAGTCGAATTCGAAAAGCCCTGACAACGC) and CS-P23-r (CTGCAGGTCGACGGATCCAACATCATTGTCATTCATATTTTTC).

prsA and malX were amplified *S. pneumoniae* TIGR4 with primers CS-prsA-f (GGGAGGCCAAATATAATGAAGAAAAAATTATTGGCAG), CS-prsA+4nt-r (GACATAGTGTATTCCTCCTAAATGGACTATTCGTTTGATGTAC), CS-malX-17nt-f (GTACATCAAACGAATAGTCCATTTAGGAGGAATACACTATGTC) and CS-malX+56nt-r (AAGCGGAAGAGCGTCTATCTCTATTGATAAATTCAAAGG). The two fragments were joined by Gibson Assembly system (New England Biolabs). The assembled fragment encoding an artificial prsA-malX operon was amplified by PCR with the flanking primers. This fragment was then cloned into pORI-P23 by FastCloning using primers CS-pORI23-ori-Coll-f (TAGACGCTCTTCCGCTTC) and CS-pOR123-P23-r (TCATTATATTTGGCCTCCC) for plasmid backbone amplification and directly transformed through electroporation into *L. lactis* subsp. *cremoris* MG1363 as previously described (King et al., 2015 In Methods in Enzymology, A. K. Shukla, ed. (Academic Press), pp. 77-97). In addition, also empty pOR123 was transformed into the same background. The resulting *L. lactis* strains carrying the plasmid pORI-P23-prsA-malX and pORI-P23 were used for subsequent preparation of artificial membrane particles (aMP).

TABLE F

Sequences for *Lactobacillus* experiments

| SED ID NO | Designation | Sequence[1] |
|---|---|---|
| 54 | CS-pORI-new-r | gactagcaaatactaacaacaag |
| 55 | CS-pORI-new-f | ggatccgtcgacctgcag |
| 56 | CS-P23-f2 | cttgttgttagtatttgctagtcgaattcgaaaagccctgacaacgc |
| 57 | CS-P23-r | ctgcaggtcgacggatccaacatcattgtcattcatatttttc |
| 58 | CS-prsA-f | gggaggccaaatataatgaagaaaaaattattggcag |
| 59 | CS-prsA + 4nt-r | gacatagtgtattcctcctaaatggactattcgtttgatgtac |
| 60 | CS-malX − 17nt-f | gtacatcaaacgaatagtccatttaggaggaatacactatgtc |
| 61 | CS-malX + 56nt-r | aagcggaagagcgtctatctctattgataaattcaaagg |

TABLE F-continued

Sequences for *Lactobacillus* experiments

| SED ID NO | Designation | Sequence[1] |
|---|---|---|
| 62 | CS-pORI23 - oriCol1-f | tagacgctcttccgcttc |
| 63 | CS-pORI23-P23-r | tcattatatttggcctccc |
| 64 | pORI-P23 | |

Preparation of *L. lactis* Artificial Membrane Particles (aMP)

*L. lactis* strains carrying the plasmids pORI-P23-prsA-malX and pORI-P23 were grown overnight at 30° C. without aeration or agitation in M17 (Sigma-Aldrich) supplemented with 1% Glucose and 5 μg/ml erythromycin. The following day the cultures were diluted to OD 0.1 and grown in the same condition to OD 0.85. Cells were then collected by centrifugation for 20 min at 11'000 g and washed with PBS. Cells were disrupted by applying one time 30 kpsi with a 'Pressure cell' Homogeniser EP FPG12805 (Homogenising Systems Ltd). The cell lysate was clarified by centrifugation at 11'000 g for 20 min prior to sterile filtration of the supernatant through a 0.45 μm filter. MVs were then collected by ultra-centrifugation at 31'000 g for 16 h. The resulting pellet was washed in PBS by another round of ultra-centrifugation for 3 h. Pellets were thereafter suspended in PBS and protein concentrations of the MV preparations were assessed by Pierce BCA Protein Assay Kit (Thermo Scientific) prior to storage at −80° C. Similar procedure is also applicable to e.g. *S. pneumoniae* cells.

Statistical Analysis

Statistical analysis for multiple comparisons was done using a nonparametric ANOVA test, and Dunn's test was applied to assess differences between pairs. Two groups comparisons were analyzed using a nonparametric two-tailed Mann-Whitney test. Analysis of survival curves was done using a log-rank Mantel-Cox test. Statistically significant data was defined as * $p<0.05$,  $p<0.01$, * $p<0.001$ ****= $p<0.0001$.

The invention claimed is:

1. An immunogenic composition comprising bacterial membrane vesicles (MVs) comprising a streptococcal MalX antigen and/or a streptococcal PrsA antigen, characterized in that the MVs do not comprise an immunogenic amount of a streptococcal PspA antigen.

2. An immunogenic composition comprising a streptococcal MalX antigen and a streptococcal PrsA antigen associated with membrane vesicles from a host cell, characterized in that the MalX antigen and the PrsA antigen are not associated with a membrane vesicle derived from the same strain as the antigens, and
   wherein the sequence(s) of the MalX antigen and the PrsA antigen are derived from *Streptococcus pneumoniae*.

3. The composition according to claim 1, wherein the MVs comprise streptococcal MVs.

4. The composition according to claim 1, wherein the antigen(s) is/are associated with membrane vesicles from a host cell, where the antigen(s) is/are heterologous in relation to the host cell.

5. The composition according to claim 4, wherein the host cell is of the genus *Lactococcus*.

6. The composition according to claim 2, wherein the host cell is of the genus *Lactococcus*.

7. The composition according to claim 5, wherein the host cell is a *Lactococcus lactis* cell.

8. The composition according to claim 6, wherein the host cell is a *Lactococcus lactis* cell.

9. The composition according to claim 1, wherein the membrane vesicles are artificial membrane particles.

10. The composition according to claim 2, wherein the membrane vesicles are artificial membrane particles.

11. The composition according to claim 1, wherein the membrane vesicles comprise disrupted bacterial cells.

12. The composition according to claim 1, wherein the composition comprises the MalX antigen.

13. The composition according to claim 1, wherein the composition comprises the PrsA antigen.

14. The composition according to claim 13, wherein the composition comprises both the MalX antigen and the PrsA antigen.

15. The composition according to claim 14, wherein both the PrsA antigen and the MalX antigen are present at relative amounts of 10:1 to 1:10 by weight.

16. The composition according to claim 1, wherein the PspA antigen is absent or present at a concentration of less than 0.01 μg/ml.

17. The composition according to claim 2, wherein the composition further comprises a nanoparticle carrier.

18. The composition according to claim 1, wherein the composition is devoid of whole *Streptococcus* cells.

19. The composition according to claim 2, wherein the composition is devoid of whole *Streptococcus* cells.

20. A method of treatment for inducing protective immunity against a *Streptococcus* sp. in a subject, comprising administering to the subject:
   (i) a composition comprising bacterial membrane vesicles (MVs) comprising a streptococcal MalX antigen and/or a streptococcal PrsA antigen, characterized in that the MVs do not comprise an immunogenic amount of a streptococcal PspA antigen; or
   (ii) a composition comprising a streptococcal MalX antigen and a streptococcal PrsA antigen associated with membrane vesicles from a host cell, characterized in that the MalX antigen and the PrsA antigen are not associated with a membrane vesicle derived from the same strain as the antigens, wherein the sequence(s) of the MalX antigen and the PrsA antigen are derived from *Streptococcus pneumoniae*.

* * * * *